(12) United States Patent
Arora et al.

(10) Patent No.: US 7,601,726 B2
(45) Date of Patent: *Oct. 13, 2009

(54) SUBSTITUTED PYRAZOLO[3,4-D]PYRIMIDINES AS P38 MAP KINASE INHIBITORS

(75) Inventors: Nidhi Arora, Cupertino, CA (US); Nolan James Dewdney, San Jose, CA (US); Tobias Gabriel, San Francisco, CA (US); Kristen Lynn McCaleb, Daly City, CA (US); Michael Soth, Milpitas, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 61 days.

This patent is subject to a terminal disclaimer.

(21) Appl. No.: 11/509,240

(22) Filed: Aug. 23, 2006

(65) Prior Publication Data

US 2007/0054915 A1    Mar. 8, 2007

Related U.S. Application Data

(60) Provisional application No. 60/712,009, filed on Aug. 25, 2005.

(51) Int. Cl.
| C07D 487/04 | (2006.01) |
| A61K 31/519 | (2006.01) |
| A61P 11/04  | (2006.01) |
| A61P 19/02  | (2006.01) |

(52) U.S. Cl. .................... 514/262.1; 544/262; 544/350; 514/249; 514/303; 546/119

(58) Field of Classification Search .................. 544/118, 544/244, 262, 238; 514/234.5, 81, 262.1, 514/252.02
See application file for complete search history.

(56) References Cited

U.S. PATENT DOCUMENTS

| 3,872,133 A | 3/1975 | Aktiengesellschaft |
| 2004/0138286 A1 | 7/2004 | Imazaki et al. |
| 2004/0192653 A1 | 9/2004 | Munson et al. |
| 2004/0254177 A1 | 12/2004 | Amici et al. |
| 2005/0070542 A1 | 3/2005 | Hodgetts et al. |

| 2005/0113379 A1 | 5/2005 | Ge et al. |

FOREIGN PATENT DOCUMENTS

| FR | 2 190 824 | 2/1974 |
| WO | WO 02/100833 A1 | 12/2002 |
| WO | WO 03/028720 A1 | 4/2003 |
| WO | WO 03/099820 A1 | 4/2003 |
| WO | WO 2004/078116 A2 | 9/2004 |
| WO | WO 2004/078116 A3 | 9/2004 |
| WO | WO 2004/113303 A1 | 12/2004 |
| WO | WO 2005/023806 A2 | 3/2005 |
| WO | WO 2005/023806 A3 | 3/2005 |
| WO | WO 2005/028480 A2 | 3/2005 |
| WO | WO 2005/063766 A2 | 7/2005 |
| WO | WO 2005/063766 A3 | 7/2005 |

OTHER PUBLICATIONS

Gong, P. et. al., "Synthesis and Vasodilatory Activities of New Pyrazolo [3,4-d] pyrimidin-4-one Derivatives," *Chinese Chemical Letters* vol. 13, No. 7 (2002) pp. 613-616.

*Primary Examiner*—James O Wilson
*Assistant Examiner*—Susanna Moore
(74) *Attorney, Agent, or Firm*—Robert C. Hall

(57) ABSTRACT

Compounds of formula Ia or Ib:

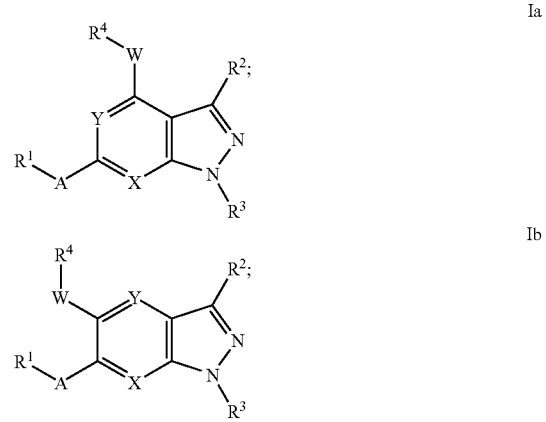

wherein A, W, X, Y, $R^1$, $R^2$, $R^3$ and $R^4$ are as defined herein. Also disclosed are methods of making the compounds and methods of using the compounds for treatment of p38 MAP kinase-mediated diseases.

17 Claims, No Drawings

SUBSTITUTED PYRAZOLO[3,4-D]PYRIMIDINES AS P38 MAP KINASE INHIBITORS

CROSS REFERENCE TO RELATED APPLICATIONS

This application is entitled to the benefit of provisional patent application Ser. No. 60/712,009 filed on Aug. 25, 2005, the disclosure of which is incorporated herein by reference.

FIELD OF THE INVENTION

The present invention relates to fused pyrazolo pyrimidine derivatives and related compounds, a process for their manufacture, pharmaceutical preparations comprising the same, and methods for using the same.

BACKGROUND OF THE INVENTION

Mitogen-activated protein kinases (MAP) is a family of proline-directed serine/threonine kinases that activate their substrates by dual phosphorylation. The kinases are activated by a variety of signals including nutritional and osmotic stress, UV light, growth factors, endotoxin and inflammatory cytokines. One group of MAP kinases is the p38 kinase group that includes various isoforms (e.g., p38α, p38β, p38γ and p38δ). The p38 kinases are responsible for phosphorylating and activating transcription factors as well as other kinases, and are activated by physical and chemical stress, pro-inflammatory cytokines and bacterial lipopolysaccharide.

More importantly, the products of the p38 phosphorylation have been shown to mediate the production of inflammatory cytokines, including TNF and IL-1, and cyclooxygenase-2. Each of these cytokines has been implicated in numerous disease states and conditions. For example, TNF-α is a cytokine produced primarily by activated monocytes and macrophages. Its excessive or unregulated production has been implicated as playing a causative role in the pathogenesis of rheumatoid arthritis. More recently, inhibition of TNF production has been shown to have broad application in the treatment of inflammation, inflammatory bowel disease, multiple sclerosis and asthma.

TNF has also been implicated in viral infections, such as HIV, influenza virus, and herpes virus including herpes simplex virus type-1(HSV-1), herpes simplex virus type-2(HSV-2), cytomegalovirus (CMV), varicella-zoster virus (VZV), Epstein-Barr virus, human herpes virus-6(HHV-6), human herpesvirus-7(HHV-7), human herpesvirus-8(HHV-8), pseudorabies and rhinotracheitis, among others.

Similarly, IL-1 is produced by activated monocytes and macrophages, and plays a role in many pathophysiological responses including rheumatoid arthritis, fever and reduction of bone resorption.

Additionally, the involvement of p38 has been implicated in stroke, Alzheimer's disease, osteoarthritis, lung injury, septic shock, angiogenesis, dermnatitis, psoriasis and atopic dermatitis. *J. Exp. Opin. Ther. Patents*, 2000, 10(1).

The role of p38 MAP kinase as a therapeutic target in oncology has been reviewed: Podar, K. H.; Teru; Chauhan, Dharminder; Anderson, Kenneth C., "Targeting signalling pathways for the treatment of multiple myeloma", *Expert Opinion on therapeutic Targets* 2005, 9, 359-381; Schultz, R. M., "Potential of p38 MAP kinase inhibitors in the treatment of cancer", *Progress in Drug Research* 2003, 60, 59-92.

The inhibition of these cytokines by inhibition of the p38 kinase is of benefit in controlling, reducing and alleviating many of these disease states.

SUMMARY

The invention provides compounds of formula Ia or Ib:

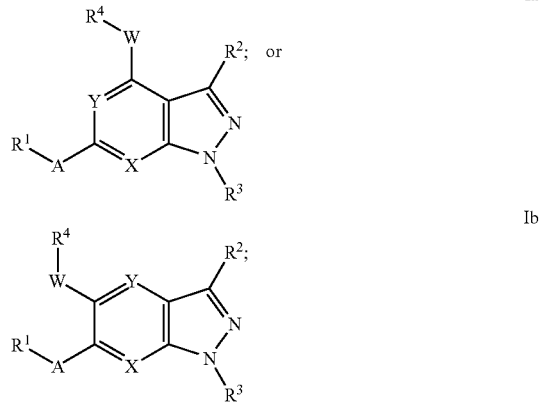

or a pharmaceutically acceptable salt thereof, wherein:

$R^1$ is aryl or heteroaryl;

$R^2$ is —$NR^iR^a$, —$NR^iSO_2R^a$, —$NR^iC(=O)R^a$, $C_{1-6}$alkylsulfonamidyl$C_{1-6}$alkyl, $C_{1-6}$alkoxycarbonylamino-$C_{1-6}$alkyl, linear $C_{3-6}$alkyl, $C_{1-6}$alkenyl, $C_{3-7}$cycloalkyl-$C_{1-4}$alkyl, $C_{3-7}$cycloalkenyl, $C_{3-7}$cycloalkenyl-$C_{1-4}$alkyl, halo-$C_{1-6}$alkyl, halo-$C_{3-7}$cycloalkyl, hydroxy-$C_{1-6}$alkyl, $C_{1-6}$alkylsulfonyl$C_{1-6}$alkyl, $C_{1-6}$-alkylsulfanyl-$C_{1-6}$alkyl, aryl-$C_{1-6}$alkyl or heteroaryl-$C_{1-6}$alkyl, wherein $R^a$ is hydrogen, $C_{1-6}$alkyl, $C_{3-7}$cycloalkyl, $C_{3-7}$cycloalkyl-$C_{1-4}$alkyl, $C_{3-7}$cycloalkenyl, $C_{3-7}$cycloalkenyl-$C_{1-4}$alkyl, halo-$C_{1-6}$alkyl, halo-$C_{3-7}$cycloalkyl, hydroxy-$C_{1-6}$ alkyl, $C_{1-6}$alkylsulfonyl$C_{1-6}$alkyl, $C_{1-6}$alkylsulfanyl-$C_{1-6}$alkyl, arylsulfonyl-$C_{1-6}$alkyl, aryl, aryl-$C_{1-6}$alkyl, heteroaryl, heteroaryl-$C_{1-6}$alkyl, $C_{1-6}$alkylsulfonamidyl$C_{1-6}$alkyl, $C_{1-6}$alkoxycarbonylamino-$C_{1-6}$alkyl, $C_{1-6}$alkoxycarbonyl-$C_{1-6}$alkyl, $C_{1-6}$alkoxyaminocarbonyl-$C_{1-6}$alkyl, aminocarbonyl-$C_{1-6}$alkyl, $C_{1-6}$alkylaminocarbonyl-$C_{1-6}$alkyl, carboxy-$C_{1-6}$alkyl, heterocyclyl, heterocyclylalkyl, $C_{1-6}$alkylcarbonyl-$C_{1-6}$alkyl, heterocyclyl-$C_{1-6}$alkyl, aryl-$C_{1-6}$alkyl, amino-$C_{1-6}$ alkyl, N—$C_{1-6}$alkylamino-$C_{1-6}$alkyl, N,N-di-$C_{1-6}$alkylamino-$C_{1-6}$alkyl, $C_{1-6}$alkoxy-$C_{1-6}$alkyl, or heteroaryl-$C_{1-6}$alkyl, and $R^i$ is hydrogen, hydroxy, or alkyl $R^3$ is hydrogen or $C_{1-6}$alkyl;

$R^4$ is hydrogen, $C_{1-6}$alkyl, hydroxy, amino, hetero-$C_{1-6}$alkyl, hetero-$C_{1-6}$alkoxy, hetero-$C_{1-6}$alkylamino, heterocyclyl, heterocyclyl-$C_{1-6}$alkyl, hydroxy$C_{3-6}$cycloalkyl, $C_{3-6}$cycloalkyl-$C_{1-6}$alkyl, $C_{1-6}$alkylsulfonyl, $C_{1-6}$alkylsulfonamido, aryl, heteroaryl, aryl-$C_{1-6}$lkyl, heteroaryl-$C_{1-6}$alkyl, $C_{1-6}$alkoxy, heteroayl-$C_{1-6}$alkoxy, —$(CHR^b)_r$—$C(=O)$—$R^c$, —$(CHR^b)_r$—O—$C(=O)$—$R^c$, —$(CHR^b)_r$—NH—$C(=O)$—$R^c$ or —$SO_2$—$R^c$, wherein $R^b$ is hydrogen, $C_{1-6}$alkyl or hetero-$C_{1-6}$alkyl;

$R^c$ is $C_{1-6}$alkyl, hydroxy, amino, hetero-$C_{1-6}$alkyl, aryl, aryl-$C_{1-6}$alkyl, heteroaryl, or heterocyclyl;

r is from 0 to 4;

X and Y are nitrogen, or one of X and Y is nitrogen and the other is $CR^d$;

wherein $R^d$ is hydrogen, $C_{1-6}$alkyl, hydroxy, $C_{1-6}$alkoxy, amino, halo-$C_{1-6}$alkyl, cyano, halo, hetero-$C_{1-6}$alkyl, C(=O)—$R^e$ or —SO$_2$—$R^e$, wherein $R^e$ is hydrogen or alkyl;

W is a bond, O, S(O)$_m$, CH$_2$ or N$R^f$;

wherein m is from 0 to 2, and $R^f$ is hydrogen, $C_{1-6}$alkyl, hetero-$C_{1-6}$alkyl, heterocyclyl, hydroxy-$C_{3-6}$cycloalkyl, —C(=O)—$R^g$ or —SO$_2$—$R^g$, wherein $R^g$ is $C_{1-6}$alkyl, aryl, aryl-$C_{1-6}$alkyl, heteroaryl, hetero-$C_{1-6}$alkyl or heterocyclyl;

$R^4$ and $R^f$ together with the atoms to which they are attached may form a heterocyclic ring;

A is O, CH$_2$, S(O)$_n$, C(=O), N$R^h$, or CH(O$R^h$), wherein m is from 0 to 2, and $R^h$ is hydrogen or $C_{1-6}$alkyl.

Another aspect of the invention provides a pharmaceutical formulation comprising one or more compounds of formula I and a pharmaceutically acceptable carrier, diluent, and/or excipient therefor.

Compounds of the invention are inhibitors of protein kinases, and exhibit effective activity against p38 in vivo. They are selective for p38 kinase relative to cyclin-dependent kinases and tyrosine kinases. Therefore, compounds of the present invention can be used for the treatment of diseases mediated by the pro-inflammatory cytokines such as TNF and IL-1. Thus, another aspect of the present invention provides a method for treating p38 mediated diseases or conditions in which a therapeutically effective amount of one or more compounds of formula I is administered to a patient.

DETALED DESCRIPTION OF THE INVENTION

All publications cited in this disclosure are incorporated herein by reference in their entirety.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means a linear saturated monovalent hydrocarbon moiety of one to six carbon atoms or a branched saturated monovalent hydrocarbon moiety of three to six carbon atoms, e.g., methyl, ethyl, propyl, 2-propyl, n-butyl, iso-butyl, tert-butyl, pentyl, and the like.

"Alkylene" means a linear saturated divalent hydrocarbon moiety of one to six carbon atoms or a branched saturated divalent hydrocarbon moiety of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylamino means a moiety of the formula —NR—R' wherein R is hyrdogen or alkyl and R' is alkyl as defined herein.

"Alkoxyamino" means a moiety of the formula —NR—OR' wherein R is hydrogen or alkyl and R' is alkyl as defined herein.

"Aminoalkyl" means a group of the formula —R—NH$_2$ wherein R is alkylene as defined herein. Exemplary aminoalkyl include amino-$C_{1-6}$alkyl selected from amino-methyl, 2-amino-ethyl, 3-amino-propyl, 2-amino-propyl, 2-amino-2-methyl-propyl, 3-amino-3-methylbutyl, 4-amino-4-methylpentyl, 2-amino-2-ethyl-propyl, 3-amino-3-ethylbutyl and 4-amino-4-ethylpentyl.

"N-Alkyl-amino-alkyl" means a group of the formula —R—NHR' wherein R is alkylene and R' is alkyl as defined herein. Exemplary N-alkyl-amino-alkyl include N-methylaminomethyl, 2-(N-methylamino)-ethyl, 3-(N-methylamino)-propyl, 2-(N-methylamino)-propyl, 2-(N-methylamino)-2-methyl-propyl, 3-(N-methylamino)-3-methylbutyl, 4-(N-methylamino)-4-methylpentyl, 2-(N-methylamino)-2-ethyl-propyl, 3-(-methylamino)-3-ethylbutyl 4-(N-methylamino)-4-ethylpentyl, N-ethylaminomethyl, 2-(N-ethylamino)-ethyl, 3-(N-ethylamino)-propyl, 2-(N-ethylamino)-propyl, 2-(N-ethylamino)-2-methyl-propyl, 3-(N-ethylamino)-3-methylbutyl, 4-(N-ethylamino)-4-methylpentyl, 2-(N-ethylamino)-2-ethyl-propyl, 3-(N-ethylamino)-3-ethylbutyl, and 4-(N-ethylamino)-4-ethylpentyl.

"N,N-Dialkyl-aminoalkyl" means a group of the formula —R—NR'R" wherein R is alkylene, and R' and R" are alkyl as defined herein. Exemplary N,N-dialkyl-aminoalkyl include N,N-dimethylaminomethyl, 2-(N,N-dimethylamino)-ethyl, 3-(N,N-dimethylamino)-propyl, 2-(N,N-dimethylamino)-propyl, 2-(N,N-dimethylamino)-2-methyl-propyl, 3-(N,N-dimethylamino)-3-methylbutyl, 4-(N,N-dimethylamino)-4-methylpentyl, 2-(N,N-dimethylamino)-2-ethyl-propyl, 3-(N,N-dimethylamino)-3-ethylbutyl 4-(N,N-dimethylamino)-4-ethylpentyl, N,N-diethylaminomethyl, 2-(N,N-diethylamino)-ethyl, 3-(N,N-diethylamino)-propyl, 2-(N,N-diethylamino)-propyl, 2-(N,N-diethylamino)-2-methyl-propyl, 3-(N,N-diethylamino)-3-methylbutyl, 4-(N,N-diethylamino)-4-methylpentyl, 2-(N,N-diethylamino)-2-ethyl-propyl, 3-(N,N-diethylamino)-3-ethylbutyl, and 4-(N,N-diethylamino)-4-ethylpentyl "Alkylsulfanyl" means a moiety of the formula —SR wherein R is alkyl as defined herein.

"Alkylsulfanylalkyl" means a moiety of the formula R'—S—R wherein R is alkyl and R' is alkylene as defined herein. Exemplary alkylsulfanylalkyl include methanesulfanylmethyl, ethylsulfanylmethyl, 2-(methanesulfanyl)-ethyl, 2-(ethylsulfanyl)-ethyl, 3-(methanesulfanyl)-propyl, 3-(ethanyl)-propyl 3-methanesulfanyl-3-methyl-butyl, 4-methanesulfanyl-butyl, and 4-methanesulfanyl-4-methyl-pentyl.

"Alkylsulfonyl" means a moiety of the formula —SO$_2$R wherein R is alkyl as defined herein.

"Alkylsulfonylalkyl" means a moiety of the formula R'—SO$_2$—R wherein R is alkyl and R' is alkylene as defined herein. Exemplary alkylsulfonylalkyl include methanesulfonylmethyl, ethylsulfonylmethyl, 2-(methanesulfonyl)-ethyl, 2-(ethylsulfonyl)-ethyl, 3-(methanesulfonyl)-propyl, 3-(ethanyl)-propyl 3-methanesulfonyl-3-methyl-butyl, 4-methanesulfonyl-butyl, and 4-methanesulfonyl-4-methyl-pentyl.

"Amino" means a group —NR'R" wherein R' and R" each independently is hydrogen or alkyl. "Amino" as used herein thus encompasses "alkylamino" and "dialkylamino".

"Alkylaminoalkyl" means a group —R—NHR' wherein R is alkylene and R' is alkyl. Alkylaminoalkyl includes methylaminomethyl, methylaminoethyl, methylaminopropyl, ethylaminoethyl and the like.

"Dialkylaminoalkyl" means a group —R—NR'R" wherein R is alkylene and R' and R" are alkyl as defined herein. Dialkylaminoalkyl includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'SO$_2$—R wherein R is alkyl and R' is hydrogen or alkyl.

"Alkylsulfonamidylalkyl" means a group of the formula —R—(NR')—SO$_2$—R" wherein R is alkylene, R' is hydrogen or alkyl, and R" is alkyl as defined herein.

"Alkoxycarbonylaminoalkyl" means a group of the formula —R—(NR')—CO—OR" wherein R is alkylene, R' is hydrogen or alkyl, and R" is alkyl as defined herein.

"Alkoxycarbonylalkyl" means a group of the formula —R—CO—OR' wherein R is alkylene and R' is alkyl as defined herein.

"Alkoxyaminocarbonylalkyl" means a group of the formula —R—CO—(NR')—OR" wherein R is alkylene, R is hydrogen or alkyl, and R" is alkyl as defined herein.

"Alkoxycarbonylalkyl" means a group of the formula —R—CO—OR wherein R is alkylene and R' is alkyl as defined herein.

"Aminocarbonylalkyl" means a group of the formula —R—CO—NH$_2$ wherein R is alkylene as defined herein.

"Alkylaminocarbonylalkyl" means a group of the formula —R—CO—NHR' wherein R is alkylene and R' is alkyl as defined herein.

"Aryl" means a monovalent monocyclic or bicyclic aromatic hydrocarbon moiety which is optionally substituted with one or more, preferably one, two or three, substituents, each of which is preferably selected from the group consisting of alkyl, hydroxy, alkoxy, haloalkyl, haloalkoxy, halo, nitro, cyano, amino, mono- and dialkylamino, methylenedioxy, ethylenedioxy, acyl, heteroalkyl, optionally substituted aryl, optionally substituted heteroaryl, optionally substituted aralkyl, and optionally substituted heteroaralkyl. A particularly preferred aryl substituent is halide. More specifically the term aryl includes, but is not limited to, phenyl, 1-naphthyl, 2-naphthyl, and the like, each of which can be substituted or unsubstituted.

"Aralkyl" refers to a moiety of the formula R—R' where R' is aryl and R is alkylene as defined herein.

"Arylsulfonylalkyl" refers to a moiety of the formula R—SO$_2$—R' where R' is aryl and R is alkylene as defined herein.

"Cycloalkyl" refers to a saturated monovalent cyclic hydrocarbon moiety of three to seven ring carbons e.g., cyclopropyl, cyclobutyl, cyclohexyl, 4-methyl-cyclohexyl, and the like. Cycloalkyl may optionally be substituted with one or more substituents, preferably one, two or three, substituents. Preferably, cycloalkyl substituent is selected from the group consisting of alkyl, hydroxy, alkoxy, haloalkyl, haloalkoxy, halo, amino, mono- and dialkylamino, heteroalkyl, acyl, aryl and heteroaryl.

"Cycloalkylalkyl" refers to a moiety of the formula —R—R' where R' is cycloalkyl and R is alkylene as defined herein.

"Cycloalkenyl" means a monovalent cyclic hydrocarbon moiety of four to seven members having at least one unsaturation (double bond).

"Cycloalkenylalkyl" is a group of the formula —R—R' wherein R is alkylene and R' is cycloalkenyl as defined herein.

"Carboxyalkyl" means a group of the formula —R—CO$_2$H wherein R is alkylene as defined herein.

"Halo", "halogen" and "halide" are used interchangeably herein and refer to fluoro, chloro, bromo, or iodo. Preferred halides are fluoro and chloro with fluoro being a particularly preferred halide.

"Haloalkyl" means alkyl substituted with one or more same or different halo atoms, e.g., —CH$_2$Cl, —CF$_3$, —CH$_2$CF$_3$, —CH$_2$CCl$_3$, and the like.

"Heteroalkyl" means an alkyl moiety as defined herein wherein one or more, preferably one, two or three, hydrogen atoms have been replaced with a substituent independently selected from the group consisting of —OR$^a$, —NR$^b$R$^c$ (where n is 0 or 1 if R$^b$ and R$^c$ are both independently alkyl, cycloalkyl or cycloalkylalkyl, and 0 if not) and —S(O)$_n$R$^d$ (where n is an integer from 0 to 2), with the understanding that the point of attachment of the heteroalkyl moiety is through a carbon atom, wherein R$^a$ is hydrogen, acyl, alkoxycarbonyl, alkyl, hydroxyalkyl, alkoxyalkyl, alkylsulfonyl, aminocarbonyl, aminosulfonylamino, cycloalkyl, or cycloalkylalkyl; R$^b$ and R$^c$ are independently of each other hydrogen, acyl, alkoxycarbonyl, aminocarbonyl, aminocarbonyl, aminosulfonylamino, hydroxyalkyl, alkoxyalkyl, alkylsulfonyl, cycloalkyl, cycloalkylalkyl, alkylsulfonyl, aminosulfonyl, mono- or di-alkylaminosulfonyl, aminoalkyl, mono- or di-alkylaminoalkyl, hydroxyalkyl, alkoxyalkyl, hydroxyalkylsulfonyl or alkoxyalkylsulfonyl; and when n is 0, R$^d$ is hydrogen, alkyl, cycloalkyl, cycloalkylalkyl, or aryl, and when n is 1 or 2, R$^d$ is alkyl, cycloalkyl, cycloalkylalkyl, hydroxyalkyl, alkoxyalkyl, alkylamino, aminocarbonyl, aminosulfonylamino, alkylsulfonyl, amino, or optionally substituted phenyl. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like. Accordingly, hydroxyalkyl and alkoxyalkyl are subset of heteroalkyl.

"Heteroaryl" means a monovalent monocyclic or bicyclic moiety of 5 to 12 ring atoms having at least one aromatic ring containing one, two, or three ring heteroatoms selected from N, O, or S (preferably N or O), the remaining ring atoms being C, with the understanding that the attachment point of the heteroaryl moiety will be on an aromatic ring. The heteroaryl ring is optionally substituted independently with one or more substituents, preferably one, two or three substituents, each of which is independently selected from alkyl, haloalkyl, hydroxy, alkoxy, halo, nitro and cyano. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, imidazo[2,1-b]thiazolyl, and the derivatives thereof.

"Heteroarylalkyl" refers to a moiety of the formula $Ar^z$—$R^y$—, where $Ar^z$ is heteroaryl and $R^y$ is alkylene as defined herein.

"Heterocyclyl" means a saturated or unsaturated non-aromatic cyclic moiety of 3 to 8 ring atoms in which one or two ring atoms are heteroatoms selected from N, O, or $S(O)_n$ (where n is an integer from 0 to 2), preferably N or O, the remaining ring atoms being C, where one or two C atoms may optionally be replaced by a carbonyl group. The heterocyclyl ring may be optionally substituted independently with one or more, preferably one, two, or three, substituents, each of which is independently selected from alkyl, haloalkyl, hydroxyalkyl, halo, nitro, cyano, cyanoalkyl, hydroxy, alkoxy, amino, mono- and dialkylamino, aralkyl, —$(X)_n$—$C(O)R^e$ (where X is O or $NR^f$, n is 0 or 1, $R^e$ is hydrogen, alkyl, haloalkyl, hydroxy (when n is 0), alkoxy, amino, mono- and dialkylamino, or optionally substituted phenyl, and $R^f$ is H or alkyl), -alkylene-$C(O)R^g$ (where $R^g$ is alkyl, —$OR^h$ or $NR^iR^j$ and $R^h$ is hydrogen, alkyl or haloalkyl, and $R^i$ and $R^j$ are independently hydrogen or alkyl), and —$S(O)_nR^k$ (where n is an integer from 0 to 2) such that when n is 0, $R^k$ is hydrogen, alkyl, cycloalkyl, or cycloalkylalkyl, and when n is 1 or 2, $R^k$ is alkyl, cycloalkyl, cycloalkylalkyl, amino, acylamino, monoalkylamino, or dialkylamino. A particularly preferred group of heterocyclyl substituents include alkyl, haloalkyl, hydroxyalkyl, halo, hydroxy, alkoxy, amino, mono- and dialkylamino, aralkyl, and —$S(O)_nR^k$. In particular, the term heterocyclyl includes, but is not limited to, tetrahydrofuranyl, pyridinyl, tetrahydropyranyl, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, 4-(1,1-dioxo-tetrahydro-2H-thiopyranyl), pyrrolinyl, im idazolinyl, N-methanesulfonyl-piperidin-4-yl, and the derivatives thereof, each of which may be optionally substituted.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxyalkyl" refers to a subset of heteroalkyl and refers in particular to an alkyl moiety as defined herein that is substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl.

"Hydroxycycloalkyl" refers to a subset of cycloalkyl moiety as defined herein and specifically refers to a cycloalkyl moiety as defined herein where one or more, preferably one, two or three, hydrogen atoms in the cycloalkyl moiety have been replaced with a hydroxy substituent. Representative examples include, but are not limited to, 2-, 3-, or 4-hydroxycyclohexyl, and the like.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Optionally substituted", when used in association with "aryl", phenyl", "heteroaryl" "cycloalkyl" or "heterocyclyl", means an aryl, phenyl, heteroaryl, cycloalkylyl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —$(CR'R")_n$—COOR (where n is an integer from 0 to 5, R' and R" are independently hydrogen or alkyl, and R is hydrogen, alkyl, cycloalkyl, cycloalkylalkyl, phenyl or phenylalkyl), or —$(CR'R")_n$—$CONR^aR^b$ (where n is an integer from 0 to 5, R' and R" are independently hydrogen or alkyl, and $R^a$ and $R^b$ are, independently of each other, hydrogen, alkyl, cycloalkyl, cycloalkylalkyl, phenyl or phenylalkyl), or as provided herein elsewhere.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Protecting group" refers to a grouping of atoms that when attached to a reactive group in a molecule masks, reduces or prevents that reactivity. Examples of protecting groups can be found in T. W. Green and P. G. Futs, *Protective Groups in Organic Chemistry*, (Wiley, 2nd ed. 1991) and Harrison and Harrison et al., *Compendium of Synthetic Organic Methods,*

Vols. 1-8 (John Wiley and Sons, 1971-1996). Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

As used herein, the terms "those defined above" and "those defined herein" are used interchangeably herein and, when referring to a variable, incorporates by reference the broad definition of the variable as well as preferred, more preferred and most preferred definitions, if any.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

The terms "those defined above" and "those defined herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen. Where a chiral center is present in a structure but no specific enantiomer is shown, the structure encompasses both enantiomers associated with the chiral center.

Compounds of the Invention

The invention provides compounds of formula Ia or Ib:

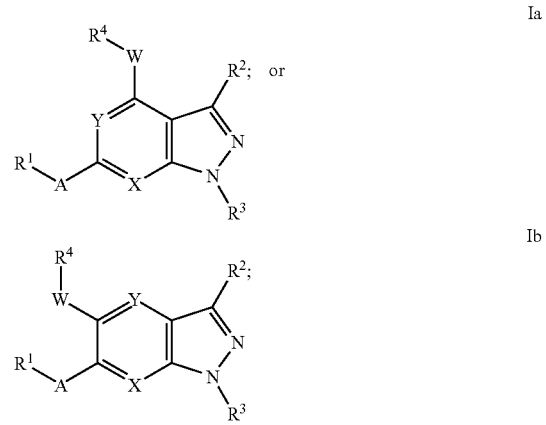

or a pharmaceutically acceptable salt thereof, wherein:

$R^1$ is aryl or heteroaryl;

$R^2$ is —$NR^iR^a$, —$NR^iSO_2R^a$, —$NR^iC(=O)R^a$, $C_{1-6}$alkylsulfonamidylC$_1$alkyl, $C_{1-6}$alkoxycarbonylamino-$C_{1-6}$alkyl, linear $C_{3-6}$alkyl, $C_{1-6}$alkenyl, $C_{3-7}$cycloalkyl-$C_{1-4}$alkyl, $C_{3-7}$cycloalkenyl, $C_{3-7}$cycloalkenyl-$C_{1-4}$alkyl, halo-$C_{1-6}$alkyl, halo-$C_{3-7}$cycloalkyl, hydroxy-$C_{1-6}$alkyl, $C_{1-6}$alkylsulfonylC$_{1-6}$alkyl, $C_{1-6}$alkylsulfanyl-$C_{1-6}$alkyl, aryl-$C_{1-6}$alkyl or heteroaryl-$C_{1-6}$alkyl, wherein $R^a$ is hydrogen, $C_{1-6}$alkyl, $C_{3-7}$cycloalkyl, $C_{3-7}$cycloalkyl-$C_{1-4}$alkyl, $C_{3-7}$cycloalkenyl, $C_{3-7}$cycloalkenyl-$C_{1-4}$alkyl, halo-$C_{1-6}$alkyl, halo-$C_{3-7}$cycloalkyl, hydroxy-$C_{1-6}$ alkyl, $C_{1-6}$alkylsulfonylC$_{1-6}$alkyl, $C_{1-6}$alkylsulfanyl-$C_{1-6}$alkyl, arylsulfonyl-$C_{1-6}$alkyl, aryl, aryl-$C_{1-6}$alkyl, heteroaryl, heteroaryl-$C_{1-6}$alkyl, $C_{1-6}$alkylsulfonamidyl$C_{1-6}$alkyl, $C_{1-6}$alkoxycarbonylamino-$C_{1-6}$alkyl, $C_{1-6}$alkoxycarbonyl-$C_{1-6}$alkyl, $C_{1-6}$alkoxyaminocarbonyl-$C_{1-6}$alkyl, aminocarbonyl-$C_{1-6}$alkyl, $C_{1-6}$-alkylaminocarbonyl-$C_{1-6}$alkyl, carboxy-$C_{1-6}$alkyl, heterocyclyl, heterocyclylalkyl, $C_{1-6}$alkylcarbonyl-$C_{1-6}$alkyl, heterocyclyl-$C_{1-6}$alkyl, aryl-$C_{1-6}$alkyl, amino-$C_{1-6}$alkyl, N—$C_{1-6}$alkylamino-$C_{1-6}$alkyl, N,N-di-$C_{1-6}$alkylamino-$C_{1-6}$alkyl, $C_{1-6}$alkoxy-$C_{1-6}$alkyl, or heteroaryl-$C_{1-6}$alkyl, and $R^i$ is hydrogen, hydroxy, or alkyl $R^3$ is hydrogen or $C_{1-6}$alkyl;

$R^4$ is hydrogen, $C_{1-6}$alkyl, hydroxy, amino, hetero-$C_{1-6}$alkyl, hetero-$C_{1-6}$alkoxy, hetero-$C_{1-6}$alkylamino, heterocyclyl, heterocyclyl-$C_{1-6}$alkyl, hydroxy$C_{3-6}$cycloalkyl, $C_{3-6}$cycloalkyl-$C_{1-6}$alkyl, $C_{1-6}$alkylsulfonyl, $C_{1-6}$alkylsulfonamido, aryl, heteroaryl, aryl-$C_{1-6}$lkyl, heteroaryl-$C_{1-6}$alkyl, $C_{1-6}$alkoxy, heteroayl-$C_{1-6}$alkoxy, —(CHR$^b$)$_r$—C(=O)—R$^c$, —(CHR$^b$)$_r$—O—C(=O)—R$^c$, —(CHR$^b$)$_r$—NH—C(=O)—R$^c$ or —SO$_2$R$^c$, wherein $R^b$ is hydrogen, $C_{1-6}$alkyl or hetero-$C_{1-6}$alkyl;

$R^c$ is $C_{1-6}$alkyl, hydroxy, amino, hetero-$C_{1-6}$alkyl, aryl, aryl-$C_{1-6}$alkyl, heteroaryl, or heterocyclyl;

r is from 0 to 4;

X and Y are nitrogen, or one of X and Y is nitrogen and the other is CR$^d$;

wherein $R^d$ is hydrogen, $C_{1-6}$alkyl, hydroxy, $C_{1-6}$alkoxy, amino, halo-$C_{1-6}$alkyl, cyano, halo, hetero-$C_{1-6}$alkyl, C(=O)—R$^e$ or —SO$_2$—R$^e$, wherein $R^e$ is hydrogen or alkyl;

W is a bond, O, S(O)$_m$, CH$_2$ or NR$^f$;

wherein m is from 0 to 2, and $R^f$ is hydrogen, $C_{1-6}$alkyl, hetero-$C_{1-6}$alkyl, heterocyclyl, hydroxy-$C_{3-6}$cycloalkyl, —C(=O)—R$^g$ or —SO$_2$—R$^g$, wherein $R^g$ is $C_{1-6}$alkyl, aryl, aryl-$C_{1-6}$alkyl, heteroaryl, hetero-$C_{1-6}$alkyl or heterocyclyl;

or $R^4$ and $R^f$ together with the atoms to which they are attached may form a heterocyclic ring;

A is O, CH$_2$, S(O)$_n$, C(=O), NR$^h$, or CH(OR$^h$), wherein m is from 0 to 2, and $R^h$ is hydrogen or $C_{1-6}$alkyl.

In certain embodiments of either formula Ia or Ib, $R^3$ is hydrogen.

In certain embodiments of either formula Ia or Ib, $R^i$ is hydrogen.

In certain embodiments of either formula Ia or Ib, X and Y are nitrogen.

In certain embodiments of either formula Ia or Ib, X is nitrogen and Y is CR$^d$.

In certain embodiments of either formula Ia or Ib, X is CR$^d$ and Y is nitrogen.

In certain embodiments of either formula Ia or Ib, A is O, S or NR$^i$.

In certain embodiments of either formula Ia or Ib, $R^1$ is optionally substituted phenyl.

In certain embodiments of either formula Ia or Ib, $R^1$ is 2-halophenyl or 2,4-dihalophenyl.

In certain embodiments of either formula Ia or Ib, W is NR$^f$ or O and $R^4$ is heteroalkyl.

In certain embodiments of either formula Ia or Ib, W is a bond and $R^4$ is hydrogen.

In certain embodiments of either formula Ia or Ib, A is O.

In certain embodiments of either formula Ia or Ib, $R^2$ is —NHR$^a$, —NHSO$_2$R$^a$, —NHC(=O)R$^a$, $C_{1-6}$alkenyl, $C_{3-7}$cycloalkyl-$C_{1-4}$alkyl, $C_{3-7}$cycloalkenyl, $C_{3-7}$cycloalkenyl-$C_{1-4}$alkyl, halo-$C_{3-7}$cycloalkyl, $C_{1-6}$alkylsulfonyl$C_{1-6}$alkyl, $C_{1-6}$alkylsulfanyl-$C_{1-6}$alkyl, aryl-$C_{1-6}$alkyl or heteroaryl-$C_{1-6}$alkyl.

In certain embodiments of either formula Ia or Ib, $R^2$ is —NHR$^a$, —NHSO$_2$R$^a$, —NHC(=O)R$^a$, $C_{1-6}$alkenyl, $C_{3-7}$cycloalkyl-$C_{1-4}$alkyl, $C_{3-7}$cycloalkenyl or $C_{3-7}$cycloalkenyl-$C_{1-4}$alkyl.

In certain embodiments of either formula Ia or Ib, $R^2$ is —NHR$^a$, —NHSO$_2$R$^a$, or —NHC(=O)R$^a$.

In certain embodiments of either formula Ia or Ib, $R^2$ is —NHR$^a$.

In certain embodiments of either formula Ia or Ib, $R^2$ is —NHSO$_2$R$^a$.

In certain embodiments of either formula Ia or Ib, $R^2$ is —NHC(=O)R$^a$.

In certain embodiments of either formula Ia or Ib, $R^a$ is $C_{1-6}$alkyl, $C_{3-7}$cycloalkyl, $C_{3-7}$cycloalkyl-$C_{1-4}$alkyl, $C_{3-7}$cycloalkenyl, $C_{3-7}$cycloalkenyl-$C_{1-4}$alkyl, $C_{1-6}$alkylsulfonyl$C_{1-6}$ alkyl, aryl or heteroaryl.

In certain embodiments of either formula Ia or Ib, $R^a$ is $C_{1-6}$alkyl, $C_{3-7}$cycloalkyl, $C_{3-7}$cycloalkyl-$C_{1-4}$alkyl, or $C_{1-6}$alkylsulfonyl$C_{1-6}$alkyl.

In certain embodiments of either formula Ia or Ib, $R^a$ is isopropyl, tert-butyl, thienyl, furanyl, pyridinyl, thienylmethyl, furanylmethyl, pyridinymethyl, cyclopropyl, cyclobutyl, cyclopentyl, cyclohexyl, cyclopropylmethyl, cyclobutylmethyl, cyclopentylmethyl, cyclohexylnethyl, optionally substituted phenyl, cyclopentenyl optionally substituted with hydroxy, cyclohexenyl optionally substituted with hydroxy, cyclopentenylmethyl optionally substituted with hydroxy, cyclohexenylmethyl optionally substituted with hydroxy, piperidinyl optionally substituted at the 1-position, tetrahydropyranyl, tetrahydrofuranyl, tetrahydropyranylmethyl, tetrahydrofuranylmethyl, 1-butene-4-yl optionally substituted once or twice with methyl, 2-methanesulfonyl-1-methylethyl, 2-methanesulfonyl-ethyl, 3-methanesulfonyl-propyl, 3-methanesulfonyl-1-methyl-propyl, 3-methanesulfonyl-2-methyl-propyl, 2-ethanesulfonyl-1-methyl-ethyl or 1-methanesulfonylmethyl-propyl.

In certain embodiments of either formula Ia or Ib, $R^a$ is $C_{1-6}$alkylsulfonyl$C_{1-6}$-alkyl selected from 2-methanesulfonyl-1-methyl-ethyl, 2-methanesulfonyl-ethyl, 3-methanesulfonyl-propyl, 3-methanesulfonyl-1-methyl-propyl, 3-methanesulfonyl-2-methyl-propyl, 2-ethanesulfonyl-1-methyl-ethyl and 1-methanesulfonylmethyl-propyl.

In certain embodiments of either formula Ia or Ib, $R^2$ is —NHR$^a$ and $R^a$ is $C_{1-6}$alkylsulfonyl$C_{1-6}$alkyl.

In certain embodiments of formula Ia, A is O, X and Y are N, and $R^1$ is 2-halophenyl or 2,4-dihalophenyl.

In certain embodiments of formula I a, A is O, X and Y are N, $R^1$ is 2-halophenyl or 2,4-dihalophenyl, and $R^2$ is —NHR$^a$, —NHSO$_2$R$^a$, —NHC(=O)R$^a$, $C_{1-6}$alkenyl, $C_{3-7}$cycloalkyl-$C_{1-4}$alkyl, $C_{3-7}$cycloalkenyl or $C_{3-7}$cycloalkenyl-$C_{1-4}$alkyl.

In certain embodiments of formula I , A is O, X and Y are N, $R^1$ is 2-halophenyl or 2,4-dihalophenyl, $R^2$ is —NHR$^a$, —NHSO$_2$R$^a$, —NHC(=O)R$^a$, $C_{1-6}$alkenyl, $C_{3-7}$cycloalkyl-$C_{1-4}$alkyl, $C_{3-7}$cycloalkenyl or $C_{3-7}$cycloalkenyl-$C_{1-4}$alkyl, and $R^a$ is $C_{1-6}$alkyl, $C_{3-7}$cycloalkyl, $C_{3-7}$cycloalkyl-$C_{1-4}$ alkyl, $C_{3-7}$cycloalkenyl, $C_{3-7}$cycloalkenyl-$C_{1-4}$alkyl, $C_{1-6}$alkylsulfonyl$C_{1-6}$alkyl, aryl or heteroaryl.

In certain embodiments of formula Ia, A is O, X and Y are N, R$^1$ is 2-halophenyl or 2,4-dihalophenyl, W is a bond, R$^4$ is hydrogen, R$^2$ is —NHR$^a$, —NHSO$_2$R$^a$, —NHC(═O)R$^a$, C$_{1-6}$alkenyl, C$_{3-7}$cycloalkyl-C$_{1-4}$alkyl, C$_{3-7}$cycloalkenyl or C$_{3-7}$cycloalkenyl-C$_{1-4}$alkyl, and R$^a$ is C$_{1-6}$alkyl, C$_{3-7}$cycloalkyl, C$_{3-7}$cycloalkyl-C$_{1-4}$alkyl, C$_{3-7}$cycloalkenyl, C$_{3-7}$cycloalkenyl-C$_{1-4}$alkyl, C$_{1-6}$-alkylsulfonylC$_{1-6}$alkyl, aryl or heteroaryl.

In certain embodiments of formula Ia, A is O, X and Y are N, R$^1$ is 2-halophenyl or 2,4-dihalophenyl, W is a bond, R$^4$ is hydrogen, and R$^2$ is NHR$^a$, —NHSO$_2$R$^a$ or —NHC(═O)R$^a$, and R$^a$ is isopropyl, tert-butyl, thienyl, furanyl, pyridinyl, thienylmethyl, furanylmethyl, pyridinymethyl, cyclopropyl, cyclobutyl, cyclopentyl, cyclohexyl, cyclopropylmethyl, cyclobutylmethyl, cyclopentylmethyl, cyclohexylnethyl, optionally substituted phenyl, cyclopentenyl optionally substituted with hydroxy, cyclohexenyl optionally substituted with hydroxy, cyclopentenylmethyl optionally substituted with hydroxy, cyclohexenylmethyl optionally substituted with hydroxy, piperidinyl optionally substituted at the 1-position, tetrahydropyranyl, tetrahydrofuranyl, tetrahydropyranylmethyl, tetrahydrofuranylmethyl, 1-butene-4-yl optionally substituted once or twice with methyl, 2-methanesulfonyl-1-methyl-ethyl, 2-methanesulfonyl-ethyl, 3-methanesulfonyl-propyl, 3-methanesulfonyl-1-methyl-propyl, 3-methanesulfonyl-2-methyl-propyl, 2-ethanesulfonyl-1-methyl-ethyl or 1-methanesulfonylmethyl-propyl.

In certain embodiments of formula Ia, A is O, X and Y are N, R$^1$ is 2-halophenyl or 2,4-dihalophenyl, and R$^2$ is —NHR$^a$.

In certain embodiments of formula Ia, A is O, X and Y are N, R$^1$ is 2-halophenyl or 2,4-dihalophenyl, W is a bond, R$^4$ is hydrogen, R$^2$ is NHR$^a$, and R$^a$ is C$_{1-6}$alkyl, C$_{3-7}$cycloalkyl, C$_{3-7}$cycloalkyl-C$_{1-4}$alkyl, C$_{3-7}$cycloalkenyl, C$_{3-7}$cycloalkenyl-C$_{1-4}$alkyl, halo-C$_{1-6}$alkyl, halo-C$_{3-7}$cycloalkyl, hydroxy-C$_{1-6}$alkyl, C$_{1-6}$alkylsulfonylC$_{1-6}$alkyl, C$_{1-6}$alkylsulfanyl-C$_{1-6}$alkyl, arylsulfonyl-C$_{1-6}$alkyl, aryl, aralkyl, heteroaryl, heteroaralkyl, C$_{1-6}$alkylsulfonamidylC$_{1-6}$alkyl, C$_{1-6}$alkoxycarbonylamino-C$_{1-6}$alkyl, C$_{1-6}$alkoxycarbonyl-C$_{1-6}$alkyl, C$_{1-6}$alkoxyaminocarbonyl-C$_{1-6}$alkyl, aminocarbonyl-C$_{1-6}$alkyl, C$_{1-6}$-alkylaminocarbonyl-C$_{1-6}$alkyl, carboxy-C$_{1-6}$alkyl, heterocyclyl, heterocyclylalkyl, C$_{1-6}$alkylcarbonyl-C$_{1-6}$alkyl, heterocyclyl-C$_{1-6}$alkyl, aryl-C$_{1-6}$alkyl, amino-C$_{1-6}$alkyl, N—C$_{1-6}$alkylamino-C$_{1-6}$alkyl, N,N-di-C$_{1-6}$alkylamino-C$_{1-6}$alkyl, or heteroaryl-C$_{1-6}$alkyl.

In certain embodiments of formula Ia, A is O, X and Y are N, R$^1$ is 2-halophenyl or 2,4-dihalophenyl, W is a bond, R$^4$ is hydrogen, R$^2$ is NHR$^a$, and R$^a$ is C$_{1-6}$alkyl, C$_{3-7}$cycloalkyl-C$_{1-4}$alkyl, hydroxy-C$_{1-6}$alkyl, C$_{1-6}$alkylsulfonylC$_{1-6}$alkyl, C$_{1-6}$alkylsulfanyl-C$_{1-6}$alkyl, arylsulfonyl-C$_{1-6}$alkyl, heterocyclyl, heteroaryl-C$_{1-6}$alkyl or heterocyclyl-C$_{1-6}$alkyl.

In certain embodiments of formula Ia, A is O, X and Y are N, R$^1$ is 2-halophenyl or 2,4-dihalophenyl, W is a bond, R$^4$ is hydrogen, R$^2$ is NHR$^a$, and R$^a$ is C$_{1-6}$alkyl, C$_{3-7}$cycloalkyl, or C$_{1-6}$alkylsulfonyl-C$_{1-6}$alkyl.

In certain embodiments of formula Ia, A is O, X and Y are N, R$^1$ is 2-halophenyl or 2,4-dihalophenyl, W is a bond, R$^4$ is hydrogen, R$^2$ is NHR$^a$, and R$^a$ is heterocyclyl selected from tetrahydropyranyl, tetrahydrothiopyranyl, tetrahydrothiophenyl and piperidinyl.

In certain embodiments of formula Ia, A is O, X and Y are N, R$^1$ is 2-halophenyl or 2,4-dihalophenyl, W is a bond, R$^4$ is hydrogen, R$^2$ is NHR$^a$, and R$^a$ is heterocyclyl selected from tetrahydropyran-4-yl, tetrahydro-thiopyran-3-yl, 1,1-dioxo-hexahydro-1lambda*6*-thiopyran-3-yl, 1,1-dioxo-hexahydro-1lambda*6*-thiopyran-4-yl, 1,1-dioxo-tetrahydro-1lambda*6*-thiophen-3-yl, piperidin-4-yl and 1-acetyl-piperidin-4-yl.

In certain embodiments of formula Ia, A is O, X and Y are N, R$^1$ is 2-halophenyl or 2,4-dihalophenyl, W is a bond, R$^4$ is hydrogen, R$^2$ is NHR$^a$, and R$^a$ is heteroaryl-C$_{1-6}$alky selected from tetrazolyl-C$_{1-6}$alkyl and triazolyl-C$_{1-6}$alkyl.

In certain embodiments of formula Ia, A is O, X and Y are N, R$^1$ is 2-halophenyl or 2,4-dihalophenyl, W is a bond, R$^4$ is hydrogen, R$^2$ is NHR$^a$, and R$^a$ is heteroarylC$_{1-6}$alky selected from 1-methyl-2-tetrazol-2-yl-ethyl and 1-methyl-2-[1,2,3]triazol-2-yl-ethyl.

In certain embodiments of formula Ia, A is O, X and Y are N, R$^1$ is 2-halophenyl or 2,4-dihalophenyl, W is a bond, R$^4$ is hydrogen, R$^2$ is NHR$^a$, and R$^a$ is heterocyclyl-C$_{1-6}$alkyl selected from pyrrolidin-C$_{1-6}$alkyl and tetrahydrothiophen-C$_{1-6}$alkyl.

In certain embodiments of formula Ia, A is O, X and Y are N, R$^1$ is 2-halophenyl or 2,4-dihalophenyl, W is a bond, R$^4$ is hydrogen, R$^2$ is NHR$^a$, and R$^a$ is heterocyclyl-C$_{1-6}$alkyl selected from pyrrolidin-2-ylmethyl, tetrahydro-thiophen-2-ylmethyl, 1,1-dioxo-tetrahydro-1lambda*6*-thiophen-2-ylmethyl, 1-methanesulfonyl-pyrrolidin-2-ylmethyl, 1-methoxycarbonyl-pyrrolidin-2-ylmethyl and (1,1-dioxo-tetrahydro-1lambda*6*-thiophen-3-ylmethyl.

In certain embodiments of formula Ia, A is O, X and Y are N, R$^1$ is 2-halophenyl or 2,4-dihalophenyl, W is a bond, R$^4$ is hydrogen, R$^2$ is NHR$^a$, and R$^a$ is cyclohexyl or cyclopentyl substituted with C$_{1-6}$alkylsulfonyl.

In certain embodiments of formula Ia, A is O, X and Y are N, R$^1$ is 2-halophenyl or 2,4-dihalophenyl, W is a bond, R$^4$ is hydrogen, R$^2$ is NHRR, and R$^a$ is C$_{1-6}$-alkylsulfonylC$_{1-6}$alkyl.

In certain embodiments of formula Ia, A is O, X and Y are N, R$^1$ is 2-halophenyl or 2,4-dihalophenyl, W is a bond, R$^4$ is hydrogen, R$^2$ is NHR$^a$, and R$^a$ is 2-methanesulfonyl-cyclopentyl.

In certain embodiments of formula Ia, A is O, X and Y are N, R$^1$ is 2-halophenyl or 2,4-dihalophenyl, W is a bond, R$^4$ is hydrogen, R$^2$ is NHR$^a$, and R$^a$ is isopropyl or isobutyl.

In certain embodiments of formula Ia, A is O, X and Y are N, R$^1$ is 2-halophenyl or 2,4-dihalophenyl, W is a bond, R$^4$ is hydrogen, R$^2$ is NHR$^a$, and R$^a$ is 2-methanesulfonyl-1-methyl-ethyl, 2-methanesulfonyl-ethyl, 3-methanesulfonyl-propyl, 3-methanesulfonyl-1-methyl-propyl, 3-methanesulfonyl-2-methyl-propyl, 2-ethanesulfonyl-1-methyl-ethyl or 1-methanesulfonylmethyl-propyl.

In certain embodiments of formula Ia, A is O, X and Y are N, R$^1$ is 2-halophenyl or 2,4-dihalophenyl, W is a bond, R$^4$ is hydrogen, R$^2$ is NHR$^a$, and R$^a$ is 2-methanesulfonyl-1-methyl-ethyl.

In certain embodiments of formula Ia, A is O, X and Y are N, R$^1$ is 2-halophenyl or 2,4-dihalophenyl, W is a bond, R$^4$ is hydrogen, R$^2$ is NHR$^a$, and R$^a$ is isopropyl.

In certain embodiments of formula Ia, A is O, X and Y are N, R$^1$ is 2-halophenyl or 2,4-dihalophenyl, W is a bond, R$^4$ is hydrogen, R$^2$ is NHR$^a$, and R$^a$ is (R)-2-methanesulfonyl-1-methyl-ethyl.

In certain embodiments of formula Ia, A is O, X and Y are N, R$^1$ is 2-halophenyl or 2,4-dihalophenyl, W is a bond, R$^4$ is hydrogen, R$^2$ is NHR$^a$, and R$^a$ is (S)-2-methanesulfonyl-1-methyl-ethyl.

In certain embodiments of formula Ib, A is O, X is N, Y is CH, R$^1$ is 2-halophenyl or 2,4-dihalophenyl, W is a bond, R$^4$ is hydrogen, R$^2$ is NHR$^a$, and R$^a$ is C$_{1-6}$alkylsulfonylC$_{1-6}$alkyl.

In certain embodiments of formula Ib, A is O, X is N, Y is CH, $R^1$ is 2-halophenyl or 2,4-dihalophenyl, W is a bond, $R^4$ is hydrogen, $R^2$ is $NHR^a$, and $R^a$ is 2-methanesulfonyl-1-methyl-ethyl.

In certain embodiments of formula Ib, A is O, X is N, Y is CH, $R^1$ is 2-halophenyl or 2,4-dihalophenyl, W is a bond, $R^4$ is hydrogen, $R^2$ is $NHR^a$, and $R^a$ is (R)-2-methanesulfonyl-1-methyl-ethyl.

In certain embodiments of formula Ib, A is O, X is N, Y is CH, $R^1$ is 2-halophenyl or 2,4-dihalophenyl, W is a bond, $R^4$ is hydrogen, $R^2$ is $NHR^a$, and $R^a$ is (S)-2-methanesulfonyl-1-methyl-ethyl.

In certain embodiments of formula Ib, A is O, Y is N, X is CH, $R^1$ is 2-halophenyl or 2,4-dihalophenyl, W is a bond, $R^4$ is hydrogen, $R^2$ is $NHR^a$, and $R^a$ is 2-methanesulfonyl-1-methyl-ethyl.

In certain embodiments of formula Ib, A is O, Y is N, X is CH, $R^1$ is 2-halophenyl or 2,4-dihalophenyl, W is a bond, $R^4$ is hydrogen, $R^2$ is $NHR^a$, and $R^a$ is isopropyl.

In certain embodiments of formula Ib, A is O, Y is N, X is CH, $R^1$ is 2-halophenyl or 2,4-dihalophenyl, W is a bond, $R^4$ is hydrogen, $R^2$ is $NHR^a$, and $R^a$ is (R)-2-methanesulfonyl-1-methyl-ethyl.

In certain embodiments of formula Ib, A is O, Y is N, X is CH, $R^1$ is 2-halophenyl or 2,4-dihalophenyl, W is a bond, $R^4$ is hydrogen, $R^2$ is $NHR^a$, and $R^a$ is (S)-2-methanesulfonyl-1-methyl-ethyl.

In certain embodiments of formula Ia, the subject compounds may be of formula II:

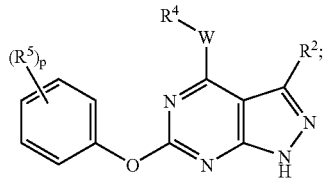

wherein:

p is from 0 to 4;

each $R^5$ is independently halo, alkyl, alkoxy, haloalkyl, haloalkoxy or cyano; and W, $R^2$ and $R^4$ are as defined herein.

In certain embodiments of formula II, p is 1 or 2 and $R^5$ is halo, preferably fluoro.

In certain embodiments of formula II, W is $NR^f$ or O and $R^4$ is heteroalkyl.

In certain embodiments of formula II, W is a bond and $R^4$ is hydrogen.

In certain embodiments of formula II, $R^2$ is —$NHR^a$, —$NHSO_2R^a$, —$NHC(=O)R^a$, $C_{1-6}$alkenyl, $C_{3-7}$cycloalkyl-$C_{1-4}$alkyl, $C_{3-7}$cycloalkenyl, $C_{3-7}$cycloalkenyl-$C_{1-4}$alkyl, halo-$C_{3-7}$cycloalkyl, $C_{1-6}$alkylsulfonyl$C_{1-6}$alkyl, $C_{1-6}$alkylsulfanyl-$C_{1-6}$alkyl, aryl-$C_{1-6}$alkyl or heteroaryl-$C_{1-6}$alkyl.

In certain embodiments of formula II, $R^2$ is —$NHR^a$, —$NHSO_2R^a$, —$NHC(=O)R^a$, $C_{1-6}$alkenyl, $C_{3-7}$cycloalkyl-$C_{1-4}$alkyl, $C_{3-7}$cycloalkenyl-$C_{1-4}$alkyl, halo-$C_{3-7}$cycloalkyl, $C_{1-6}$alkenyl, $C_{3-7}$cycloalkyl-$C_{1-5}$alkyl, $C_{3-7}$cycloalkenyl or $C_{3-7}$cycloalkenyl-$C_{1-4}$alkyl.

In certain embodiments of formula II, $R^2$ is —$NHR^a$, —$NHSO_2R^a$, or —$NHC(=O)R^a$.

In certain embodiments of formula II, $R^2$ is —$NHR^a$.

In certain embodiments of formula II, $R^2$ is —$NHSO_2R^a$.

In certain embodiments of formula II, $R^2$ is —$NHC(=O)R^a$.

In certain embodiments of formula II, $R^a$ is $C_{1-6}$alkyl, $C_{3-7}$cycloalkyl, $C_{3-7}$cycloalkyl-$C_{1-4}$alkyl, $C_{3-7}$cycloalkenyl, $C_{3-7}$cycloalkenyl-$C_{1-4}$alkyl, $C_{1-6}$alkylsulfonyl$C_{1-6}$alkyl, aryl or heteroaryl.

In certain embodiments of formula II, $R^a$ is $C_{1-6}$alkyl, $C_{3-7}$cycloalkyl, $C_{3-7}$cycloalkyl-$C_{1-4}$alkyl, or $C_{1-6}$alkylsulfonyl$C_{1-6}$alkyl.

In certain embodiments of formula II, $R^a$ is isopropyl, tert-butyl, thienyl, furanyl, pyridinyl, thienylmethyl, furanylmethyl, pyridinylmethyl, cyclopropyl, cyclobutyl, cyclopentyl, cyclohexyl, cyclopropylmethyl, cyclobutylmethyl, cyclopentylmethyl, cyclohexylnethyl, optionally substituted phenyl, cyclopentenyl optionally substituted with hydroxy, cyclohexenyl optionally substituted with hydroxy, cyclopentenylmethyl optionally substituted with hydroxy, cyclohexenylmethyl optionally substituted with hydroxy, piperidinyl optionally substituted at the 1-position, tetrahydropyranyl, tetrahydrofuranyl, tetrahydropyranylmethyl, tetrahydrofuranylmethyl, 1-butene-4-yl optionally substituted once or twice with methyl, 2-methanesulfonyl-1-methyl-ethyl, 2-methanesulfonyl-ethyl, 3-methanesulfonyl-propyl, 3-methanesulfonyl-1-methyl-propyl, 3-methanesulfonyl-2-methyl-propyl, 2-ethanesulfonyl-1-methyl-ethyl and 1-methanesulfonylmethyl-propyl.

In certain embodiments of formula II, $R^a$ is $C_{1-6}$alkylsulfonyl$C_{1-6}$alkyl selected from 2-methanesulfonyl-1-methyl-ethyl, 2-methanesulfonyl-ethyl, 3-methanesulfonyl-propyl, 3-methanesulfonyl-1-methyl-propyl, 3-methanesulfonyl-2-methyl-propyl, 2-ethanesulfonyl-1-methyl-ethyl and 1-methanesulfonylmethyl-propyl.

In certain embodiments of formula II, p is 1 or 2, $R^5$ is halo, and $R^2$ is —$NHR^a$, —$NHSO_2R^a$, —$NHC(=O)R^a$, $C_{1-6}$alkenyl, $C_{3-7}$cycloalkyl-$C_{1-4}$alkyl, $C_{3-7}$cycloalkenyl or $C_{3-7}$cycloalkenyl-$C_{1-4}$alkyl.

In certain embodiments of formula II, W is a bond, $R^4$ is hydrogen, p is 1 or 2, $R^5$ is halo, $R^2$ is —$NHR^a$, —$NHSO_2R^a$, —$NHC(=O)R^a$, $C_{1-6}$alkenyl, $C_{3-7}$cycloalkyl-$C_{1-4}$alkyl, $C_{3-7}$cycloalkenyl or $C_{3-7}$cycloalkenyl-$C_{1-4}$alkyl, and $R^a$ is $C_{1-6}$alkyl, $C_{3-7}$cycloalkyl, $C_{3-7}$cycloalkyl-$C_{1-4}$alkyl, $C_{3-7}$cycloalkenyl, $C_{3-7}$cycloalkenyl-$C_{1-4}$alkyl, $C_{1-6}$-alkylsulfonyl$C_{1-6}$alkyl, aryl or heteroaryl.

In certain embodiments of formula II, W is a bond, $R^4$ is hydrogen, p is 1 or 2, $R^5$ is halo, $R^2$ is —$NHR^a$, —$NHSO_2R^a$, —$NHC(=O)R^a$, $C_{1-6}$alkenyl, $C_{3-7}$cycloalkyl-$C_{1-4}$alkyl, $C_{3-7}$cycloalkenyl or $C_{3-7}$cycloalkenyl-$C_{1-4}$alkyl, and $R^a$ is $R^a$ is isopropyl, tert-butyl, thienyl, furanyl, pyridinyl, thienylmethyl, furanylmethyl, pyridinylmethyl, cyclopropyl, cyclobutyl, cyclopentyl, cyclohexyl, cyclopropylmethyl, cyclobutylmethyl, cyclopentylmethyl, cyclohexylnethyl, optionally substituted phenyl, cyclopentenyl optionally substituted with hydroxy, cyclohexenyl optionally substituted with hydroxy, cyclopentenylmethyl optionally substituted with hydroxy, cyclohexenylmethyl optionally substituted with hydroxy, piperidinyl optionally substituted at the 1-position, tetrahydropyranyl, tetrahydrofuranyl, tetrahydropyranylmethyl, tetrahydrofuranylmethyl, 1-butene-4-yl optionally substituted once or twice with methyl, methanesulfonylethyl, or methanesulfonylpropyl.

In certain embodiments of formula II, p is 1 or 2, $R^5$ is halo, W is a bond, $R^4$ is hydrogen, and $R^2$ is —$NHR^a$.

In certain embodiments of formula II, p is 1 or 2, $R^5$ is halo, W is a bond, $R^4$ is hydrogen, $R^2$ is $NHR^a$, and $R^a$ is $C_{1-6}$alkyl, $C_{3-7}$cycloalkyl, $C_{3-7}$cycloalkyl-$C_{1-4}$alkyl, $C_{3-7}$cycloalkenyl, $C_{3-7}$cycloalkenyl-$C_{1-4}$alkyl, halo-$C_{1-6}$alkyl, halo-$C_{3-7}$cycloalkyl, hydroxy-$C_{1-6}$alkyl, $C_{1-6}$alkylsulfonyl$C_{1-6}$alkyl, $C_{1-6}$-alkylsulfanyl-$C_{1-6}$alkyl, arylsulfonyl-$C_{1-6}$alkyl, aryl, aralkyl, heteroaryl, heteroaralkyl, $C_{1-6}$alkylsulfonamidyl$C_{1-6}$alkyl, $C_{1-6}$alkoxycarbonylamino-$C_{1-6}$alkyl, $C_{1-6}$-alkoxycarbonyl-$C_{1-6}$alkyl, $C_{1-6}$alkoxyaminocarbonyl-$C_{1-6}$alkyl, aminocarbonyl-$C_{1-6}$alkyl, $C_{1-6}$alkylaminocarbonyl-$C_{1-6}$alkyl, carboxy-$C_{1-4}$alkyl, heterocyclyl, heterocyclylalkyl, $C_{1-6}$alkylcarbonyl-$C_{1-6}$alkyl, heterocyclyl-$C_{1-6}$alkyl, aryl-$C_{1-6}$alkyl, amino-$C_{1-6}$alkyl, N—$C_{1-6}$alkylamino-$C_{1-6}$alkyl, N,N-di-$C_{1-6}$alkylamino-$C_{1-6}$alkyl, or heteroaryl-$C_{1-6}$alkyl.

In certain embodiments of formula II, p is 1 or 2, $R^5$ is halo, W is a bond, $R^4$ is hydrogen, $R^2$ is NHR$^a$, and R$^a$ is $C_{1-6}$alkyl, $C_{3-7}$cycloalkyl-$C_{1-4}$alkyl, hydroxy-$C_{1-6}$alkyl, $C_{1-6}$alkylsulfonyl$C_{1-6}$alkyl, $C_{1-6}$-alkylsulfanyl-$C_{1-6}$alkyl, arylsulfonyl-$C_{1-6}$alkyl, heterocyclyl, heteroaryl-$C_{1-6}$alkyl or heterocyclyl-$C_{1-6}$alkyl.

In certain embodiments of formula II, p is 1 or 2, $R^5$ is halo, W is a bond, $R^4$ is hydrogen, $R^2$ is NHR$^a$, and R$^a$ is $C_{1-6}$alkyl, $C_{3-7}$cycloalkyl, or $C_{1-6}$alkylsulfonyl-$C_{1-6}$alkyl.

In certain embodiments of formula II, p is 1 or 2, $R^5$ is halo, W is a bond, $R^4$ is hydrogen, $R^2$ is NHR$^a$, and R$^a$ is heterocyclyl selected from tetrahydropyranyl, tetrahydrothiopyranyl, tetrahydrothiophenyl and piperidinyl.

In certain embodiments of formula II, p is 1 or 2, $R^5$ is halo, W is a bond, $R^4$ is hydrogen, $R^2$ is NHR$^a$, and R$^a$ is heterocyclyl selected from tetrahydropyran-4-yl, tetrahydro-thiopyran-3-yl, 1,1-dioxo-hexahydro-1lambda*6*-thiopyran-3-yl, 1,1-dioxo-hexahydro-1lambda*6*-thiopyran-4-yl, 1,1-dioxo-tetrahydro-1lambda*6*-thiophen-3-yl piperidin-4-yl and 1-acetyl-piperidin-4-yl.

In certain embodiments of formula II, p is 1 or 2, $R^5$ is halo, W is a bond, $R^4$ is hydrogen, $R^2$ is NHR$^a$, and R$^a$ is heteroaryl-$C_{1-6}$alky selected from tetrazolyl-$C_{1-6}$alkyl and trIIzolyl-$C_{1-6}$alkyl In certain embodiments of formula II, p is 1 or 2, $R^5$ is halo, W is a bond, $R^4$ is hydrogen, $R^2$ is NHR$^a$, and R$^a$ is heteroarylC$_{1-6}$alky selected from 1-methyl-2-tetrazol-2-yl-ethyl and 1-methyl-2-[1,2,3]trIIzol-2-yl-ethyl.

In certain embodiments of formula II, p is 1 or 2, $R^5$ is halo, W is a bond, $R^4$ is hydrogen, $R^2$ is NHR$^a$, and R$^a$ is heterocyclyl-$C_{1-6}$-alkyl selected from pyrrolidin-$C_{1-6}$alkyl and tetrahydrothiophen-$C_{1-6}$alkyl.

In certain embodiments of formula II, p is 1 or 2, $R^5$ is halo, W is a bond, $R^4$ is hydrogen, $R^2$ is NHR$^a$, and R$^a$ is heterocyclyl-$C_{1-6}$-alkyl selected from pyrrolidin-2-ylmethyl, tetrahydro-thiophen-2-ylmethyl, 1,1-dioxo-tetrahydro-1lambda*6*-thiophen-2-ylmethyl, 1-methanesulfonyl-pyrrolidin-2-ylmethyl, 1-methoxycarbonyl-pyrrolidin-2-ylmethyl and (1,1-dioxo-tetrahydro-1lambda*6*-thiophen-3-ylmethyl.

In certain embodiments of formula II, p is 1 or 2, $R^5$ is halo, W is a bond, $R^4$ is hydrogen, $R^2$ is NHR$^a$, and R$^a$ is cyclohexyl or cyclopentyl substituted with $C_{1-6}$alkylsulfonyl.

In certain embodiments of formula II, p is 1 or 2, $R^5$ is halo, W is a bond, $R^4$ is hydrogen, $R^2$ is NHR$^a$, and R$^a$ is 2-methanesulfonyl-cyclopentyl.

In certain embodiments of formula II, p is 1 or 2, $R^5$ is halo, W is a bond, $R^4$ is hydrogen, $R^2$ is NHR$^a$, and R$^a$ is isopropyl or isobutyl.

In certain embodiments of formula II, p is 1 or 2, $R^5$ is halo, W is a bond, $R^4$ is hydrogen, $R^2$ is NHR$^a$, and R$^a$ is $C_{1-6}$-alkylsulfonyl$C_{1-6}$-alkyl.

In certain embodiments of formula II, p is 1 or 2, $R^5$ is halo, W is a bond, $R^4$ is hydrogen, $R^2$ is NHR$^a$, and R$^a$ is 2-methanesulfonyl-1-methyl-ethyl, 2-methanesulfonyl-ethyl, 3-methanesulfonyl-propyl, 3-methanesulfonyl-1-methyl-propyl, 3-methanesulfonyl-2-methyl-propyl, 2-ethanesulfonyl-1-methyl-ethyl or 1-methanesulfonylmethyl-propyl.

In certain embodiments of formula II, p is 1 or 2, $R^5$ is halo, W is a bond, $R^4$ is hydrogen, $R^2$ is NHR$^a$, and R$^a$ is 2-methanesulfonyl-1-methyl-ethyl.

In certain embodiments of formula II, p is 1 or 2, $R^5$ is halo, W is a bond, $R^4$ is hydrogen, R is NHR$^a$, and R$^a$ is (R)-2-methanesulfonyl-1-methyl-ethyl.

In certain embodiments of formula II, p is 1 or 2, $R^5$ is halo, W is a bond, $R^4$ is hydrogen, $R^2$ is NHR$^a$, and R$^a$ is (S)-2-methanesulfonyl-1-methyl-ethyl.

In certain embodiments of formula II, p is 1 or 2, $R^5$ is halo, W is a bond, $R^4$ is hydrogen, $R^2$ is NHR$^a$, and R$^a$ is isopropyl.

In certain embodiments of formula Ia, the subject compounds may be of formula III:

wherein W, $R^2$, $R^4$ and R$^a$ are as defined herein.

In certain embodiments of formula III, W is NR$^f$ or O and $R^4$ is heteroalkyl.

In certain embodiments of formula III, W is a bond and $R^4$ is hydrogen.

In certain embodiments of formula III, $R^2$ is —NHR$^a$, —NHSO$_2$R$^a$, —NHC(=O)R$^a$, $C_{1-6}$alkenyl, $C_{3-7}$cycloalkyl-$C_{1-4}$alkyl, $C_{3-7}$cycloalkenyl, $C_{3-7}$cycloalkenyl-$C_{1-4}$alkyl, halo-$C_{3-7}$cycloalkyl, $C_{1-6}$alkylsulfonyl$C_{1-6}$alkyl, $C_{1-6}$alkylsulfanyl-$C_{1-6}$alkyl, aryl-$C_{1-6}$alkyl or heteroaryl-$C_{1-6}$alkyl.

In certain embodiments of formula III, $R^2$ is —NHR$^a$, —NHSO$_2$R$^a$, —NHC(=O)R$^a$, $C_{1-6}$alkenyl, $C_{3-7}$cycloalkyl-$C_{1-4}$alkyl, $C_{3-7}$cycloalkenyl or $C_{3-7}$cycloalkenyl-$C_{1-4}$alkyl.

In certain embodiments of formula III, $R^2$ is —NHR$^a$, —NHSO$_2$R$^a$, or —NHC(=O)R$^a$.

In certain embodiments of formula III, $R^2$ is —NHR$^a$.

In certain embodiments of formula III, $R^2$ is —NHSO$_2$R$^a$.

In certain embodiments of formula III, $R^2$ is —NHC(=O)R$^a$.

In certain embodiments of formula III, R$^a$ is $C_{1-6}$alkyl, $C_{3-7}$cycloalkyl, $C_{3-7}$cycloalkyl-$C_{1-4}$alkyl, $C_{3-7}$cycloalkenyl, $C_{3-7}$cycloalkenyl-$C_{1-4}$alkyl, $C_{1-6}$alkylsulfonyl$C_{1-6}$alkyl, aryl or heteroaryl.

In certain embodiments of formula III, R$^a$ is $C_{1-6}$alkyl, $C_{3-7}$cycloalkyl, $C_{3-7}$cycloalkyl-$C_{1-4}$alkyl, or $C_{1-6}$-alkylsulfonyl$C_{1-6}$alkyl.

In certain embodiments of formula III, R$^a$ is isopropyl, tert-butyl, thienyl, furanyl, pyridinyl, thienylmethyl, furanylmethyl, pyridinylmethyl, cyclopropyl, cyclobutyl, cyclopentyl, cyclohexyl, cyclopropylmethyl, cyclobutylmethyl, cyclopentylmethyl, cyclohexylnethyl, optionally substituted phenyl, cyclopentenyl optionally substituted with hydroxy, cyclohexenyl optionally substituted with hydroxy, cyclopentenylmethyl optionally substituted with hydroxy, cyclohexenylmethyl optionally substituted with hydroxy, piperidinyl optionally substituted at the 1-position, tetrahydropyranyl, tetrahydrofuranyl, tetrahydropyranylmethyl, tetrahydrofuranylmethyl, 1-butene-4-yl optionally substituted once or twice with methyl, 2-methanesulfonyl-1-methyl-ethyl, 2-methanesulfonyl-ethyl, 3-methanesulfonyl-propyl, 3-methanesulfonyl-1-methyl-propyl, 3-methanesulfonyl-2-methyl-propyl, 2-ethanesulfonyl-1-methyl-ethyl and 1-methanesulfonylmethyl-propyl.

In certain embodiments of formula II, $R^a$ is $C_{1-6}$alkylsulfonyl$C_{1-6}$alkyl selected from 2-methanesulfonyl-1-methyl-ethyl, 2-methanesulfonyl-ethyl, 3-methanesulfonyl-propyl, 3-methanesulfonyl-1-methyl-propyl, 3-methanesulfonyl-2-methyl-propyl, 2-ethanesulfonyl-1-methyl-ethyl and 1-methanesulfonylmethyl-propyl.

In certain embodiments of formula II, $R^a$ is (R)-2-methanesulfonyl-1-methyl-ethyl or (S)-2-methanesulfonyl-1-methyl-ethyl.

In certain embodiments of formula III, W is a bond, $R^4$ is hydrogen, $R^2$ is —$NHR^a$, —$NHSO_{2R}{}^a$, —NHC(=O)$R^a$, $C_{1-6}$alkenyl, $C_{3-7}$cycloalkyl-$C_{1-4}$alkyl, $C_{3-7}$cycloalkenyl or $C_{3-7}$cycloalkenyl-$C_{1-4}$alkyl, and $R^a$ is $C_{1-6}$alkyl, $C_{3-7}$cycloalkyl, $C_{3-7}$cycloalkyl-$C_{1-4}$alkyl, $C_{3-7}$cycloalkenyl, $C_{3-7}$cycloalkenyl-$C_{1-4}$alkyl, $C_{1-6}$alkylsulfonyl$C_{1-6}$alkyl, aryl or heteroaryl.

In certain embodiments of formula III, W is a bond, $R^4$ is hydrogen, $R^2$ is —$NHR^a$, —$NHSO_2R^a$, —NHC(=O)$R^a$, $C_{1-6}$alkenyl, $C_{3-7}$cycloalkyl-$C_{1-4}$alkyl, $C_{3-7}$cycloalkenyl or $C_{3-7}$cycloalkenyl-$C_{1-4}$alkyl, and $R^a$ is $R^a$ is isopropyl, tert-butyl, thienyl, furanyl, pyridinyl, thienylmethyl, furanylmethyl, pyridinymethyl, cyclopropyl, cyclobutyl, cyclopentyl, cyclohexyl, cyclopropylmethyl, cyclobutylmethyl, cyclopentylmethyl, cyclohexylnethyl, optionally substituted phenyl, cyclopentenyl optionally substituted with hydroxy, cyclohexenyl optionally substituted with hydroxy, cyclopentenylmethyl optionally substituted with hydroxy, cyclohexenylmethyl optionally substituted with hydroxy, piperidinyl optionally substituted at the 1-position, tetrahydropyranyl, tetrahydrofuranyl, tetrahydropyranylmethyl, tetrahydrofuranylmethyl, 1-butene-4-yl optionally substituted once or twice with methyl, 2-methanesulfonyl-1-methyl-ethyl, 2-methanesulfonyl-ethyl, 3-methanesulfonyl-propyl, 3-methanesulfonyl-1-methyl-propyl, 3-methanesulfonyl-2-methyl-propyl, 2-ethanesulfonyl-1-methyl-ethyl and 1-methanesulfonylmethyl-propyl.

In certain embodiments of formula III, W is a bond, $R^4$ is hydrogen, and $R^2$ is —$NHR^a$.

In certain embodiments of formula III, W is a bond, $R^4$ is hydrogen, $R^2$ is $NHR^a$, and $R^a$ is $C_{1-6}$alkyl, $C_{3-7}$cycloalkyl, $C_{3-7}$cycloalkyl-$C_{1-4}$alkyl, $C_{3-7}$cycloalkenyl, $C_{3-7}$cycloalkenyl-$C_{1-4}$alkyl, halo-$C_{1-6}$alkyl, halo-$C_{3-7}$cycloalkyl, hydroxy-$C_{1-6}$alkyl, $C_{1-6}$-alkylsulfonyl$C_{1-6}$alkyl, $C_{1-6}$alkylsulfanyl-$C_{1-6}$alkyl, arylsulfonyl-$C_{1-6}$alkyl, aryl, aralkyl, heteroaryl, heteroaralkyl, $C_{1-6}$-alkylsulfonamidyl$C_{1-6}$alkyl, $C_{1-6}$alkoxycarbonylamino-$C_{1-6}$alkyl, $C_{1-6}$alkoxycarbonyl-$C_{1-6}$alkyl, $C_{1-6}$alkoxyaminocarbonyl-$C_{1-6}$alkyl, aminocarbonyl-$C_{1-6}$alkyl, $C_{1-6}$alkylaminocarbonyl-$C_{1-6}$alkyl, carboxy-$C_{1-6}$alkyl, heterocyclyl, heterocyclylalkyl, $C_{1-6}$alkylcarbonyl-$C_{1-6}$alkyl, heterocyclyl-$C_{1-6}$alkyl, aryl-$C_{1-6}$alkyl, amino-$C_{1-6}$alkyl, N—$C_{1-6}$alkylamino-$C_{1-6}$alkyl, N,N-di-$C_{1-6}$alkylamino-$C_{1-6}$alkyl, or heteroaryl-$C_{1-6}$alkyl.

In certain embodiments of formula III, W is a bond, $R^4$ is hydrogen, $R^2$ is $NHR^a$, and $R^a$ is $C_{1-6}$alkyl, $C_{3-7}$cycloalkyl-$C_{1-4}$alkyl, hydroxy-$C_{1-6}$alkyl, $C_{1-6}$alkylsulfonyl$C_{1-6}$alkyl, $C_{1-6}$alkylsulfanyl-$C_{1-6}$alkyl, arylsulfonyl-$C_{1-6}$alkyl, heterocyclyl, heteroaryl-$C_{1-6}$alkyl or heterocyclyl-$C_{1-6}$alkyl.

In certain embodiments of formula III, W is a bond, $R^4$ is hydrogen, $R^2$ is $NHR^a$, and $R^a$ is $C_{1-6}$alkyl, $C_{3-7}$cycloalkyl, or $C_{1-6}$alkylsulfonyl-$C_{1-6}$alkyl.

In certain embodiments of formula III, W is a bond, $R^4$ is hydrogen, $R^2$ is $NHR^a$, and $R^a$ is $C_{1-6}$alkylsulfonyl$C_{1-6}$alkyl.

In certain embodiments of formula III, W is a bond, $R^4$ is hydrogen, $R^2$ is $NHR^a$, and $R^a$ is heterocyclyl selected from tetrahydropyranyl, tetrahydrothiopyranyl, tetrahydrothiophenyl and piperidinyl.

In certain embodiments of formula III, W is a bond, $R^4$ is hydrogen, $R^2$ is $NHR^a$, and $R^a$ is heterocyclyl selected from tetrahydropyran-4-yl, tetrahydro-thiopyran-3-yl, 1,1-dioxo-hexahydro-1lambda*6*-thiopyran-3-yl, 1,1-dioxo-hexahydro-1lambda*6*-thiopyran-4-yl, 1,1-dioxo-tetrahydro-1lambda*6*-thiophen-3-yl, piperidin-4-yl and 1-acetyl-piperidin-4-yl.

In certain embodiments of formula III, W is a bond, $R^4$ is hydrogen, $R^2$ is $NHR^a$, and $R^a$ is heteroaryl-$C_{1-6}$alky selected from tetrazolyl-$C_{1-6}$alkyl and trIlzolyl-$C_{1-6}$alkyl.

In certain embodiments of formula III, W is a bond, $R^4$ is hydrogen, $R^2$ is $NHR^a$, and $R^a$ is heteroaryl$C_{1-6}$alky selected from 1-methyl-2-tetrazol-2-yl-ethyl and 1-methyl-2-[1,2,3]trIlzol-2-yl-ethyl.

In certain embodiments of formula III, W is a bond, $R^4$ is hydrogen, $R^2$ is $NHR^a$, and $R^a$ is heterocyclyl-$C_{1-6}$alkyl selected from pyrrolidin-$C_{1-6}$alkyl and tetrahydrothiophen-$C_{1-6}$alkyl.

In certain embodiments of formula III, W is a bond, $R^4$ is hydrogen, $R^2$ is $NHR^a$, and $R^a$ is heterocyclyl-$C_{1-6}$alkyl selected from pyrrolidin-2-ylmethyl, tetrahydro-thiophen-2-ylmethyl, 1,1-dioxo-tetrahydro-1lambda*6*-thiophen-2-ylmethyl, 1-methanesulfonyl-pyrrolidin-2-ylmethyl, 1-methoxycarbonyl-pyrrolidin-2-ylmethyl and (1,1-dioxo-tetrahydro-1lambda*6*-thiophen-3-ylmethyl.

In certain embodiments of formula III, W is a bond, $R^4$ is hydrogen, $R^2$ is $NHR^a$, and $R^a$ is cyclohexyl or cyclopentyl substituted with $C_{1-6}$-alkylsulfonyl.

In certain embodiments of formula III, W is a bond, $R^4$ is hydrogen, $R^2$ is $NHR^a$, and $R^a$ is 2-methanesulfonyl-cyclopentyl.

In certain embodiments of formula III, W is a bond, $R^4$ is hydrogen, $R^2$ is $NHR^a$, and $R^a$ is isopropyl or isobutyl.

In certain embodiments of formula III, W is a bond, $R^4$ is hydrogen, $R^2$ is $NHR^a$, and $R^a$ is 2-methanesulfonyl-1-methyl-ethyl, 2-methanesulfonyl-ethyl, 3-methanesulfonyl-propyl, 3-methanesulfonyl-1-methyl-propyl, 3-methanesulfonyl-2-methyl-propyl, 2-ethanesulfonyl-1-methyl-ethyl or 1-methanesulfonylmethyl-propyl.

In certain embodiments of formula III, W is a bond, $R^4$ is hydrogen, $R^2$ is $NHR^a$, and $R^a$ is 2-methanesulfonyl-1-methyl-ethyl.

In certain embodiments of formula III, W is a bond, $R^4$ is hydrogen, $R^2$ is $NHR^a$, and $R^a$ is (R)-2-methanesulfonyl-1-methyl-ethyl.

In certain embodiments of formula III, W is a bond, $R^4$ is hydrogen, $R^2$ is $NHR^a$, and $R^a$ is (S)-2-methanesulfonyl-1-methyl-ethyl.

In certain embodiments of formula III, W is a bond, $R^4$ is hydrogen, $R^2$ is $NHR^a$, and $R^a$ is isopropyl.

In certain embodiments of formula III, the subject compounds may be of formula IIIa, IIIb or IIIc:

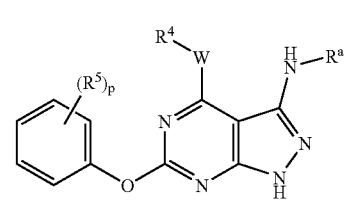

IIIa

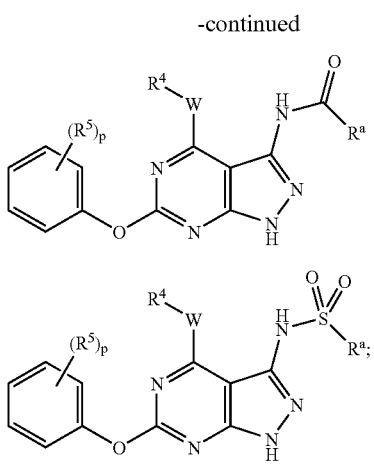

wherein p, W, $R^4$, $R^5$ and $R^a$ are as defined herein.

In certain embodiments of any of formulas IIIa, IIIb and IIIc, $R^a$ is $C_{1-6}$alkyl, $C_{3-7}$cycloalkyl, $C_{3-7}$cycloalkyl-$C_{1-4}$ alkyl, $C_{3-7}$cycloalkenyl, $C_{3-7}$cycloalkenyl-$C_{1-4}$alkyl, $C_{1-6}$alkylsulfonyl$C_{1-6}$alkyl, aryl or heteroaryl.

In certain embodiments of any of formulas IIIa, IIIb and IIIc, $R^a$ is $C_{1-6}$alkyl, $C_{3-7}$cycloalkyl, $C_{3-7}$cycloalkyl-$C_{1-4}$ alkyl, or $C_{1-6}$alkylsulfonyl$C_{1-6}$alkyl.

In certain embodiments of any of formulas IIIa, IIIb and IIIc, $R^a$ is isopropyl, tert-butyl, thienyl, furanyl, pyridinyl, thienylmethyl, furanylmethyl, pyridinylmethyl, cyclopropyl, cyclobutyl, cyclopentyl, cyclohexyl, cyclopropylmethyl, cyclobutylmethyl, cyclopentylmethyl, cyclohexylnethyl, ,optionally substituted phenyl, cyclopentenyl optionally substituted with hydroxy, cyclohexenyl optionally substituted with hydroxy, cyclopentenylmethyl optionally substituted with hydroxy, cyclohexenylmethyl optionally substituted with hydroxy, piperidinyl optionally substituted at the 1-position, tetrahydropyranyl, tetrahydrofuranyl, tetrahydropyranylmethyl, tetrahydrofuranylmethyl, 1-butene-4-yl optionally substituted once or twice with methyl, methanesulfonylethyl, or methanesulfonylpropyl.

In certain embodiments of any of formulas IIIa, IIIb and IIIc, W is a bond and $R^4$ is hydrogen.

In certain embodiments of any of formulas IIIa, IIIb and IIIc, p is 1 or 2 and $R^5$ is halo.

In certain embodiments of formula IIIa, p is 1 or 2, $R^5$ is halo, W is a bond, $R^4$ is hydrogen, and $R^a$ is $C_{1-6}$alkyl, $C_{3-7}$cycloalkyl, $C_{3-7}$cycloalkyl-$C_{1-4}$alkyl, $C_{3-7}$cycloalkenyl, $C_{3-7}$cycloalkenyl-$C_{1-4}$alkyl, halo-$C_{1-6}$alkyl, halo-$C_{3-7}$cycloalkyl, hydroxy-$C_{1-6}$alkyl, $C_{1-6}$-alkylsulfonyl$C_{1-6}$alkyl, $C_{1-6}$alkylsulfanyl-$C_{1-6}$alkyl, arylsulfonyl-$C_{1-6}$alkyl, aryl, aralkyl, heteroaryl, heteroaralkyl, $C_{1-6}$alkylsulfonamidyl$C_{1-6}$ alkyl, $C_{1-6}$alkoxycarbonylamino-$C_{1-6}$alkyl, $C_{1-6}$alkoxycarbonyl-$C_{1-6}$alkyl, $C_{1-6}$alkoxyaminocarbonyl-$C_{1-6}$alkyl, aminocarbonyl-$C_{1-6}$alkyl, $C_{1-6}$alkylaminocarbonyl-$C_{1-6}$alkyl, carboxy-$C_{1-6}$alkyl, heterocyclyl, heterocyclylalkyl, $C_{1-6}$alkylcarbonyl-$C_{1-6}$alkyl, heterocyclyl-$C_{1-6}$alkyl, aryl-$C_{1-6}$alkyl, amino-$C_{1-6}$alkyl, N—$C_{1-6}$alkylamino-$C_{1-6}$alkyl, N,N-di-$C_{1-6}$alkylamino-$C_{1-6}$alkyl, or heteroaryl-$C_{1-6}$alkyl.

In certain embodiments of formula IIIa, p is 1 or 2, $R^5$ is halo, W is a bond, $R^4$ is hydrogen, and $R^a$ is $C_{1-6}$alkyl, $C_{3-7}$cycloalkyl-$C_{1-4}$alkyl, hydroxy-$C_{1-6}$alkyl, $C_{1-6}$alkylsulfonyl$C_{1-6}$ alkyl, $C_{1-6}$alkylsulfanyl-$C_{1-6}$alkyl, arylsulfonyl-$C_{1-6}$ alkyl, heterocyclyl, heteroaryl-$C_{1-6}$alkyl or heterocyclyl-$C_{1-6}$ alkyl.

In certain embodiments of formula IIIa, p is 1 or 2, $R^5$ is halo, W is a bond, $R^4$ is hydrogen, and $R^a$ is $C_{1-6}$alkyl, $C_{3-7}$cycloalkyl, or $C_{1-6}$alkylsulfonyl-$C_{1-6}$alkyl.

In certain embodiments of formula IIIa, p is 1 or 2, $R^5$ is halo, W is a bond, $R^4$ is hydrogen, and $R^a$ is heterocyclyl selected from tetrahydropyranyl, tetrahydrothiopyranyl, tetrahydrothiophenyl and piperidinyl.

In certain embodiments of formula IIIa, p is 1 or 2, $R^5$ is halo, W is a bond, $R^4$ is hydrogen, and $R^a$ is heterocyclyl selected from tetrahydropyran-4-yl, tetrahydro-thiopyran-3-yl, 1,1-dioxo-hexahydro-1lambda*6*-thiopyran-3-yl, 1,1-dioxo-hexahydro-1lambda*6*-thiopyran-4-yl, 1,1-dioxo-tetrahydro-1lambda*6*-thiophen-3-yl, piperidin-4-yl and 1-acetyl-piperidin-4-yl.

In certain embodiments of formula IIIa, p is 1 or 2, $R^5$ is halo, W is a bond, $R^4$ is hydrogen, and $R^a$ is heteroaryl-$C_{1-6}$ alky selected from tetrazolyl-$C_{1-6}$alkyl and trllzolyl-$C_{1-6}$ alkyl.

In certain embodiments of formula IIIa, p is 1 or 2, $R^5$ is halo, W is a bond, $R^4$ is hydrogen, and $R^a$ is heteroaryl$C_{1-6}$ alky selected from 1-methyl-2-tetrazol-2-yl-ethyl and 1-methyl-2-[1,2,3]trIIzol-2-yl-ethyl.

In certain embodiments of formula IIIa, p is 1 or 2, $R^5$ is halo, W is a bond, $R^4$ is hydrogen, and $R^a$ is heterocyclyl-$C_{1-6}$ alkyl selected from pyrrolidin-$C_{1-6}$alkyl and tetrahydrothiophen-$C_{1-6}$alkyl.

In certain embodiments of formula IIIa, p is 1 or 2, $R^5$ is halo, W is a bond, $R^4$ is hydrogen, and $R^a$ is heterocyclyl-$C_{1-6}$ alkyl selected from pyrrolidin-2-ylmethyl, tetrahydro-thiophen-2-ylmethyl, 1,1-dioxo-tetrahydro-1lambda*6*-thiophen-2-ylmethyl, 1-methanesulfonyl-pyrrolidin-2-ylmethyl, 1-methoxycarbonyl-pyrrolidin-2-ylmethyl and (1,1-dioxo-tetrahydro-1lambda*6*-thiophen-3-ylmethyl.

In certain embodiments of formula IIIa, p is 1 or 2, $R^5$ is halo, W is a bond, $R^4$ is hydrogen, and $R^a$ is $C_{1-6}$alkylsulfonyl$C_{1-6}$alkyl.

In certain embodiments of formula IIIa, p is 1 or 2, $R^5$ is halo, W is a bond, $R^4$ is hydrogen, and $R^a$ is cyclohexyl or cyclopentyl substituted with $C_{1-6}$alkylsulfonyl.

In certain embodiments of formula IIIa, p is 1 or 2, $R^5$ is halo, W is a bond, $R^4$ is hydrogen, and $R^a$ is 2-methanesulfonyl-cyclopentyl.

In certain embodiments of formula IIIa, p is 1 or 2, $R^5$ is halo, W is a bond, $R^4$ is hydrogen, and $R^a$ is isopropyl or isobutyl.

In certain embodiments of formula IIIa, p is 1 or 2, $R^5$ is halo, W is a bond, $R^4$ is hydrogen, and $R^a$ is 2-methanesulfonyl-1-methyl-ethyl, 2-methanesulfonyl-ethyl, 3-methanesulfonyl-propyl, 3-methanesulfonyl-1-methyl-propyl, 3-methanesulfonyl-2-methyl-propyl, 2-ethanesulfonyl-1-methyl-ethyl or 1-methanesulfonylmethyl-propyl.

In certain embodiments of formula IIIa, p is 1 or 2, $R^5$ is halo, W is a bond, $R^4$ is hydrogen, and $R^a$ is 2-methanesulfonyl-1-methyl-ethyl.

In certain embodiments of formula IIIa, p is 1 or 2, $R^5$ is halo, W is a bond, $R^4$ is hydrogen, and $R^a$ is (R)-2-methanesulfonyl-1-methyl-ethyl.

In certain embodiments of formula IIIa, p is 1 or 2, $R^5$ is halo, W is a bond, $R^4$ is hydrogen, and $R^a$ is (S)-2-methanesulfonyl-1-methyl-ethyl.

In certain embodiments of formula IIIa, p is 1 or 2, $R^5$ is halo, W is a bond, $R^4$ is hydrogen, and $R^a$ is isopropyl.

In another aspect of the invention, there are provided compounds of the formula IVa or IVb:

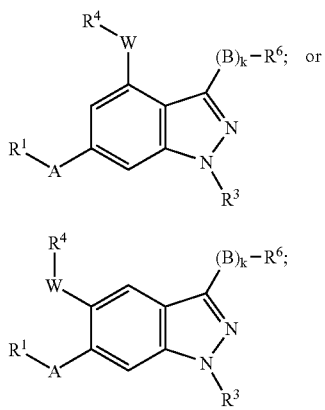

or a pharmaceutically acceptable salt thereof,
wherein:
$R^1$ is aryl, heteroaryl, aryl-$C_{1-6}$alkyl or $C_{3-7}$cycloalkyl;
$R^3$ is hydrogen or $C_{1-6}$alkyl;
$R^4$ is hydrogen, $C_{1-6}$alkyl, hydroxy, amino, hetero-$C_{1-6}$alkyl, heterocyclyl, heterocyclyl-$C_{1-6}$alkyl, hydroxy-$C_{3-7}$cycloalkyl, $C_{3-7}$cycloalkyl-$C_{1-6}$alkyl, $C_{1-6}$alkylsulfonyl, $C_{1-6}$alkylsulfonamido, aryl, heteroaryl, aryl-$C_{1-6}$alkyl, heteroaryl-$C_{1-6}$alkyl, —(CHR$^b$)$_r$—C(=O)—R$^c$, —(CHR$^b$)$_r$—O—C(=O)—R$^c$, —(CHR$^b$)$_r$—NH—C(=O)—R$^c$ or —SO$_2$—R$^c$,
wherein
$R^b$ is hydrogen, $C_{1-6}$alkyl or hetero-$C_{1-6}$alkyl;
$R^c$ is $C_{1-6}$alkyl, hydroxy, amino, hetero-$C_{1-6}$alkyl, aryl, aryl-$C_{1-6}$alkyl, heteroaryl, or heterocyclyl;
r is from 0 to 4;
W is O, S(O)$_m$, CH$_2$ or NR$^f$,
wherein
m is from 0 to 2, and
$R^f$ is hydrogen, $C_{1-6}$alkyl, hetero-$C_{1-6}$alkyl, heterocyclyl, hydroxyC$_{3-7}$cycloalkyl, —C(=O)R$^g$ or —SO$_2$—R$^g$,
wherein
$R^g$ is $C_{1-6}$alkyl, aryl, aryl-$C_{1-6}$alkyl, heteroaryl, hetero-$C_{1-6}$alkyl or heterocyclyl;
or $R^4$ and $R^f$ together with the atoms to which they are attached may form a heterocyclic ring;
A is O, CH$_2$, S(O)$_n$, C(=O), NR$^h$, or CH(OR$^h$),
wherein
n is from 0 to 2, and
$R^h$ is hydrogen or $C_{1-6}$alkyl,
or $R^1$ and $R^h$ may form a heterocyclyl;
k is 0 or 1;
$R^6$ is aryl, heteroaryl, $C_{3-7}$cycloalkyl, branched $C_{1-6}$alkyl or heterocyclyl;
B is O, S(O)$_j$, CH(OR$^{i1}$), NH, C(=O), NHC(=O) or NHSO$_2$,
wherein
j is 0, 1 or 2; and
$R^i$ is hydrogen or $C_{1-6}$alkyl,
In certain embodiments of of formula IVa or IVb, k is 0.
In certain embodiments of of formula IVa or IVb, A is O, S(O)$_n$, or NR$^h$,
In certain embodiments of of formula IVa or IVb, $R^1$ is aryl.
In certain embodiments of of formula IVa or IVb, $R^6$ is aryl.
In certain embodiments of of formula IVa or IVb, $R^3$ is hydrogen.

In certain embodiments of of formula IVa or IVb, W is O or NR$^c$.
In certain embodiments of of formula IVa or IVb, $R^1$ and $R^6$ are optionally substituted phenyl.
In certain embodiments of of formula IVa or IVb, $R^4$ is hetero-$C_{1-6}$alkyl or heterocyclyl-$C_{1-6}$alkyl.
In certain embodiments of of formula IVa or IVb, A is O.
In certain embodiments of of formula IVa or IVb, A is O, and $R^1$ is 2-halophenyl or 2,4-dihalophenyl.
In certain embodiments of of formula IVa or IVb, A is O, $R^1$ is 2-halophenyl or 2,4-dihalophenyl, and $R^6$ is optionally substituted phenyl.
In certain embodiments of of formula IVa or IVb, A is O, $R^1$ is 2-halophenyl or 2,4-dihalophenyl, $R^6$ is optionally substituted phenyl, and W is O or NR$^c$.
In certain embodiments of of formula IVa or IVb, A is O, $R^1$ is 2-halophenyl or 2,4-dihalophenyl, $R^6$ is optionally substituted phenyl, W is O or NR$^c$, and $R^4$ is hydroxy-$C_{1-6}$alkyl, amino-$C_{1-6}$alkyl, alkyl-$C_{1-6}$sulfonyl-$C_{1-6}$alkyl or heterocyclyl-$C_{1-6}$alkyl.
In certain embodiments of of formula IVa or IVb, A is O, $R^1$ is 2-halophenyl or 2,4-dihalophenyl, $R^6$ is optionally substituted phenyl, W is O or NR$^c$, and $R^4$ is hydroxy-$C_{1-6}$alkyl or morpholinyl-$C_{1-6}$alkyl.
In embodiments of formula IVa, the subject compounds may be more specifically of formula V:

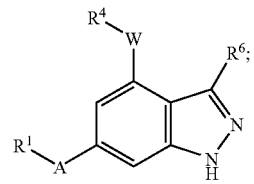

wherein A, W, $R^1$, $R^4$ and $R^6$ are as defined herein.
In certain embodiments of formula V, $R^1$ is 2-halophenyl or 2,4-dihalophenyl.
In certain embodiments of formula V, $R^6$ is optionally substituted phenyl.
In certain embodiments of formula V, W is O or NR$^c$.
In certain embodiments of formula V, $R^4$ is hetero-$C_{1-6}$alkyl or heterocyclyl-$C_{1-6}$alkyl.
In certain embodiments of formula V, A is O.
In certain embodiments of formula V, A is O, and $R^1$ is 2-halophenyl or 2,4-dihalophenyl.
In certain embodiments of formula V, A is O, $R^1$ is 2-halophenyl or 2,4-dihalophenyl, and $R^6$ is optionally substituted phenyl.
In certain embodiments of formula V, A is O, $R^1$ is 2-halophenyl or 2,4-dihalophenyl, $R^6$ is optionally substituted phenyl, and W is O or NR$^c$.
In certain embodiments of formula V, A is O, $R^1$ is 2-halophenyl or 2,4-dihalophenyl, $R^6$ is optionally substituted phenyl, W is O or NR$^c$, and $R^4$ is hydroxy-$C_{1-6}$alkyl, amino-$C_{1-6}$alkyl, alkyl-$C_{1-6}$sulfonyl-$C_{1-6}$alkyl or heterocyclyl-$C_{1-6}$alkyl.
In certain embodiments of formula V, A is O, $R^1$ is 2-halophenyl or 2,4-dihalophenyl, $R^6$ is optionally substituted phenyl, W is O or NR$^c$, and $R^4$ is hydroxy-$C_{1-6}$alkyl or morpholinyl-$C_{1-6}$alkyl.
In embodiments of formula IVa, the subject compounds may be more specifically of formula VI:

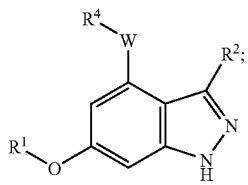

wherein W, $R^1$, $R^4$ and $R^6$ are as defined herein.

In certain embodiments of formula VI, $R^1$ is 2-halophenyl or 2,4-dihalophenyl.

In certain embodiments of formula VI, $R^6$ is optionally substituted phenyl.

In certain embodiments of formula VI, W is O or $NR^c$.

In certain embodiments of formula VI, $R^4$ is hetero-$C_{1-6}$alkyl or heterocyclyl-$C_{1-6}$alkyl.

In certain embodiments of formula VI, $R^1$ is 2-halophenyl or 2,4-dihalophenyl, and $R^6$ is optionally substituted phenyl.

In certain embodiments of formula VI, $R^1$ is 2-halophenyl or 2,4-dihalophenyl, $R^6$ is optionally substituted phenyl, and W is O or $NR^c$.

In certain embodiments of formula VI, $R^1$ is 2-halophenyl or 2,4-dihalophenyl, $R^6$ is optionally substituted phenyl, W is O or $NR^c$, and $R^4$ is hydroxy-$C_{1-6}$alkyl, amino-$C_{1-4}$alkyl, alkyl-$C_{1-6}$alkyl or heterocyclyl-$C_{1-6}$alkyl.

In certain embodiments of formula VI, $R^1$ is 2-halophenyl or 2,4-dihalophenyl, $R^6$ is optionally substituted phenyl, W is O or $NR^c$, and $R^4$ is hydroxy-$C_{1-6}$alkyl or morpholinyl-$C_{1-6}$alkyl.

In embodiments of formula IVa, the subject compounds may be more specifically of formula VII:

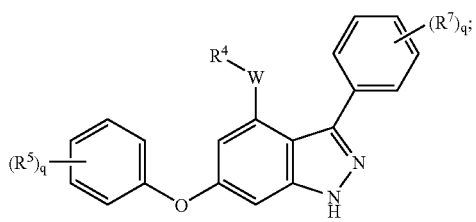

wherein
p and q each independently is independently from 0 to 4;
each $R^5$ is independently halo, $C_{1-6}$alkyl, $C_{1-6}$alkoxy, halo-$C_{1-6}$alkyl, or cyano;
each $R^7$ is independently halo, $C_{1-6}$alkyl, halo-$C_{1-6}$alkyl, cyano, hetero-$C_{1-6}$alkyl, heterocyclyl, $C_{1-6}$alkylsulfonyl, aminosulfonyl, $C_{1-6}$alkylsulfonylamino, hydroxy$C_{3-7}$cycloalkyl or —C(=O) $R^k$;
wherein
$R^k$ is alkyl, heteroalkyl, aryl, aralkyl, heteroaryl or heterocyclyl; and W and $R^4$ are as defined herein.

In certain embodiments of formula VI, p is 1 or 2 and $R^5$ is halo.

In certain embodiments of formula VI, q is 1 or 2 and $R^7$ is halo.

In certain embodiments of formula VI, W is O or $NR^c$.

In certain embodiments of formula VI, $R^4$ is heteroalkyl or heterocyclylalkyl.

In certain embodiments of formula VI, $R^4$ is hydroxyalkyl or morpholinylalkyl.

The invention also provides a method for making a compound of formula ee;

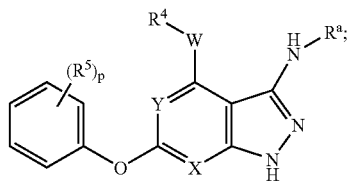

wherein:
p is from 0 to 4;
one of X and Y is N and the other is CH, or X and Y are both N;
W is O, $NR^f$, or a bond wherein $R^f$ is hydrogen, alkyl or a protecting group;
$R^a$ is $C_{1-6}$alkyl, $C_{3-7}$cycloalkyl, $C_{3-7}$cycloalkyl-$C_{1-4}$alkyl, $C_{3-7}$cycloalkenyl, $C_{3-7}$cycloalkenyl-$C_{1-4}$alkyl, halo-$C_{1-6}$ alkyl, halo-$C_{3-7}$cycloalkyl, hydroxy-$C_{1-6}$alkyl, $C_{1-6}$alkylsulfonyl$C_{1-6}$alkyl, $C_{1-6}$alkylsulfanyl-$C_{1-6}$alkyl, arylsulfonyl-$C_{1-6}$alkyl, aryl, aryl-$C_{1-6}$alkyl, heteroaryl, heteroaryl-$C_{1-6}$alkyl, $C_{1-6}$alkylsulfonamidyl$C_{1-6}$ alkyl, $C_{1-6}$alkoxycarbonylamino-$C_{1-6}$alkyl, $C_{1-6}$alkoxycarbonyl-$C_{1-6}$alkyl, $C_{1-6}$alkoxyaminocarbonyl-$C_{1-6}$alkyl, aminocarbonyl-$C_{1-6}$alkyl, $C_{1-6}$alkylaminocarbonyl-$C_{1-6}$alkyl, carboxy-$C_{1-6}$alkyl, heterocyclyl, heterocyclylalkyl, $C_{1-6}$alkylcarbonyl-$C_{1-6}$alkyl, heterocyclyl-$C_{1-6}$alkyl, aryl-$C_{1-6}$alkyl, amino-$C_{1-6}$alkyl, N—$C_{1-6}$alkylamino-$C_{1-6}$alkyl, N,N-di-$C_{1-6}$alkylamino-$C_{1-6}$alkyl, $C_{1-6}$alkoxy-$C_{1-6}$alkyl, or heteroaryl-$C_{1-6}$alkyl,
$R^4$ is hyrdogen, hydroxyalkyl, alkoxyalkyl or alkylsulfonylalkyl; and
$R^5$ is halo, alkyl, alkoxy, haloalkyl, haloalkoxy or cyano the method comprising:
reacting a compound of formula dd;

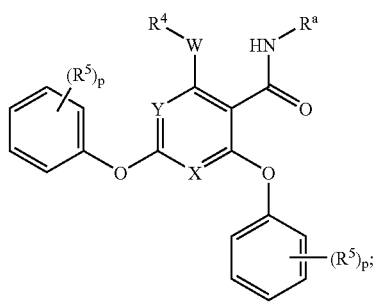

wherein p, W, X, Y, $R^4$, $R^5$ and $R^a$ are as defined herein, with chlorine agent or an anhydride;
followed by treatment with a protected hydrazine (such as BOC-carbazate);
followed by deprotection, to afford the compound of formula ee.

In certain embodiments of the method of making a compound of formula ee, compound dd is treated with chlorine agent to provide a compound of formula ff:

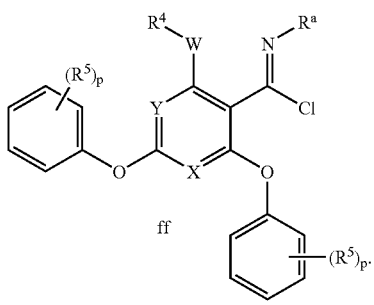

ff

In certain embodiments of the method of making a compound of formula ee, the chlorine agent is thionyl chloride.

In certain embodiments of the method of making a compound of formula ee, treatment with the protected hydrazine is carried out on compound ff to afford a compound of formula hh:

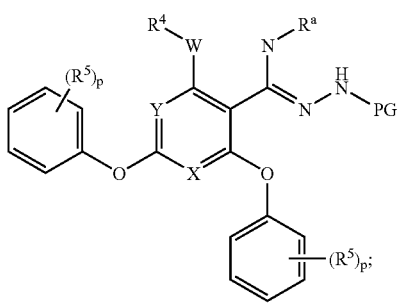

hh wherein PG is a protecting group such as BOC, and p, W, X, Y, $R^4$, $R^5$ and $R^a$ are as defined herein.

In certain embodiments of the method of making a compound of formula ee, deprotection is carried out by treatment of compound hh with acid to provide the compound of formula ee. The acid may comprise, for example, trifluoroacetic acid.

In certain embodiments of the method of making a compound of formula ee, the method further comprises:

reacting a compound of formula bb:

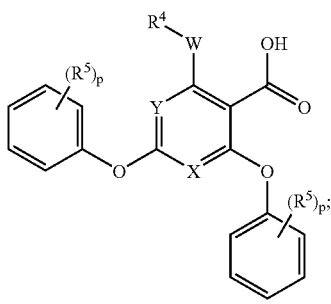

bb wherein p, W, X, Y, $R^4$, and $R^5$ are as defined herein, with chlorine agent, followed by an amine of formula $R^a$—$NH_2$, to provide the compound of formula dd. The chlorine agent may comprise thionyl chloride.

In certain embodiments of the method of making a compound of formula ee, the method further comprises reacting a compound of formula aa:

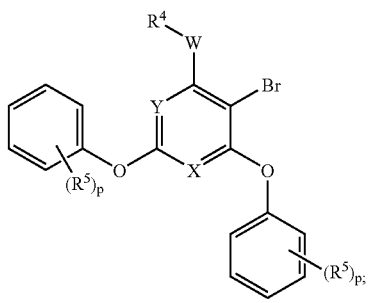

aa wherein p, W, X, Y, $R^4$ and $R^5$ are as defined herein, with a Grignard reagent, followed by carbon dioxide, to provide the compound of formula bb.

The invention also provides a compound of formula dd:

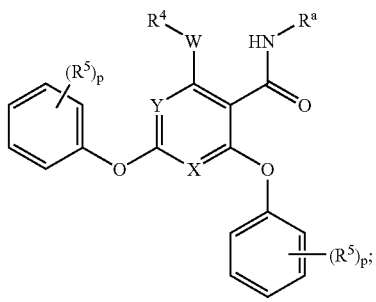

dd or pharmaceutically acceptable salts thereof, wherein:

p is from 0 to 4;

one of X and Y is N and the other is CH, or X and Y are both N;

W is O, $NR'^{11}$, or a bond wherein $R^f$ is hydrogen, alkyl or a protecting group;

$R^a$ is $C_{1-6}$alkyl, $C_{3-7}$cycloalkyl, $C_{3-7}$cycloalkyl-$C_{1-4}$alkyl, $C_{3-7}$cycloalkenyl, $C_{3-7}$cycloalkenyl-$C_{1-6}$alkyl, halo-$C_{1-6}$alkyl, halo-$C_{3-7}$cycloalkyl, hydroxy-$C_{1-6}$alkyl, $C_{1-6}$alkylsulfonyl$C_{1-6}$alkyl, $C_{1-6}$alkylsulfanyl-$C_{1-6}$alkyl, arylsulfonyl-$C_{1-6}$ alkyl, aryl, aryl-$C_{1-6}$alkyl, heteroaryl, heteroaryl-$C_{1-6}$ alkyl, $C_{1-6}$alkylsulfonamidyl$C_{1-6}$alkyl, $C_{1-6}$alkoxycarbonylamino-$C_{1-6}$alkyl, $C_{1-6}$alkoxycarbonyl-$C_{1-6}$alkyl, $C_{1-6}$alkoxyaminocarbonyl-$C_{1-6}$alkyl, aminocarbonyl-$C_{1-6}$ alkyl, $C_{1-6}$alkylaminocarbonyl-$C_{1-6}$alkyl, carboxy-$C_{1-6}$alkyl, heterocyclyl, heterocyclylalkyl, $C_{1-6}$alkylcarbonyl-$C_{1-6}$alkyl, heterocyclyl-$C_{1-6}$alkyl, aryl-$C_{1-6}$alkyl, amino-$C_{1-6}$alkyl, N—$C_{1-6}$alkylamino-$C_{1-6}$alkyl, N,N-di-$C_{1-6}$-alkylamino-$C_{1-6}$alkyl, $C_{1-6}$alkoxy-$C_{1-6}$alkyl, or heteroaryl-$C_{1-6}$ alkyl, $R^4$ is hyrdogen, hydroxyalkyl, alkoxyalkyl or alkylsulfonylalkyl; and $R^5$ is halo, alkyl, alkoxy, haloalkyl, haloalkoxy or cyano.

The invention also provides a compound of formula hh:

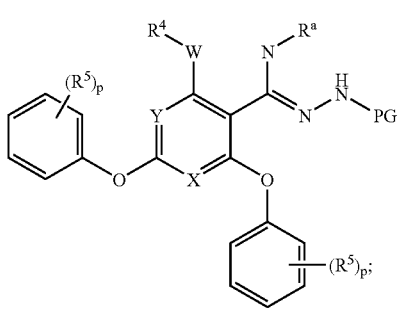

or pharmaceutically acceptable salts thereof, wherein:
p is from 0 to 4;
one of X and Y is N and the other is CH, or X and Y are both N;
W is O, $NR^f$, or a bond wherein $R^f$ is hydrogen, alkyl or a protecting group;
PG is a protecting group;
$R^a$ is $C_{1-6}$alkyl, $C_{3-7}$cycloalkyl, $C_{3-7}$cycloalkyl-$C_{1-4}$alkyl, $C_{3-7}$cycloalkenyl, $C_{3-7}$cycloalkenyl-$C_{1-4}$alkyl, halo-$C_{1-6}$alkyl, halo-$C_{3-7}$cycloalkyl, hydroxy-$C_{1-6}$alkyl, $C_{1-6}$alkylsulfonyl$C_{1-6}$alkyl, $C_{1-6}$alkylsulfanyl-$C_{1-6}$alkyl, arylsulfonyl-$C_{1-6}$ alkyl, aryl, aryl-$C_{1-6}$alkyl, heteroaryl, heteroaryl-$C_{1-6}$alkyl, $C_{1-6}$alkylsulfonamidyl$C_{1-6}$alkyl, $C_{1-6}$alkoxycarbonylamino-$C_{1-6}$alkyl, $C_{1-6}$-alkoxycarbonyl-$C_{1-6}$alkyl, $C_{1-6}$alkoxyaminocarbonyl-$C_{1-6}$alkyl, aminocarbonyl-$C_{1-6}$alkyl, $C_{1-6}$alkylaminocarbonyl-$C_{1-6}$alkyl, carboxy-$C_{1-6}$alkyl, heterocyclyl, heterocyclylalkyl, $C_{1-6}$alkylcarbonyl-$C_{1-6}$ alkyl, heterocyclyl-$C_{1-6}$alkyl, aryl-$C_{1-6}$alkyl, amino-$C_{1-6}$alkyl, N—$C_{1-6}$alkylamino-$C_{1-6}$alkyl, N,N-di-$C_{1-6}$alkylamino-$C_{1-6}$alkyl, $C_{1-6}$alkoxy-$C_{1-6}$alkyl, or heteroaryl-$C_{1-6}$ alkyl,
$R^4$ is hyrdogen, hydroxyalkyl, alkoxyalkyl or alkylsulfonylalkyl; and
$R^5$ is halo, alkyl, alkoxy, haloalkyl, haloalkoxy or cyano.

In certain embodiments of formula dd, formula ee, formula ff or formula hh, p is 1 or 2, $R^5$ is halo, W is a bond, X and Y are N, $R^4$ is hydrogen, and $R^a$ is $C_{1-6}$alkyl, $C_{3-7}$cycloalkyl, $C_{3-7}$cycloalkyl-$C_{1-4}$alkyl, $C_{3-7}$cycloalkenyl, $C_{3-7}$cycloalkenyl-$C_{1-4}$alkyl, halo-$C_{1-6}$alkyl, halo-$C_{3-7}$cycloalkyl, hydroxy-$C_{1-6}$alkyl, $C_{1-6}$alkylsulfonyl$C_{1-6}$alkyl, $C_{1-6}$alkylsulfanyl-$C_{1-6}$alkyl, arylsulfonyl-$C_{1-6}$alkyl, aryl, aralkyl, heteroaryl, heteroaralkyl, $C_{1-6}$alkylsulfonamidyl$C_{1-6}$alkyl, $C_{1-6}$alkoxycarbonylamino-$C_{1-6}$alkyl, $C_{1-6}$alkoxycarbonyl-$C_{1-6}$alkyl, $C_{1-6}$alkoxyaminocarbonyl-$C_{1-6}$alkyl, aminocarbonyl-$C_{1-6}$alkyl, $C_{1-6}$alkylaminocarbonyl-$C_{1-6}$alkyl, carboxy-$C_{1-6}$alkyl, heterocyclyl, heterocyclylalkyl, $C_{1-6}$alkylcarbonyl-$C_{1-6}$alkyl, heterocyclyl-$C_{1-6}$alkyl, aryl-$C_{1-6}$alkyl, amino-$C_{1-6}$alkyl, N—$C_{1-6}$alkylamino-$C_{1-6}$alkyl, N,N-di-$C_{1-6}$alkylamino-$C_{1-6}$alkyl, or heteroaryl-$C_{1-4}$alkyl.

In certain embodiments of formula dd, formula ee, formula ff or formula hh, p is 1 or 2, $R^5$ is halo, W is a bond, X and Y are N, $R^4$ is hydrogen, and $R^a$ is $C_{1-6}$alkyl, $C_{3-7}$cycloalkyl-$C_{1-4}$alkyl, hydroxy-$C_{1-6}$alkyl, $C_{1-6}$-alkylsulfonyl$C_{1-6}$alkyl, $C_{1-6}$-alkylsulfanyl-$C_{1-6}$alkyl, arylsulfonyl-$C_{1-6}$alkyl, heterocyclyl, heteroaryl-$C_{1-6}$alkyl or heterocyclyl-$C_{1-4}$alkyl.

In certain embodiments of formula dd, formula ee, formula ff or formula hh, p is 1 or 2, $R^5$ is halo, W is a bond, X and Y are N, $R^4$ is hydrogen, and $R^a$ is $C_{1-6}$alkyl, $C_{3-7}$cycloalkyl, or $C_{1-6}$alkylsulfonyl-$C_{1-6}$alkyl.

In certain embodiments of formula dd, formula ee, formula ff or formula hh, p is 1 or 2, $R^5$ is halo, W is a bond, X and Y are N, $R^4$ is hydrogen, and $R^a$ is $C_{1-6}$alkylsulfonyl-$C_{1-6}$alkyl.

In certain embodiments of formula dd, formula ee, formula ff or formula hh, p is 1 or 2, $R^5$ is halo, W is a bond, X and Y are N, $R^4$ is hydrogen, and $R^a$ is heterocyclyl selected from tetrahydropyranyl, tetrahydrothiopyranyl, tetrahydrothiophenyl and piperidinyl.

In certain embodiments of formula dd, formula ee, formula ff or formula hh, p is 1 or 2, $R^5$ is halo, W is a bond, X and Y are N, $R^4$ is hydrogen, and $R^a$ is heterocyclyl selected from tetrahydropyran-4-yl, tetrahydro-thiopyran-3-yl, 1,1-dioxohexahydro-1lambda*6*-thiopyran-3-yl, 1,1-dioxo-hexahydro-1lambda*6*-thiopyran-4-yl, 1,1-dioxo-tetrahydro-1lambda*6*-thiophen-3-yl, piperidin-4-yl and 1-acetyl-piperidin-4-yl.

In certain embodiments of formula dd, formula ee, formula ff or formula hh, p is 1 or 2, $R^5$ is halo, W is a bond, X and Y are N, $R^4$ is hydrogen, and $R^a$ is heteroaryl-$C_{1-6}$alky selected from tetrazolyl-$C_{1-6}$alkyl and trIIzolyl-$C_{1-6}$alkyl.

In certain embodiments of formula dd, formula ee, formula ff or formula hh, p is 1 or 2, $R^5$ is halo, X and Y are N, W is a bond, $R^4$ is hydrogen, and $R^a$ is heteroaryl$C_{1-6}$alky selected from 1-methyl-2-tetrazol-2-yl-ethyl and 1-methyl-2-[1,2,3] trIIzol-2-yl-ethyl.

In certain embodiments of formula dd, formula ee, formula ff or formula hh, p is 1 or 2, $R^5$ is halo, W is a bond, X and Y are N, $R^4$ is hydrogen, and $R^a$ is heterocyclyl-$C_{1-6}$alkyl selected from pyrrolidin-$C_{1-6}$alkyl and tetrahydrothiophen-$C_{1-6}$alkyl.

In certain embodiments of formula dd, formula ee, formula ff or formula hh, p is 1 or 2, $R^5$ is halo, W is a bond, X and Y are N, $R^4$ is hydrogen, and $R^a$ is heterocyclyl-$C_{1-6}$alkyl selected from pyrrolidin-2-ylmethyl, tetrahydro-thiophen-2-ylmethyl, 1,1-dioxo-tetrahydro-1lambda*6*-thiophen-2-ylmethyl, 1-methanesulfonyl-pyrrolidin-2-ylmethyl, 1-methoxycarbonyl-pyrrolidin-2-ylmethyl and (1,1-dioxo-tetrahydro-1lambda*6*-thiophen-3-ylmethyl.

In certain embodiments of formula dd, formula ee, formula ff or formula hh, p is 1 or 2, $R^5$ is halo, W is a bond, X and Y are N, $R^4$ is hydrogen, and $R^a$ is cyclohexyl or cyclopentyl substituted with $C_{1-6}$alkylsulfonyl.

In certain embodiments of formula dd, formula ee, formula ff or formula hh, p is 1 or 2, $R^5$ is halo, X and Y are N, W is a bond, $R^4$ is hydrogen, and $R^a$ is 2-methanesulfonyl-cyclopentyl.

In certain embodiments of formula dd, formula ee, p is 1 or 2, $R^5$ is halo, W is a bond, X and Y are N, $R^4$ is hydrogen, and $R^a$ is isopropyl or isobutyl.

In certain embodiments of formula dd, formula ee, formula ff or formula hh, p is 1 or 2, $R^5$ is halo, W is a bond, X and Y are N, $R^4$ is hydrogen, and $R^a$ is 2-methanesulfonyl-1-methyl-ethyl, 2-methanesulfonyl-ethyl, 3-methanesulfonyl-propyl, 3-methanesulfonyl-1-methyl-propyl, 3-methanesulfonyl-2-methyl-propyl, 2-ethanesulfonyl-1-methyl-ethyl or 1-methanesulfonylmethyl-propyl.

In certain embodiments of formula dd, formula ee, formula ff or formula hh, p is 1 or 2, $R^5$ is halo, W is a bond, X and Y are N, $R^4$ is hydrogen, and $R^a$ is 2-methanesulfonyl-1-methyl-ethyl.

In certain embodiments of formula dd, formula ee, formula ff or formula hh, p is 1 or 2, $R^5$ is halo, W is a bond, X and Y are N, $R^4$ is hydrogen, and $R^a$ is (R)-2-methanesulfonyl-1-methyl-ethyl.

In certain embodiments of formula dd, formula ee, formula ff or formula hh, p is 1 or 2, $R^5$ is halo, W is a bond, X and Y are N, $R^4$ is hydrogen, and $R^a$ is (S)-2-methanesulfonyl-1-methyl-ethyl.

In certain embodiments of formula dd, formula ee, formula ff or formula hh, p is 1 or 2, $R^5$ is halo, W is a bond, X and Y are N, $R^4$ is hydrogen, and $R^a$ is isopropyl.

The invention also provides a method for making a compound of formula oo;

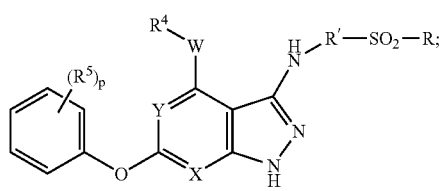

oo wherein:

p is from 0 to 4;

one of X and Y is N and the other is CH, or X and Y are both N;

W is O, $NR^f$, or a bond wherein $R^f$ is hydrogen, alkyl or a protecting group;

$R^a$ is $C_{1-6}$alkyl, $C_{3-7}$cycloalkyl, $C_{3-7}$cycloalkyl-$C_{1-4}$alkyl, $C_{3-7}$cycloalkenyl, $C_{3-7}$cycloalkenyl-$C_{1-4}$alkyl, halo-$C_{1-6}$alkyl, halo-$C_{3-7}$cycloalkyl, hydroxy-$C_{1-6}$alkyl, $C_{1-6}$alkylsulfonyl$C_{1-6}$alkyl, $C_{1-6}$alkylsulfanyl-$C_{1-6}$alkyl, arylsulfonyl-$C_{1-6}$ alkyl, aryl, aryl-$C_{1-6}$alkyl, heteroaryl, heteroaryl-$C_{1-6}$ alkyl, $C_{1-6}$alkylsulfonamidyl$C_{1-6}$alkyl, $C_{1-4}$alkoxycarbonylamino-$C_{1-6}$alkyl, $C_{1-6}$alkoxycarbonyl-$C_{1-6}$alkyl, $C_{1-6}$alkoxyaminocarbonyl-$C_{1-6}$alkyl, aminocarbonyl-$C_{1-6}$ alkyl, $C_{1-6}$alkylaminocarbonyl-$C_{1-6}$alkyl, carboxy-$C_{1-6}$alkyl, heterocyclyl, heterocyclylalkyl, $C_{1-6}$alkylcarbonyl-$C_{1-6}$ alkyl, heterocyclyl-$C_{1-6}$alkyl, aryl-$C_{1-6}$alkyl, amino-$C_{1-6}$ alkyl, N—$C_{1-6}$alkylamino-$C_{1-6}$alkyl, N,N-di-$C_{1-6}$-alkylamino-$C_{1-6}$alkyl, $C_{1-6}$alkoxy-$C_{1-6}$alkyl, or heteroaryl-$C_{1-6}$ alkyl, $R^4$ is hyrdogen, hydroxyalkyl, alkoxyalkyl or alkylsulfonylalkyl;

$R^5$ is halo, alkyl, alkoxy, haloalkyl, haloalkoxy or cyano;

R is $C_{1-6}$alkyl; and $R^1$ is $C_{1-6}$alkylene, the method comprising:

reacting a compound of formula nn:

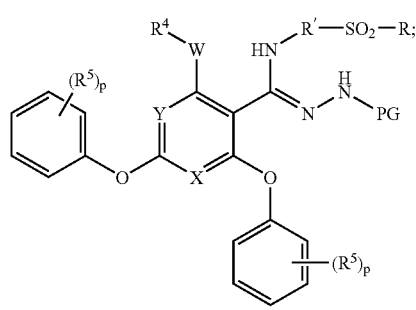

nn wherein PG is a protecting group and p, W, X, Y, $R^4$, $R^5$, R and R' are as defined herein, with acid, to provide the compound of formula oo.

In certain embodiments of method for making a compound of formula oo, the acid may be trifluoroacetic acid.

In certain embodiments of method for making a compound of formula oo, the method further comprises:

reacting a compound of formula mm:

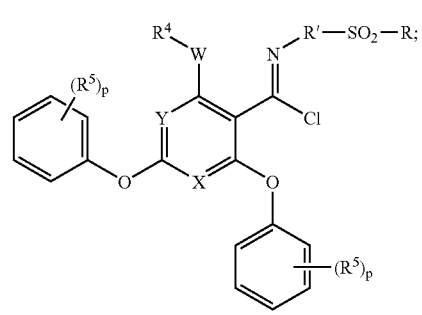

mm wherein p, W, X, Y, $R^4$, $R^5$, R and R' are as defined herein with a protected hydrazine of the formula $H_2N$—NH-PG, to provide the compound of formula nn. The protecting group may be BOC.

In certain embodiments of method for making a compound of formula oo, the method further comprises:

reacting a compound of formula kk:

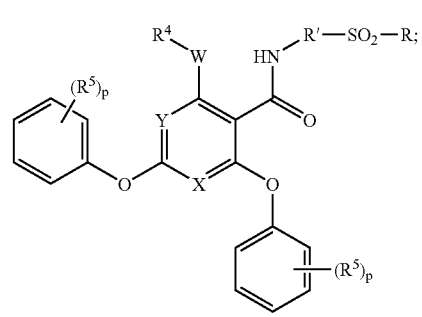

kk wherein p, W, X, Y, $R^4$, $R^5$, R and R' are as defined herein, with a chlorine agent, to provide the compound of formula mm. The chlorine agent may comprise thionyl chloride.

In certain embodiments of method for making a compound of formula oo, the method further comprises:

oxidizing a compound of formula jj:

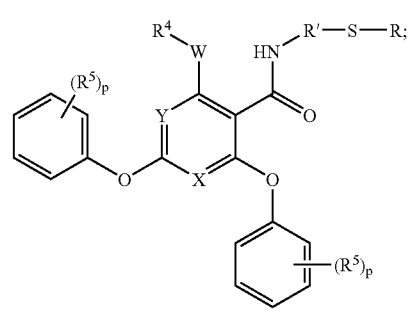

jj wherein p, W, X, Y, $R^4$, $R^5$, R and R' are as defined herein to provide the compound of formula kk. The oxidizing may be carried out with hydrogen peroxide or peracid.

In certain embodiments of method for making a compound of formula oo, the method further comprises:

reacting a compound of formula aa:

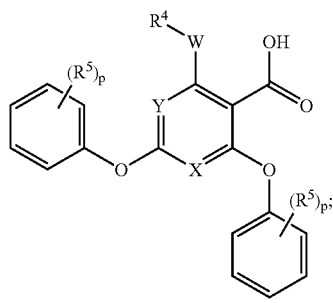

bb wherein p, W, X, Y, $R^4$ and $R^5$ are as defined herein with a chlorine agent, followed by an amine of the formula R—S—R'—$NH_2$, to provide the compound of formula jj. The chlorine agent may be thionyl chloride.

The invention also provides compounds of the formula kk;

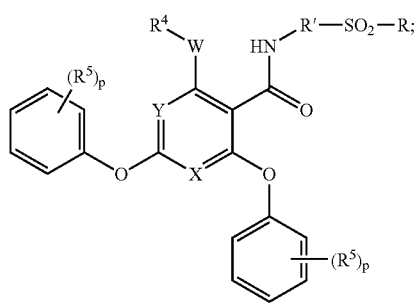

kk or pharmaceutically acceptable salts thereof, wherein:

p is from 0 to 4;

one of X and Y is N and the other is CH, or X and Y are both N;

W is O, $NR^f$, or a bond wherein $R^f$ is hydrogen, alkyl or a protecting group;

$R^a$ is $C_{1-6}$alkyl, $C_{3-7}$cycloalkyl, $C_{3-7}$cycloalkyl-$C_{1-4}$alkyl, $C_{3-7}$cycloalkenyl, $C_{3-7}$cycloalkenyl-$C_{1-4}$alkyl, halo-$C_{1-6}$alkyl, halo-$C_{3-7}$cycloalkyl, hydroxy-$C_{1-6}$alkyl, $C_{1-6}$alkylsulfonyl$C_{1-6}$alkyl, $C_{1-6}$alkylsulfanyl-$C_{1-6}$alkyl, arylsulfonyl-$C_{1-6}$ alkyl, aryl, aryl-$C_{1-6}$alkyl, heteroaryl, heteroaryl-$C_{1-6}$alkyl, $C_{1-6}$alkylsulfonamidyl$C_{1-6}$alkyl, $C_{1-6}$alkoxycarbonylamino-$C_{1-6}$alkyl, $C_{1-6}$alkoxycarbonyl-$C_{1-6}$alkyl, $C_{1-6}$alkoxyaminocarbonyl-$C_{1-6}$alkyl, aminocarbonyl-$C_{1-6}$alkyl, $C_{1-6}$alkylaminocarbonyl-$C_{1-6}$alkyl, carboxy-$C_{1-6}$alkyl, heterocyclyl, heterocyclylalkyl, $C_{1-6}$alkylcarbonyl-$C_{1-6}$alkyl, heterocyclyl-$C_{1-6}$alkyl, aryl-$C_{1-6}$alkyl, amino-$C_{1-6}$alkyl, N—$C_{1-6}$alkylamino-$C_{1-6}$alkyl, N,N-di-$C_{1-6}$alkylamino-$C_{1-6}$alkyl, $C_{1-6}$alkoxy-$C_{1-6}$alkyl, or heteroaryl-$C_{1-6}$alkyl, $R^4$ is hyrdogen, hydroxyalkyl, alkoxyalkyl or alkylsulfonylalkyl;

$R^5$ is halo, alkyl, alkoxy, haloalkyl, haloalkoxy or cyano;

R is alkyl; and

R' is alkylene.

The invention also provides compounds of the formula nn;

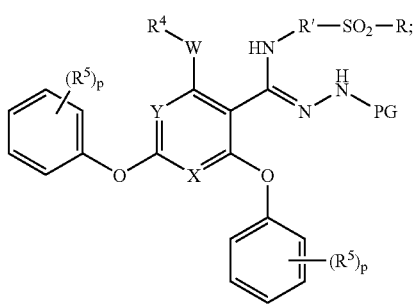

nn or pharmaceutically acceptable salts thereof, wherein:

p is from 0 to 4;

one of X and Y is N and the other is CH, or X and Y are both N;

W is O, $NR^f$, or a bond wherein $R^f$ is hydrogen, alkyl or a protecting group;

PG is a protecting group;

$R^a$ is $C_{1-6}$alkyl, $C_{3-7}$cycloalkyl, $C_{3-7}$cycloalkyl-$C_{1-4}$alkyl, $C_{3-7}$cycloalkenyl, $C_{3-7}$cycloalkenyl-$C_{1-4}$alkyl, halo-$C_{1-6}$alkyl, halo-$C_{3-7}$cycloalkyl, hydroxy-$C_{1-6}$alkyl, $C_{1-6}$alkylsulfonyl$C_{1-6}$alkyl, $C_{1-6}$alkylsulfanyl-$C_{1-6}$alkyl, arylsulfonyl-$C_{1-6}$ alkyl, aryl, aryl-$C_{1-6}$alkyl, heteroaryl, heteroaryl-$C_{1-6}$alkyl, $C_{1-6}$alkylsulfonamidyl$C_{1-6}$alkyl, $C_{1-6}$alkoxycarbonylamino-$C_{1-6}$alkyl, $C_{1-6}$alkoxycarbonyl-$C_{1-6}$alkyl, $C_{1-6}$alkoxyaminocarbonyl-$C_{1-6}$alkyl, aminocarbonyl-$C_{1-6}$alkyl, $C_{1-6}$alkylaminocarbonyl-$C_{1-6}$alkyl, carboxy-$C_{1-6}$alkyl, heterocyclyl, heterocyclylalkyl, $C_{1-6}$alkylcarbonyl-$C_{1-6}$alkyl, heterocyclyl-$C_{1-6}$alkyl, aryl-$C_{1-6}$alkyl, amino-$C_{1-6}$alkyl, N—$C_{1-6}$alkylamino-$C_{1-4}$alkyl, N,N-di-$C_{1-6}$alkylamino-$C_{1-6}$alkyl, $C_{1-6}$alkoxy-$C_{1-6}$alkyl, or heteroaryl-$C_{1-6}$alkyl, $R^4$ is hyrdogen, hydroxyalkyl, alkoxyalkyl or alkylsulfonylalkyl;

$R^5$ is halo, alkyl, alkoxy, haloalkyl, haloalkoxy or cyano;

R is alkyl; and

R' is alkylene.

The invention also provides compounds of the formula jj;

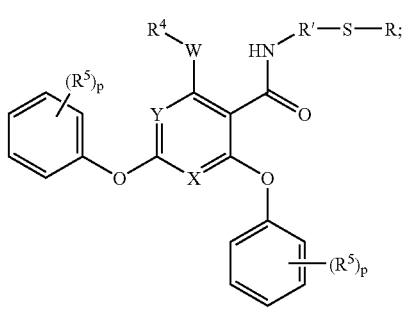

jj or pharmaceutically acceptable salts thereof, wherein:
  p is from 0 to 4;
  one of X and Y is N and the other is CH, or X and Y are both N;
  W is O, $NR^f$, or a bond wherein $R^f$ is hydrogen, alkyl or a protecting group;
  $R^a$ is $C_{1-6}$alkyl, $C_{3-7}$cycloalkyl, $C_{3-7}$cycloalkyl-$C_{1-4}$alkyl, $C_{3-7}$cycloalkenyl, $C_{3-7}$cycloalkenyl-$C_{1-6}$alkyl, halo-$C_{1-6}$alkyl, halo-$C_{3-7}$cycloalkyl, hydroxy-$C_{1-6}$alkyl, $C_{1-6}$alkylsulfonyl$C_{1-6}$alkyl, $C_{1-6}$alkylsulfanyl-$C_{1-6}$alkyl, arylsulfonyl-$C_{1-6}$ alkyl, aryl, aryl-$C_{1-6}$alkyl, heteroaryl, heteroaryl-$C_{1-6}$alkyl, $C_{1-6}$alkylsulfonamidyl$C_{1-6}$alkyl, $C_{1-6}$alkoxycarbonylamino-$C_{1-6}$alkyl, $C_{1-6}$alkoxycarbonyl-$C_{1-6}$alkyl, $C_{1-6}$alkoxyaminocarbonyl-$C_{1-6}$alkyl, aminocarbonyl-$C_{1-6}$alkyl, $C_{1-6}$-alkylaminocarbonyl-$C_{1-6}$alkyl, carboxy-$C_{1-6}$alkyl, heterocyclyl, heterocyclylalkyl, $C_{1-6}$alkylcarbonyl-$C_{1-6}$ alkyl, heterocyclyl-$C_{1-6}$alkyl, aryl-$C_{1-6}$alkyl, amino-$C_{1-6}$ alkyl, N—$C_{1-6}$alkylamino-$C_{1-6}$alkyl, N,N-di-$C_{1-6}$alkylamino-$C_{1-6}$alkyl, $C_{1-6}$alkoxy-$C_{1-6}$alkyl, or heteroaryl-$C_{1-6}$alkyl,
  $R^4$ is hyrdogen, hydroxyalkyl, alkoxyalkyl or alkylsulfonylalkyl;
  $R^5$ is halo, alkyl, alkoxy, haloalkyl, haloalkoxy or cyano;
  R is alkyl; and
  R' is alkylene.

In certain embodiments of formula jj, formula kk, formula mm, formula nn or formula oo, p is 1 or 2, $R^5$ is halo, W is a bond, X and Y are N, and $R^4$ is hydrogen.

In embodiments of the invention where any of $R^1$, $R^2$, $R^3$, $R^4$, $R^5$, $R^6$, $R^a$, $R^b$, $R^c$, $R^d$, $R^e$, $R^f$, $R^g$, $R^h$ or $R^i$ is alkyl or contains an alkyl moiety, such alkyl is preferably lower alkyl, i.e. $C_1$-$C_6$alkyl, and more preferably $C_1$-$C_4$alkyl.

Where $R_2$ contains a heteroaryl moiety, and where $R^a$ is heteroaryl or contains a heteroaryl moiety, such heteroaryl may be a five or six membered monocyclic heteroaryl that contains one or two heteroatoms selected from O, N and S. Heteroaryl may include, for example, furanyl, thienyl pyrrolyl, imidazolyl, pyrazolyl, oxazolyl, thiazolyl, pyridinyl or pyrimdinyl, and more preferably furanyl, thienyl or pyridinyl.

Where $R^4$ is heteroalkyl, such heteroalkyl may be hydroxyalkyl, aminoalkyl or alkylsulfonylalkyl.

Pharmaceutically acceptable acid addition salts of the compounds of Formula I include salts derived from inorganic acids such as hydrochloric, nitric, phosphoric, sulfuric, hydrobromic, hydriodic, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharmaceutical Science*, 1977, 66, 1-19).

The acid addition salts of the basic compounds can be prepared by contacting the free base form with a sufficient amount of the desired acid to produce the salt in the conventional manner. The free base form can be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Representative compounds in accordance with one aspect of the invention are shown below in Table 1.

TABLE 1

| # | Structure | Name (Autonom ™) | MP (° C.) or M+ H |
|---|---|---|---|
| 1 | 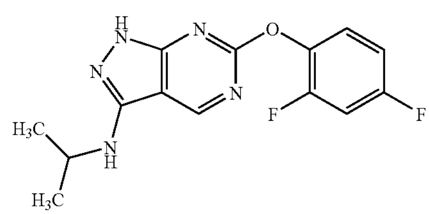 | [6-(2,4-Difluoro-phenoxy)-1H-pyrazolo[3,4-d]pyrimidin-3-yl]-isopropyl-amine | 211.3-212.4 |
| 2 | 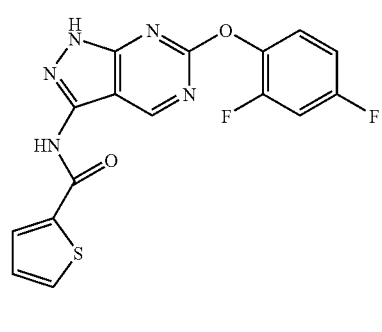 | Thiophene-2-carboxylic acid [6-(2,4-difluoro-phenoxy)-1H-pyrazolo[3,4-d]pyrimidin-3-yl]-amide | 255.4-256.2 |

TABLE 1-continued

| # | Structure | Name (Autonom ™) | MP (° C.) or M+ H |
|---|---|---|---|
| 3 | 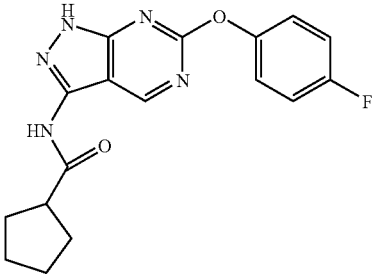 | Cyclopentanecarboxylic acid [6-(4-fluoro-phenoxy)-1H-pyrazolo[3,4-d]pyrimidin-3-yl]-amide | 220.1-221.7 |
| 4 | 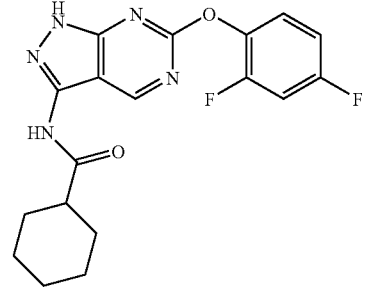 | Cyclohexanecarboxylic acid [6-(2,4-difluoro-phenoxy)-1H-pyrazolo[3,4-d]pyrimidin-3-yl]-amide | 214.4-215.3 |
| 5 | 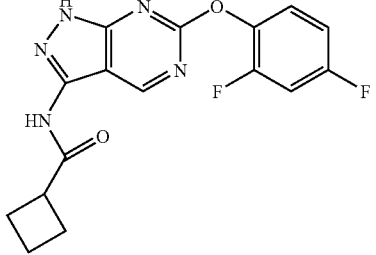 | Cyclobutanecarboxylic acid [6-(2,4-difluoro-phenoxy)-1H-pyrazolo[3,4-d]pyrimidin-3-yl]-amide | 248.2-248.6 |
| 6 | 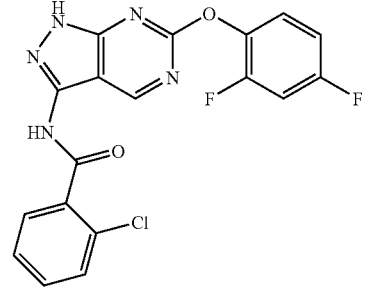 | 2-Chloro-N-[6-(2,4-difluoro-phenoxy)-1H-pyrazolo[3,4-d]pyrimidin-3-yl]-benzamide | 194.5-195.6 |
| 7 | 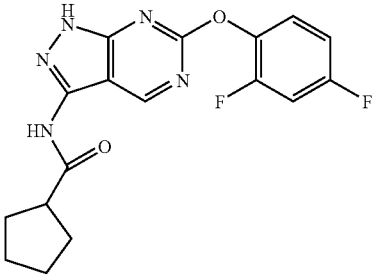 | Cyclopentanecarboxylic acid [6-(2-fluoro-phenoxy)-1H-pyrazolo[3,4-d]pyrimidin-3-yl]-amide | 162.0-163.7 |

TABLE 1-continued
| # | Structure | Name (Autonom ™) | MP (° C.) or M+ H |
|---|---|---|---|
| 8 | 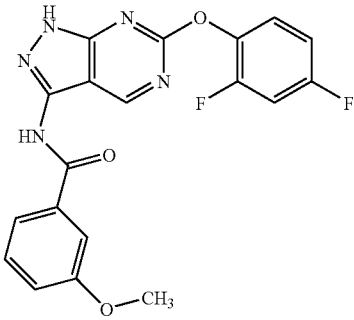 | N-[6-(2,4-Difluoro-phenoxy)-1H-pyrazolo[3,4-d]pyrimidin-3-yl]-3-methoxy-benzamide | 247.9-249.1 |
| 9 | 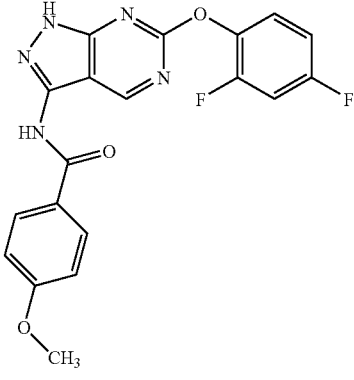 | N-[6-(2,4-Difluoro-phenoxy)-1H-pyrazolo[3,4-d]pyrimidin-3-yl]-4-methoxy-benzamide | 266.1-267.3 |
| 10 | 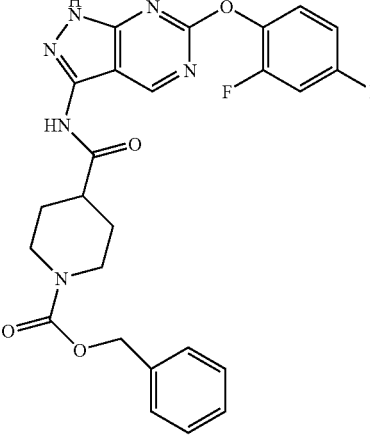 | 4-[6-(2,4-Difluoro-phenoxy)-1H-pyrazolo[3,4-d]pyrimidin-3-ylcarbamoyl]-piperidine-1-carboxylic acid benzyl ester | 215.0-216.9 |
| 11 | 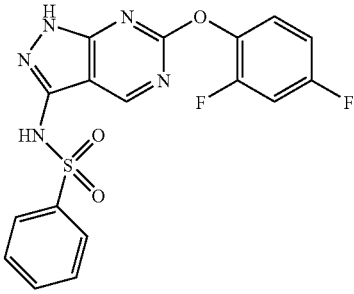 | N-[6-(2,4-Difluoro-phenoxy)-1H-pyrazolo[3,4-d]pyrimidin-3-yl]-benzenesulfonamide | 198.6-199.9 |

TABLE 1-continued

| # | Structure | Name (Autonom ™) | MP (° C.) or M+ H |
|---|---|---|---|
| 12 | 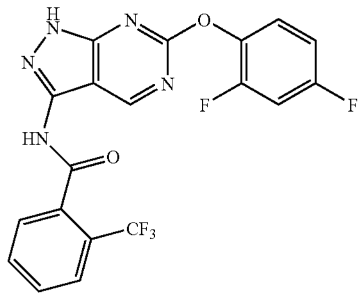 | N-[6-(2,4-Difluoro-phenoxy)-1H-pyrazolo[3,4-d]pyrimidin-3-yl]-2-trifluoromethyl-benzamide | 128.7-130.5 |
| 13 | 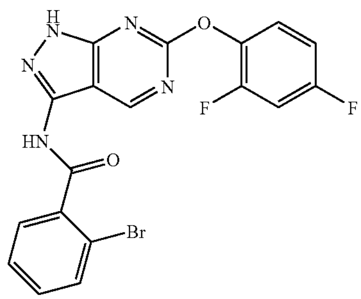 | 2-Bromo-N-[6-(2,4-difluoro-phenoxy)-1H-pyrazolo[3,4-d]pyrimidin-3-yl]-benzamide | 107.3-108.9 |
| 14 | 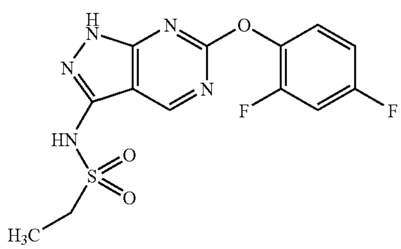 | Ethanesulfonic acid [6-(2,4-difluoro-phenoxy)-1H-pyrazolo[3,4-d]pyrimidin-3-yl]-amide | 226.0-226.9 |
| 15 | 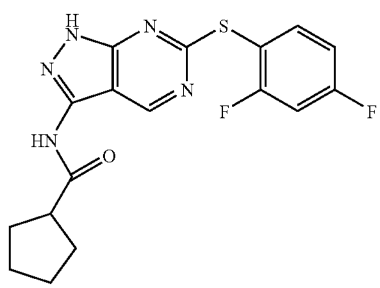 | Cyclopentanecarboxylic acid [6-(2,4-difluoro-phenylsulfanyl)-1H-pyrazolo[3,4-d]pyrimidin-3-yl]-amide | 201.4-203.5 |
| 16 | 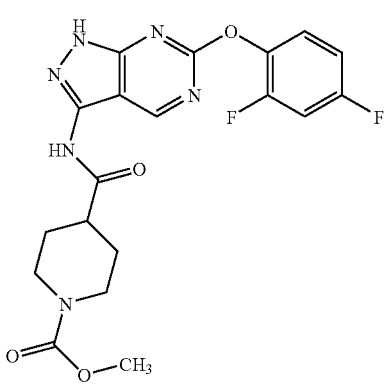 | 4-[6-(2,4-Difluoro-phenoxy)-1H-pyrazolo[3,4-d]pyrimidin-3-ylcarbamoyl]-piperidine-1-carboxylic acid methyl ester | 205.1-206.8 |

TABLE 1-continued

| # | Structure | Name (Autonom ™) | MP (° C.) or M+ H |
|---|---|---|---|
| 17 | 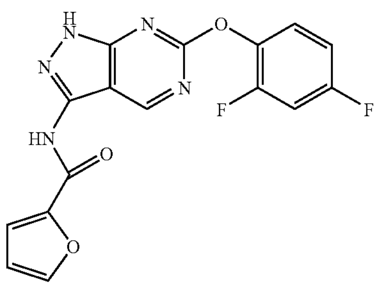 | Furan-2-carboxylic acid [6-(2,4-difluoro-phenoxy)-1H-pyrazolo[3,4-d]pyrimidin-3-yl]-amide | 221.9-223.0 |
| 18 | 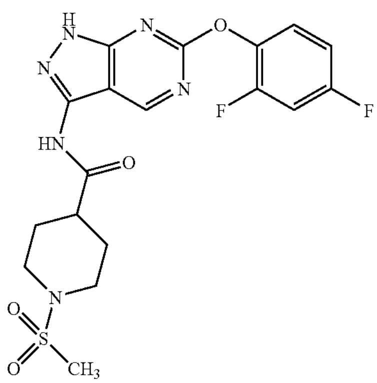 | 1-Methanesulfonyl-piperidine-4-carboxylic acid [6-(2,4-difluoro-phenoxy)-1H-pyrazolo[3,4-d]pyrimidin-3-yl]-amide | 453 |
| 19 | 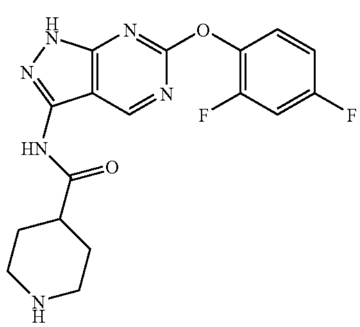 | Piperidine-4-carboxylic acid [6-(2,4-difluoro-phenoxy)-1H-pyrazolo[3,4-d]pyrimidin-3-yl]-amide | >300 |
| 20 | 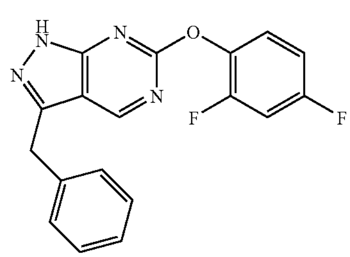 | 3-Benzyl-6-(2,4-difluoro-phenoxy)-1H-pyrazolo[3,4-d]pyrimidine | 339 |
| 21 | 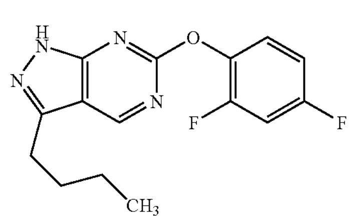 | 3-Butyl-6-(2,4-difluoro-phenoxy)-1H-pyrazolo[3,4-d]pyrimidine | 146.0-147.8 |

TABLE 1-continued

| # | Structure | Name (Autonom ™) | MP (° C.) or M+ H |
|---|---|---|---|
| 22 | 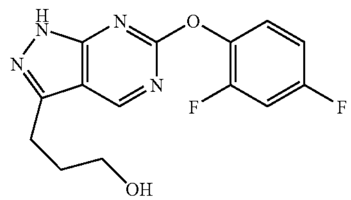 | 3-[6-(2,4-Difluoro-phenoxy)-1H-pyrazolo[3,4-d]pyrimidin-3-yl]-propan-1-ol | 307 |
| 23 | 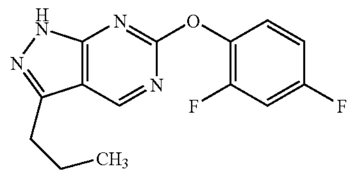 | 6-(2,4-Difluoro-phenoxy)-3-propyl-1H-pyrazolo[3,4-d]pyrimidine | 147.8-148.5 |
| 24 | 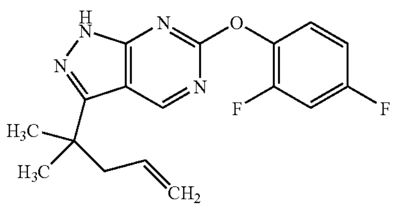 | 6-(2,4-Difluoro-phenoxy)-3-(1,1-dimethyl-but-3-enyl)-1H-pyrazolo[3,4-d]pyrimidine | 331 |
| 25 | 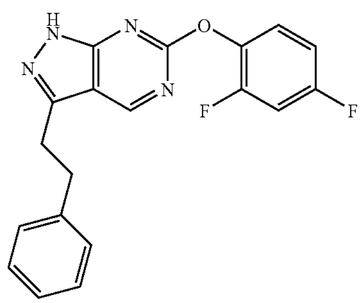 | 6-(2,4-Difluoro-phenoxy)-3-phenethyl-1H-pyrazolo[3,4-d]pyrimidine | 353 |
| 26 | 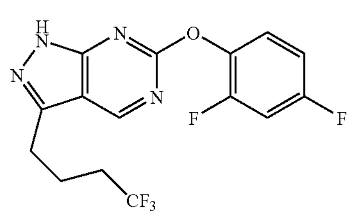 | 6-(2,4-Difluoro-phenoxy)-3-(4,4,4-trifluoro-butyl)-1H-pyrazolo[3,4-d]pyrimidine | 157.1-158.3 |
| 27 | 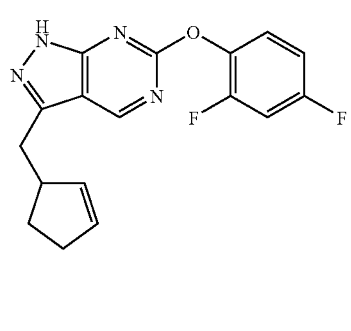 | 3-Cyclopent-2-enylmethyl-6-(2,4-difluoro-phenoxy)-1H-pyrazolo[3,4-d]pyrimidine | 329 |

TABLE 1-continued

| # | Structure | Name (Autonom ™) | MP (° C.) or M+ H |
|---|---|---|---|
| 28 | 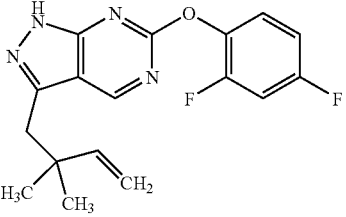 | 6-(2,4-Difluoro-phenoxy)-3-(2,2-dimethyl-but-3-enyl)-1H-pyrazolo[3,4-d]pyrimidine | 331 |
| 29 | 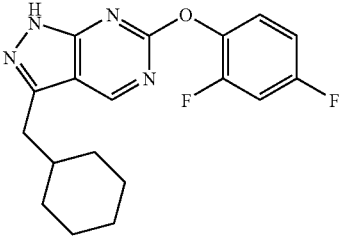 | 3-Cyclohexylmethyl-6-(2,4-difluoro-phenoxy)-1H-pyrazolo[3,4-d]pyrimidine | 61.1-62.1 |
| 30 | 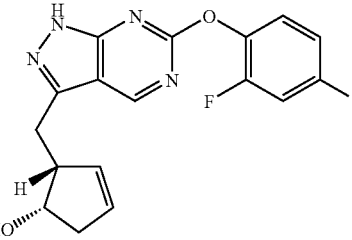 | 2-[6-(2,4-Difluoro-phenoxy)-1H-pyrazolo[3,4-d]pyrimidin-3-ylmethyl]-cyclopent-3-enol | 345 |
| 31 | 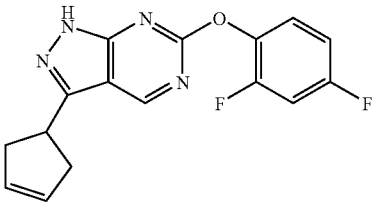 | 3-Cyclopent-3-enyl-6-(2,4-difluoro-phenoxy)-1H-pyrazolo[3,4-d]pyrimidine | 142.6-143.3 |
| 32 | 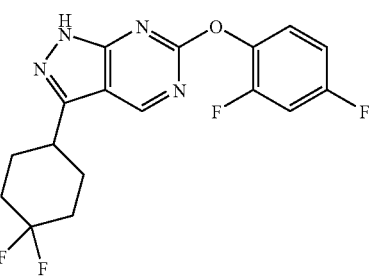 | 3-(4,4-Difluoro-cyclohexyl)-6-(2,4-difluoro-phenoxy)-1H-pyrazolo[3,4-d]pyrimidine | 155.0-156.9 |
| 33 | 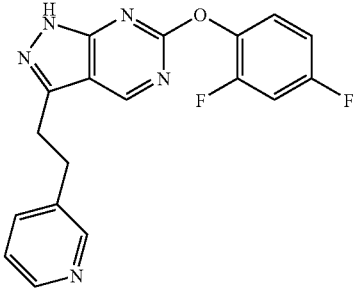 | 6-(2,4-Difluoro-phenoxy)-3-(2-pyridin-3-yl-ethyl)-1H-pyrazolo[3,4-d]pyrimidine | 208.8-209.5 |

TABLE 1-continued

| # | Structure | Name (Autonom ™) | MP (° C.) or M+ H |
|---|---|---|---|
| 34 | 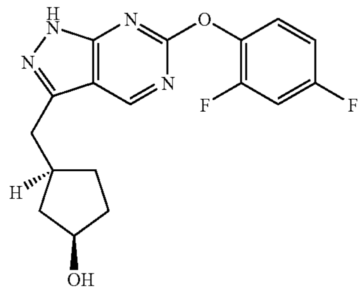 | 3-[6-(2,4-Difluoro-phenoxy)-1H-pyrazolo[3,4-d]pyrimidin-3-ylmethyl]-cyclopentanol | 347 |
| 35 | 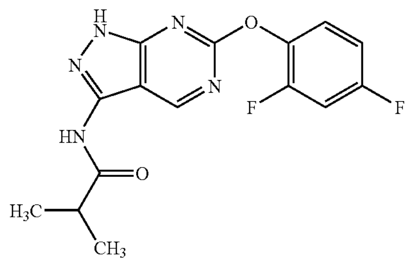 | N-[6-(2,4-Difluoro-phenoxy)-1H-pyrazolo[3,4-d]pyrimidin-3-yl]-isobutyramide | 245.4-246.1 |
| 36 | 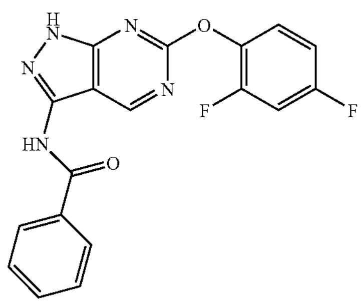 | N-[6-(2,4-Difluoro-phenoxy)-1H-pyrazolo[3,4-d]pyrimidin-3-yl]-benzamide | 266.4-266.6 |
| 37 | 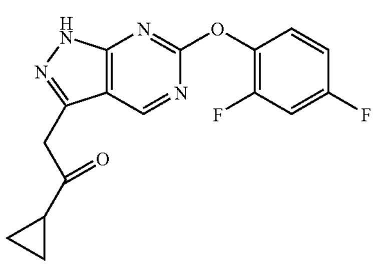 | Cyclopropanecarboxylic acid [6-(2,4-difluoro-phenoxy)-1H-pyrazolo[3,4-d]pyrimidin-3-yl]-amide | >300 |
| 38 | 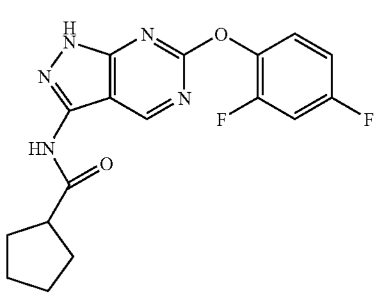 | Cyclopentanecarboxylic acid [6-(2,4-difluoro-phenoxy)-1H-pyrazolo[3,4-d]pyrimidin-3-yl]-amide | 206.3-207.5 |

TABLE 1-continued

| # | Structure | Name (Autonom ™) | MP (° C.) or M+ H |
|---|---|---|---|
| 39 | 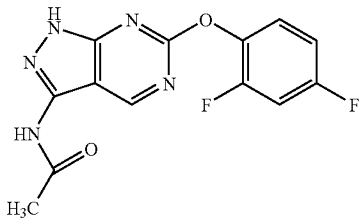 | N-[6-(2,4-Difluoro-phenoxy)-1H-pyrazolo[3,4-d]pyrimidin-3-yl]-acetamide | >300 |
| 40 | 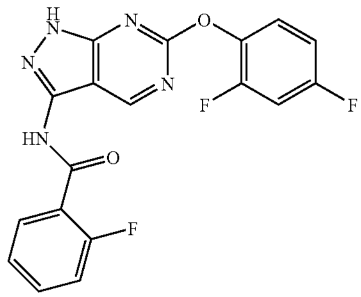 | N-[6-(2,4-Difluoro-phenoxy)-1H-pyrazolo[3,4-d]pyrimidin-3-yl]-2-fluoro-benzamide | 255.3-256.3 |
| 41 | 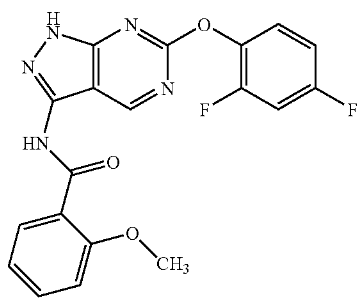 | N-[6-(2,4-Difluoro-phenoxy)-1H-pyrazolo[3,4-d]pyrimidin-3-yl]-2-methoxy-benzamide | 229.6-230.3 |
| 42 | 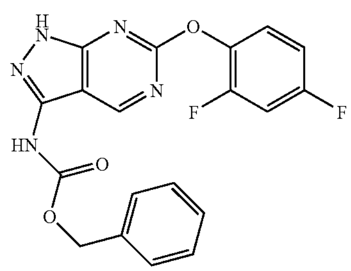 | [6-(2,4-Difluoro-phenoxy)-1H-pyrazolo[3,4-d]pyrimidin-3-yl]-carbamic acid benzyl ester | 270.1-272.0 |
| 43 | 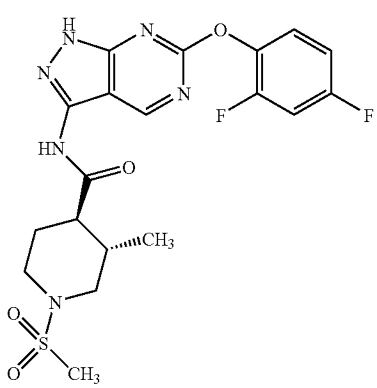 | 1-Methanesulfonyl-3-methyl-piperidine-4-carboxylic acid [6-(2,4-difluoro-phenoxy)-1H-pyrazolo[3,4-d]pyrimidin-3-yl]-amide | 265.0-266.1 |

TABLE 1-continued

| # | Structure | Name (Autonom ™) | MP (° C.) or M+ H |
|---|---|---|---|
| 44 | 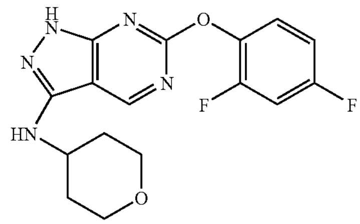 | [6-(2,4-Difluoro-phenoxy)-1H-pyrazolo[3,4-d]pyrimidin-3-yl]-(tetrahydro-pyran-4-yl)-amine | 207.1-208.7 |
| 45 | 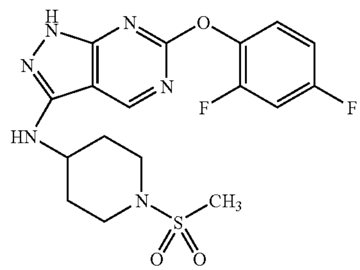 | [6-(2,4-Difluoro-phenoxy)-1H-pyrazolo[3,4-d]pyrimidin-3-yl]-(1-methanesulfonyl-piperidin-4-yl)-amine | 255.5-257.7 |
| 46 | 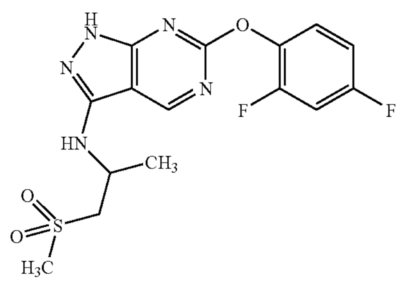 | [6-(2,4-Difluoro-phenoxy)-1H-pyrazolo[3,4-d]pyrimidin-3-yl]-(2-methanesulfonyl-1-methyl-ethyl)-amine | 201.1-205.5 |
| 47 | 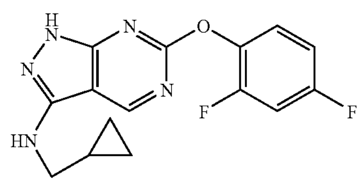 | Cyclopropylmethyl-[6-(2,4-difluoro-phenoxy)-1H-pyrazolo[3,4-d]pyrimidin-3-yl]-amine | 318 |
| 48 | 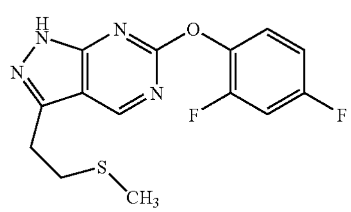 | 6-(2,4-Difluoro-phenoxy)-3-(2-methylsulfanyl-ethyl)-1H-pyrazolo[3,4-d]pyrimidine | 323 |
| 49 | 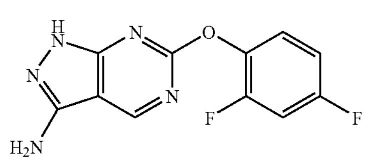 | 6-(2,4-Difluoro-phenoxy)-1H-pyrazolo[3,4-d]pyrimidin-3-ylamine | >300 |

TABLE 1-continued

| # | Structure | Name (Autonom ™) | MP (° C.) or M+ H |
|---|---|---|---|
| 50 | 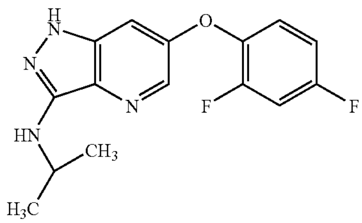 | [6-(2,4-Difluoro-phenoxy)-1H-pyrazolo[4,3-b]pyridin-3-yl]-isopropyl-amine | 305 |
| 51 | 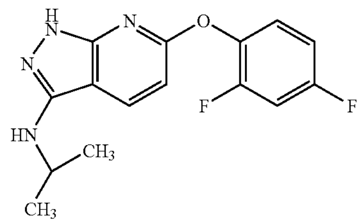 | [6-(2,4-Difluoro-phenoxy)-1H-pyrazolo[3,4-b]pyridin-3-yl]-isopropyl-amine | 305 |
| 52 | 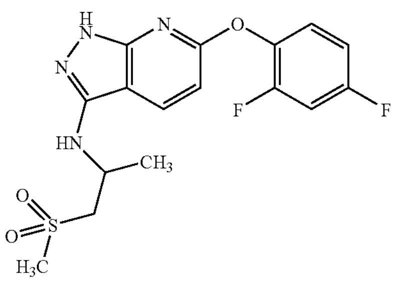 | [6-(2,4-Difluoro-phenoxy)-1H-pyrazolo[3,4-b]pyridin-3-yl]-(2-methanesulfonyl-1-methyl-ethyl)-amine | 383 |
| 53 | 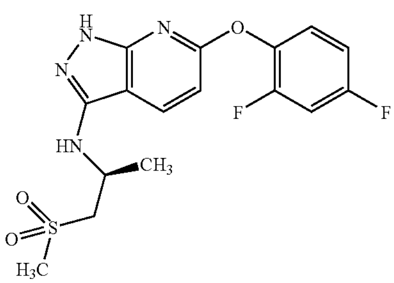 | [6-(2,4-Difluoro-phenoxy)-1H-pyrazolo[3,4-b]pyridin-3-yl]-((S)-2-methanesulfonyl-1-methyl-ethyl)-amine | 98.1-99.3 |
| 54 | 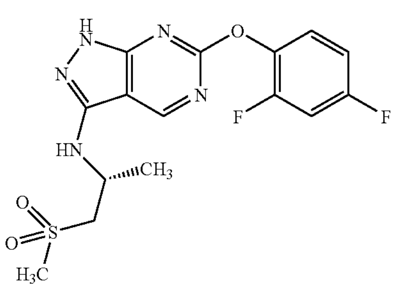 | [6-(2,4-Difluoro-phenoxy)-1H-pyrazolo[3,4-b]pyridin-3-yl]-((R)-2-methanesulfonyl-1-methyl-ethyl)-amine | 98.8-100.3 |

TABLE 1-continued

| # | Structure | Name (Autonom ™) | MP (° C.) or M+ H |
|---|---|---|---|
| 55 | 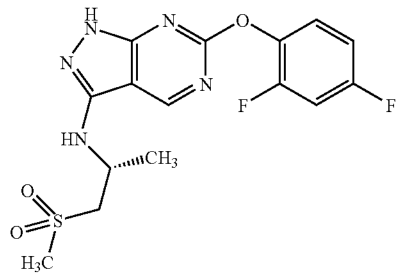 | [6-(2,4-Difluoro-phenoxy)-1H-pyrazolo[3,4-b]pyrimidin-3-yl]-((R)-2-methanesulfonyl-1-methyl-ethyl)-amine | 177.7-178.8 |
| 56 | 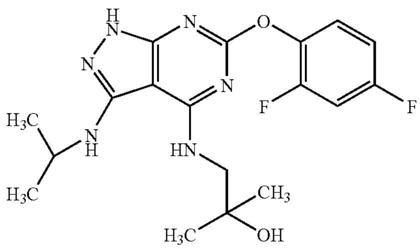 | 1-[6-(2,4-Difluoro-phenoxy)-3-isopropylamino-1H-pyrazolo[3,4-d]pyrimidin-4-ylamino]-2-methyl-propan-2-ol | 393 |
| 57 | 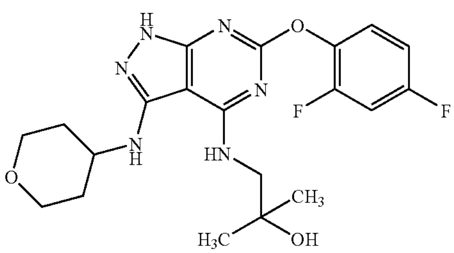 | 1-[6-(2,4-Difluoro-phenoxy)-3-(tetrahydro-pyran-4-ylamino)-1H-pyrazolo[3,4-d]pyrimidin-4-ylamino]-2-methyl-propan-2-ol | 435 |
| 58 | 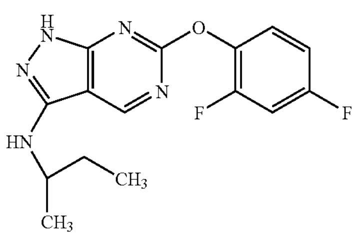 | sec-Butyl-[6-(2,4-difluoro-phenoxy)-1H-pyrazolo[3,4-d]pyrimidin-3-yl]-amine | 178.8-179.9 |
| 59 | 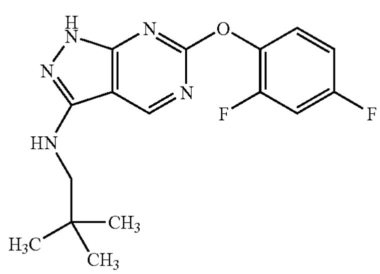 | [6-(2,4-Difluoro-phenoxy)-1H-pyrazolo[3,4-d]pyrimidin-3-yl]-(2,2-dimethyl-propyl)-amine | 334 |

TABLE 1-continued

| # | Structure | Name (Autonom ™) | MP (° C.) or M+ H |
|---|---|---|---|
| 60 | 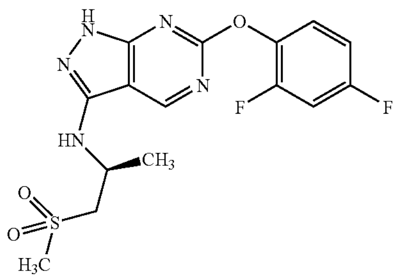 | [6-(2,4-Difluoro-phenoxy)-1H-pyrazolo[3,4-d]pyrimidin-3-yl]-((S)-2-methanesulfonyl-1-methyl-ethyl)-amine | 180.6-182.2 |
| 61 | 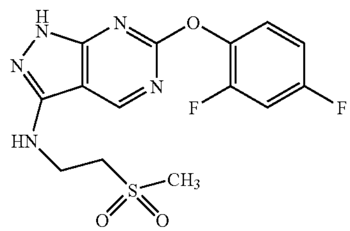 | [6-(2,4-Difluoro-phenoxy)-1H-pyrazolo[3,4-d]pyrimidin-3-yl]-(2-methanesulfonyl-ethyl)-amine | 201.3-202.5 |
| 62 | 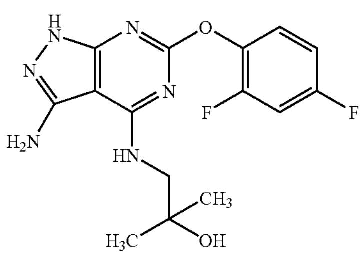 | 1-[3-Amino-6-(2,4-difluoro-phenoxy)-1H-pyrazolo[3,4-d]pyrimidin-4-ylamino]-2-methyl-propan-2-ol | 351 |
| 63 | 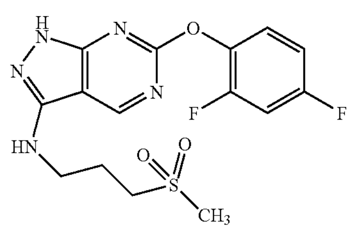 | [6-(2,4-Difluoro-phenoxy)-1H-pyrazolo[3,4-d]pyrimidin-3-yl]-(3-methanesulfonyl-propyl)-amine | 384 |
| 64 | 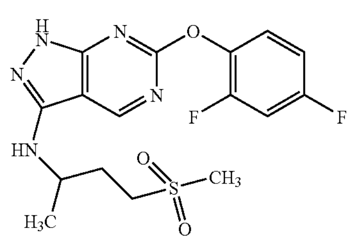 | [6-(2,4-Difluoro-phenoxy)-1H-pyrazolo[3,4-d]pyrimidin-3-yl]-(3-methanesulfonyl-1-methyl-propyl)-amine | 97.7-99.2 |
| 65 | 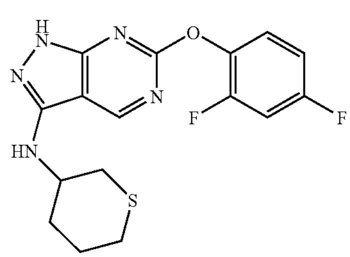 | [6-(2,4-Difluoro-phenoxy)-1H-pyrazolo[3,4-d]pyrimidin-3-yl]-(tetrahydro-thiopyran-3-yl)-amine | 364 |

TABLE 1-continued

| # | Structure | Name (Autonom ™) | MP (° C.) or M+ H |
|---|---|---|---|
| 66 | 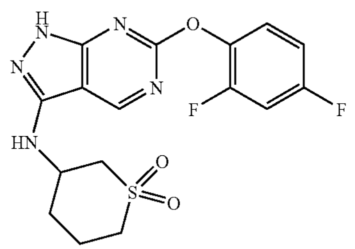 | [6-(2,4-Difluoro-phenoxy)-1H-pyrazolo[3,4-d]pyrimidin-3-yl]-(1,1-dioxo-hexahydro-1lambda*6*-thiopyran-3-yl)-amine | 396 |
| 67 | 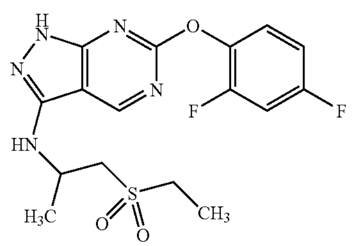 | [6-(2,4-Difluoro-phenoxy)-1H-pyrazolo[3,4-d]pyrimidin-3-yl]-(2-ethanesulfonyl-1-methyl-ethyl)-amine | 192.0-193.0 |
| 68 | 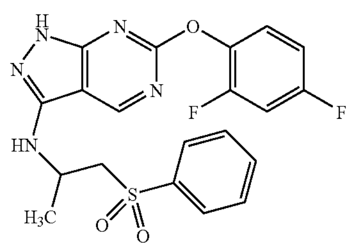 | (2-Benzenesulfonyl-1-methyl-ethyl)-[6-(2,4-difluoro-phenoxy)-1H-pyrazolo[3,4-d]pyrimidin-3-yl]-amine | 398 |
| 69 | 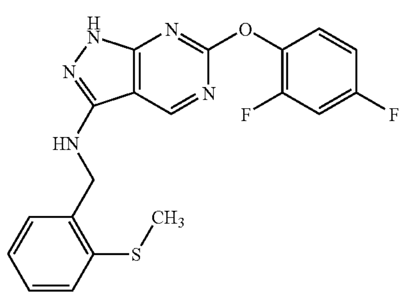 | [6-(2,4-Difluoro-phenoxy)-1H-pyrazolo[3,4-d]pyrimidin-3-yl]-(2-methylsulfanyl-benzyl)-amine | 400 |
| 70 | 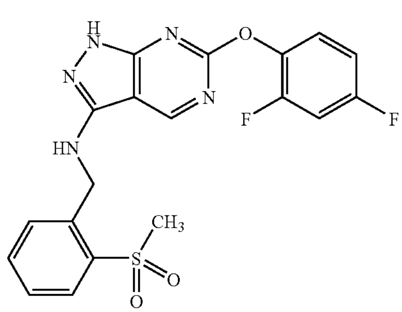 | [6-(2,4-Difluoro-phenoxy)-1H-pyrazolo[3,4-d]pyrimidin-3-yl]-(2-methylsulfonyl-benzyl)-amine | 432 |

TABLE 1-continued

| # | Structure | Name (Autonom ™) | MP (° C.) or M+ H |
|---|---|---|---|
| 71 | 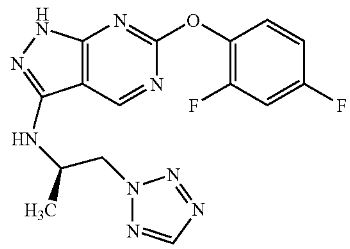 | [6-(2,4-Difluoro-phenoxy)-1H-pyrazolo[3,4-d]pyrimidin-3-yl]-((R)-1-methyl-2-tetrazol-2-yl-ethyl)-amine | 374 |
| 72 | 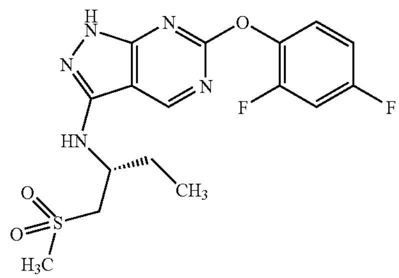 | [6-(2,4-Difluoro-phenoxy)-1H-pyrazolo[3,4-d]pyrimidin-3-yl]-((R)-1-methanesulfonylmethyl-propyl)-amine | 126.9-127.1 |
| 73 | 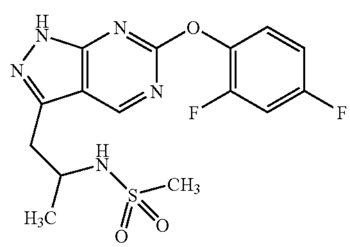 | N-{2-[6-(2,4-Difluoro-phenoxy)-1H-pyrazolo[3,4-d]pyrimidin-3-yl]-1-methyl-ethyl}-methanesulfonamide | 384 |
| 74 | 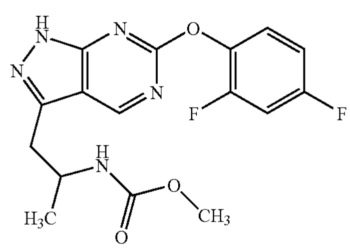 | {2-[6-(2,4-Difluoro-phenoxy)-1H-pyrazolo[3,4-d]pyrimidin-3-yl]-1-methyl-ethyl}-carbamic acid methyl ester | 364 |
| 75 | 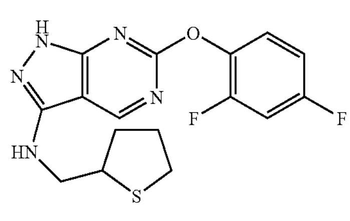 | [6-(2,4-Difluoro-phenoxy)-1H-pyrazolo[3,4-d]pyrimidin-3-yl]-(tetrahydro-thiophen-2-ylmethyl)-amine | 364 |
| 76 | 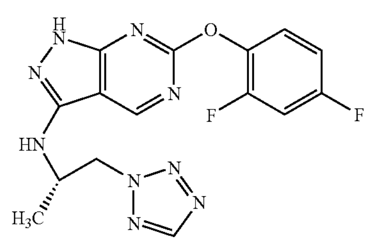 | [6-(2,4-Difluoro-phenoxy)-1H-pyrazolo[3,4-d]pyrimidin-3-yl]-((S)-1-methyl-2-tetrazol-2-yl-ethyl)-amine | 85.0-88.8 |

TABLE 1-continued

| # | Structure | Name (Autonom ™) | MP (° C.) or M+ H |
|---|---|---|---|
| 77 | 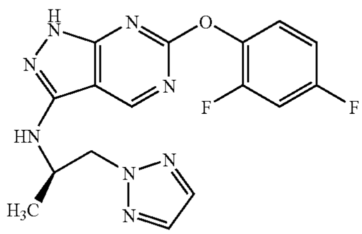 | [6-(2,4-Difluoro-phenoxy)-1H-pyrazolo[3,4-d]pyrimidin-3-yl]-((R)-1-methyl-2-[1,2,3]triazol-2-yl-ethyl)-amine | 96.6-101.8 |
| 78 | 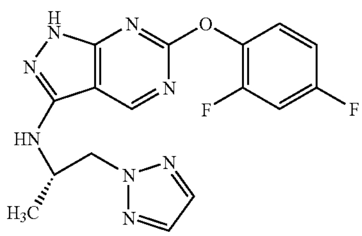 | [6-(2,4-Difluoro-phenoxy)-1H-pyrazolo[3,4-d]pyrimidin-3-yl]-((S)-1-methyl-2-[1,2,3]triazol-2-yl-ethyl)-amine | 373 |
| 79 | 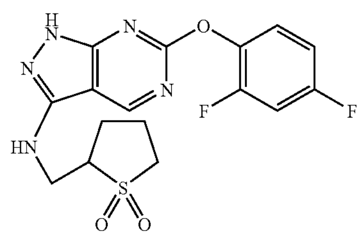 | [6-(2,4-Difluoro-phenoxy)-1H-pyrazolo[3,4-d]pyrimidin-3-yl]-(1,1-dioxo-tetrahydro-1lambda*6*-thiophen-2-ylmethyl)-amine | 396 |
| 80 | 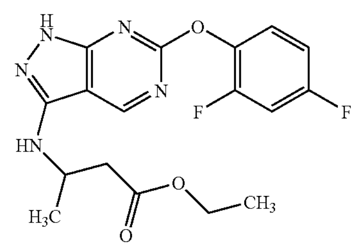 | 3-[6-(2,4-Difluoro-phenoxy)-1H-pyrazolo[3,4-d]pyrimidin-3-ylamino]-butyric acid ethyl ester | 378 |
| 81 | 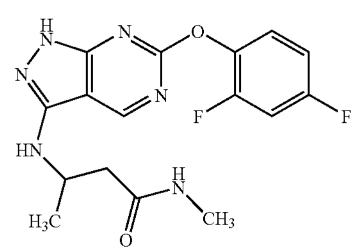 | 3-[6-(2,4-Difluoro-phenoxy)-1H-pyrazolo[3,4-d]pyrimidin-3-ylamino]-N-methyl-butyramide | 363 |
| 82 | 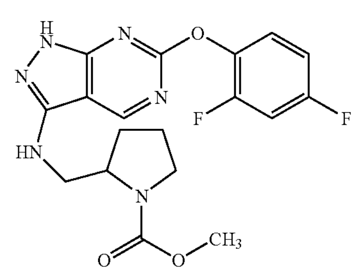 | 2-{[6-(2,4-Difluoro-phenoxy)-1H-pyrazolo[3,4-d]pyrimidin-3-ylamino]-methyl}-pyrrolidine-1-carboxylic acid methyl ester | 405 |

TABLE 1-continued

| # | Structure | Name (Autonom ™) | MP (° C.) or M+ H |
|---|---|---|---|
| 83 | 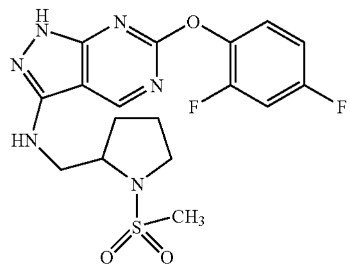 | [6-(2,4-Difluoro-phenoxy)-1H-pyrazolo[3,4-d]pyrimidin-3-yl]-(1-methanesulfonyl-pyrrolidin-2-ylmethyl)amine | 425 |
| 84 | 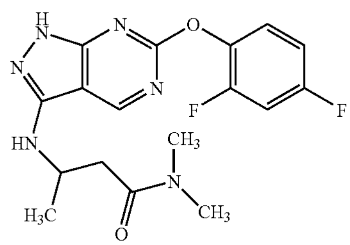 | 3-[6-(2,4-Difluoro-phenoxy)-1H-pyrazolo[3,4-d]pyrimidin-3-ylamino]-N,N-dimethyl-butyramide | 377 |
| 85 | 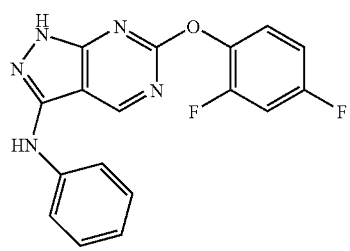 | [6-(2,4-Difluoro-phenoxy)-1H-pyrazolo[3,4-d]pyrimidin-3-yl]-phenyl-amine | 340 |
| 86 | 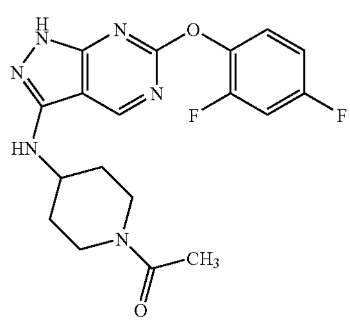 | 1-{4-[6-(2,4-Difluoro-phenoxy)-1H-pyrazolo[3,4-d]pyrimidin-3-ylamino]-piperidin-1-yl}-ethanone | 120.0-123.0 |
| 87 | 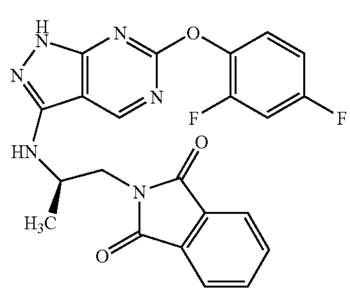 | 2-{(R)-2-[6-(2,4-Difluoro-phenoxy)-1H-pyrazolo[3,4-d]pyrimidin-3-ylamino]-propyl}-isoindole-1,3-dione | 451 |

TABLE 1-continued

| # | Structure | Name (Autonom ™) | MP (° C.) or M+ H |
|---|---|---|---|
| 88 | 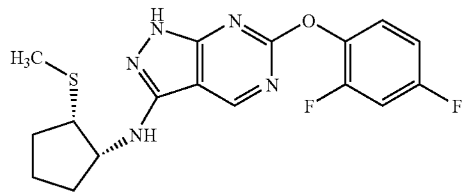 | [6-(2,4-Difluoro-phenoxy)-1H-pyrazolo[3,4-d]pyrimidin-3-yl]-((1S,2S)-2-methylsulfanyl-cyclopentyl)-amine | 378 |
| 89 | 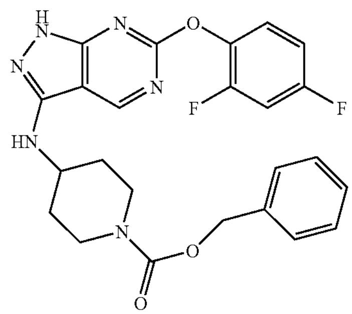 | 4-[6-(2,4-Difluoro-phenoxy)-1H-pyrazolo[3,4-d]pyrimidin-3-ylamino]-piperidine-1-carboxylic acid benzyl ester | 481 |
| 90 | 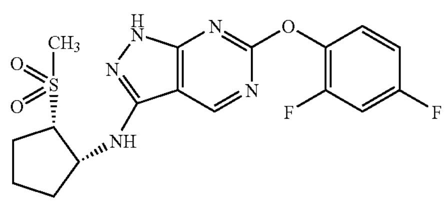 | [6-(2,4-Difluoro-phenoxy)-1H-pyrazolo[3,4-d]pyrimidin-3-yl]-((1S,2S)-2-methanesulfonyl-cyclopentyl)-amine | 410 |
| 91 | 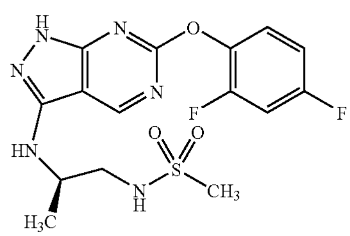 | N-{(R)-2-[6-(2,4-Difluoro-phenoxy)-1H-pyrazolo[3,4-d]pyrimidin-3-ylamino]-propyl}-methanesulfonamide | 399 |
| 92 | 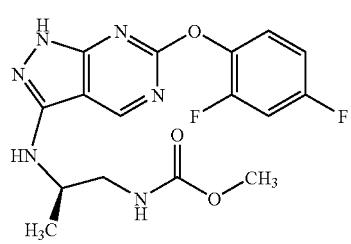 | {(R)-2-[6-(2,4-Difluoro-phenoxy)-1H-pyrazolo[3,4-d]pyrimidin-3-ylamino]-propyl}-carbamic acid methyl ester | 379 |
| 93 | 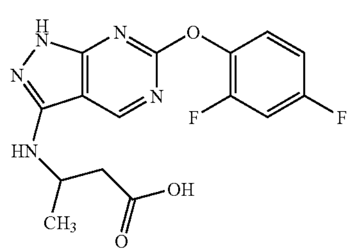 | 3-[6-(2,4-Difluoro-phenoxy)-1H-pyrazolo[3,4-d]pyrimidin-3-ylamino]-butyric acid | 350 |

TABLE 1-continued

| # | Structure | Name (Autonom ™) | MP (° C.) or M+ H |
|---|---|---|---|
| 94 | 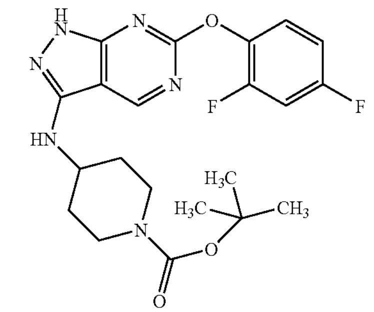 | 4-[6-(2,4-Difluoro-phenoxy)-1H-pyrazolo[3,4-d]pyrimidin-3-ylamino]-piperidine-1-carboxylic acid tert-butyl ester | 447 |
| 95 | 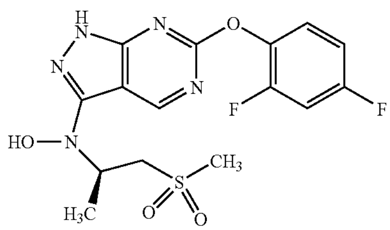 | Note-outside claim scope N-[6-(2,4-Difluoro-phenoxy)-1H-pyrazolo[3,4-d]pyrimidin-3-yl]-N-((R)-2-methanesulfonyl-1-methyl-ethyl)-hydroxylamine | 168.5-171.5 |
| 96 | 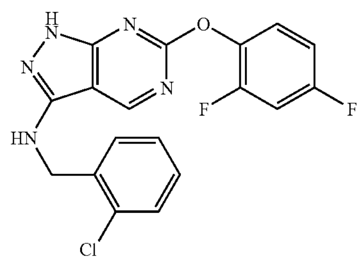 | (2-Chloro-benzyl)-[6-(2,4-difluoro-phenoxy)-1H-pyrazolo[3,4-d]pyrimidin-3-yl]-amine | 388 |
| 97 | 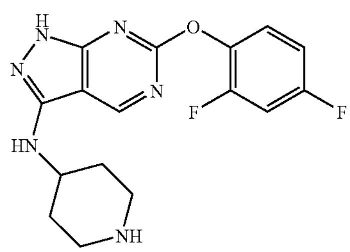 | [6-(2,4-Difluoro-phenoxy)-1H-pyrazolo[3,4-d]pyrimidin-3-yl]-piperidin-4-yl-amine | 288.5-290.6 (HCl salt) |
| 98 | 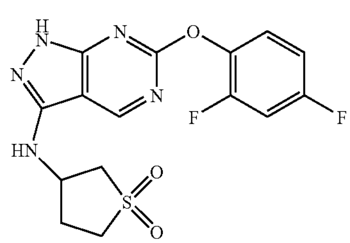 | [6-(2,4-Difluoro-phenoxy)-1H-pyrazolo[3,4-d]pyrimidin-3-yl]-(1,1-dioxo-tetrahydro-1lambda*6*-thiophen-3-yl)-amine | 382 |
| 99 | 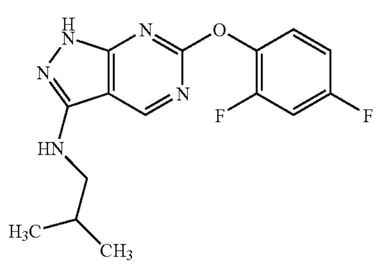 | [6-(2,4-Difluoro-phenoxy)-1H-pyrazolo[3,4-d]pyrimidin-3-yl]-isobutyl-amine | 320 |

TABLE 1-continued

| # | Structure | Name (Autonom ™) | MP (° C.) or M+ H |
|---|---|---|---|
| 100 | 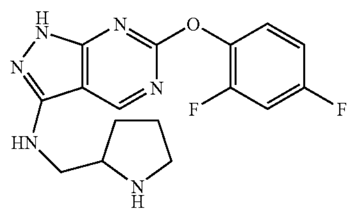 | [6-(2,4-Difluoro-phenoxy)-1H-pyrazolo[3,4-d]pyrimidin-3-yl]-pyrrolidin-2-ylmethyl-amine | 347 |
| 101 | 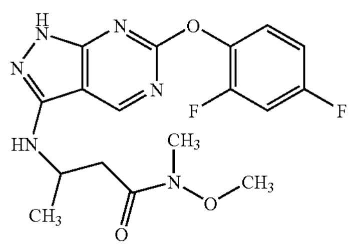 | 3-[6-(2,4-Difluoro-phenoxy)-1H-pyrazolo[3,4-d]pyrimidin-3-ylamino]-N-methoxy-N-methyl-butyramide | 393 |
| 102 | 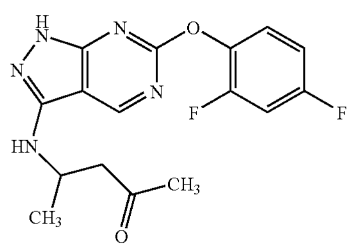 | 4-[6-(2,4-Difluoro-phenoxy)-1H-pyrazolo[3,4-d]pyrimidin-3-ylamino]-pentan-2-one | 348 |
| 103 | 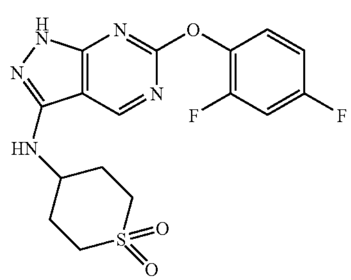 | [6-(2,4-Difluoro-phenoxy)-1H-pyrazolo[3,4-d]pyrimidin-3-yl]-(1,1-dioxo-hexahydro-1lambda*6*-thiopyran-4-yl)-amine | 280.9-282.3 |
| 104 | 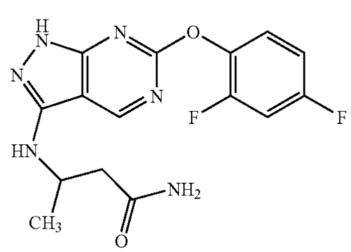 | 3-[6-(2,4-Difluoro-phenoxy)-1H-pyrazolo[3,4-d]pyrimidin-3-ylamino]-butyramide | 349 |

Table 1

Representative compounds in accordance with one aspect of the invention are shown below in Table 2.

TABLE 2

| # | Structure | Name (Autonom ™) | MP or M + H |
|---|---|---|---|
| 1 | 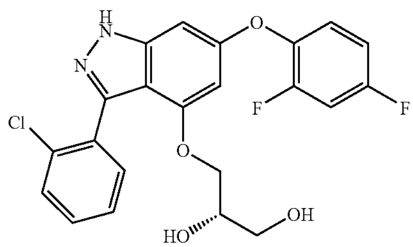 | 3-[3-(2-Chloro-phenyl)-6-(2,4-difluoro-phenoxy)-1H-indazol-4-yloxy]-propane-1,2-diol | 93.3-94.6° C. |
| 2 | 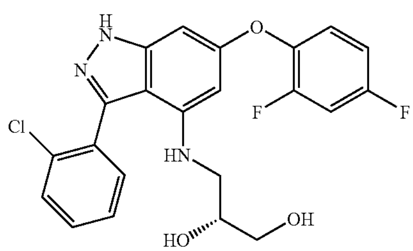 | 3-[3-(2-Chloro-phenyl)-6-(2,4-difluoro-phenoxy)-1H-indazol-4-ylamino]-propane-1,2-diol | 116.3-119° C. |
| 3 | 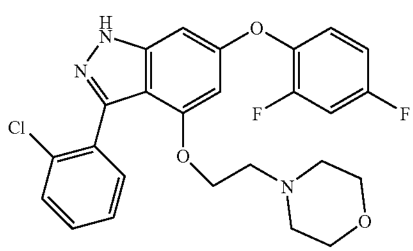 | 3-(2-Chloro-phenyl)-6-(2,4-difluoro-phenoxy)-4-(2-morpholin-4-yl-ethoxy)-1H-indazole | 75.6-79.9° C. |

Table 2

Synthesis

Compounds of the present invention can be made by a variety of methods depicted in the illustrative synthetic reaction schemes shown and described below.

The starting materials and reagents used in preparing these compounds generally are available from commercial suppliers, such as Aldrich Chemical Co., or are prepared by methods known to those skilled in the art following procedures set forth in references such as *Fieser and Fieser's Reagents for Organic Synthesis;* Wiley & Sons: New York, 1991, Volumes 1-15; *Rodd's Chemistry of Carbon Compounds,* Elsevier Science Publishers, 1989, Volumes 1-5 and Supplementals; and Organic Reactions, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

One of the specific methods for preparing pyrazolopyrimidine compounds of the invention is shown in Scheme A below, wherein L is a leaving group and W, X, Y, $R^4$, $R^5$ and $R^a$ are as defined herein.

Another method for preparing compounds of the invention is shown in Scheme B below, wherein PG is a protecting group and p, W, X, Y, $R^2$, $R^4$ and $R^5$ are as defined herein.

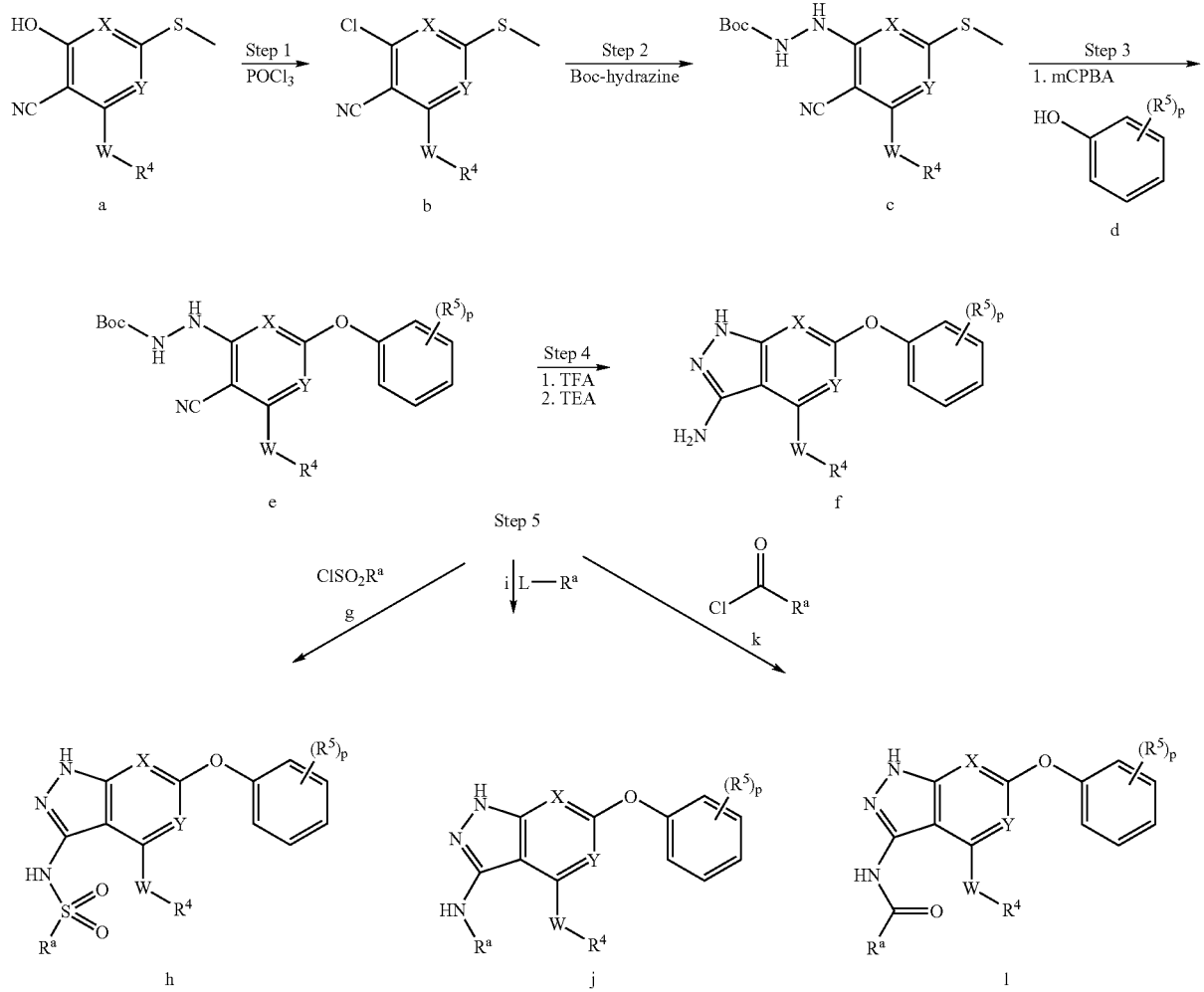

In step 1 of Scheme A, cyanophenolic compound a is chlorinated by reaction with phosphorous oxychloride or other chlorine source to form compound b. Compound b is treated with Boc-hydrazine in step 2 to afford cyano hydrazinyl compound c. In step 3, the sulfanyl group on compound c is oxidized to form a sulfonate (not shown), which is directly treated with phenol d in the presence of base to yield aromatic ether compound e. A cyclization reaction occurs in step 4 wherein compound e is treated with trifluoroacetic acid followed by an amine base such as triethylamine, to afford amino compound f. In step 5, compound f may be treated with sulfonyl chloride compound g to yield compound h; or compound f may be treated with carbonyl compound i in the presence of a suitable reducing agent to form compound j; or compound f may be reacted with carboxylic acid halide k to form compound l. Compounds h,j and l as well as compound f, are compounds of formula I in accordance with the invention

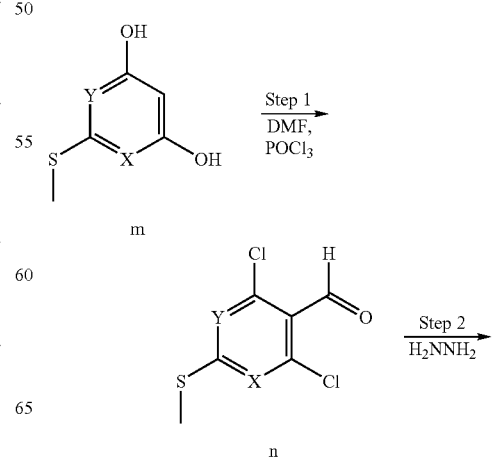

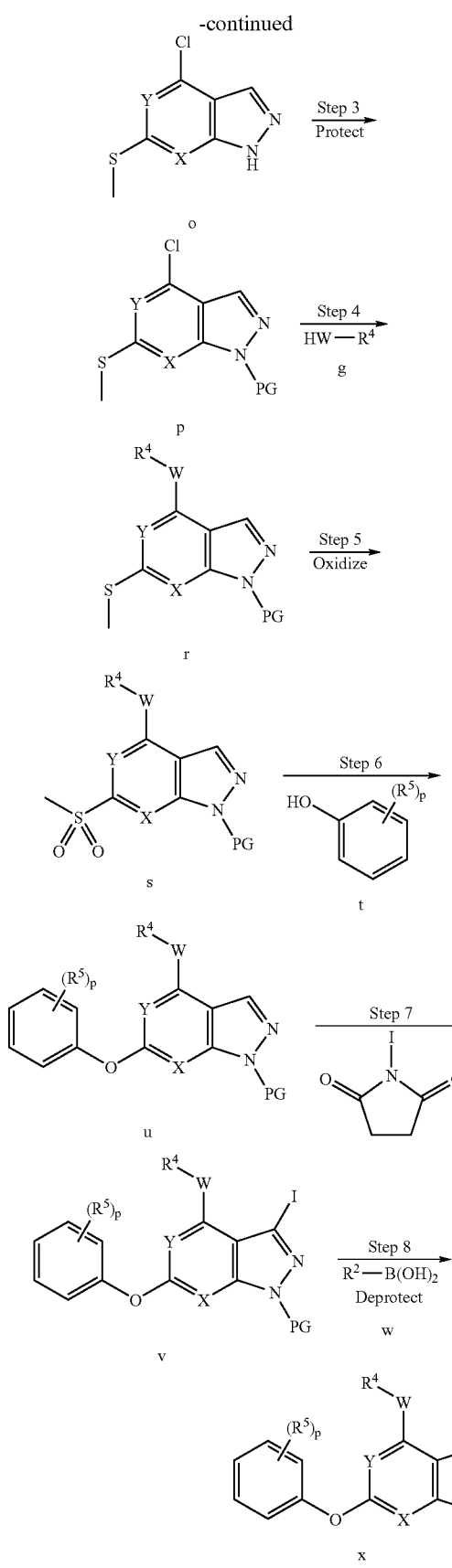

In step 1 of Scheme B, diol compound m undergoes an alkylation under chlorinating conditions to form dichloro carbaldehyde compound n. A cyclization reaction is carried out in step 2 wherein compound n is treated with hydrazine to form aza indazole compound o. The secondary amine group of compound o is protected in step 3 using trimethylsilylethoxymethylene chloride (SEM chloride) or like protecting agent to form protected compound p. Compound p may then be reacted with nucleophilic reagent q in step 4 to form compound r. In step 5, the sulfanyl group of compound r is oxidized to a sulfonyl group using a peracid or like mild oxidizing agent to provide compound s. In step 6, sulfonyl compound s is treated with base and reacted with phenol t to form ether compound u. Compound u is iodated in step 7 with N-iodosuccinimide or like iodine source to form iodo compound v, which is then reacted with boronic acid w in step 8, followed by deprotection, to yield compound x. Compound x is a compound of of formula I in accordance with the invention.

In certain embodiments of the procedure of Scheme B, the sulfonyl compound of step 5 need not be isolated, and steps 5 and 6 may be carried out in a single step. In embodiments where W is a bond and $R^4$ is hydrogen, compound m may have a single hydroxy group such that compound n has a single chloro group, and step 4 may be omitted.

Another method for preparing compounds of the invention is shown in Scheme C below, wherein p, W, X, Y, $R^a$, $R^4$ and $R^5$ are as defined herein.

SCHEME C

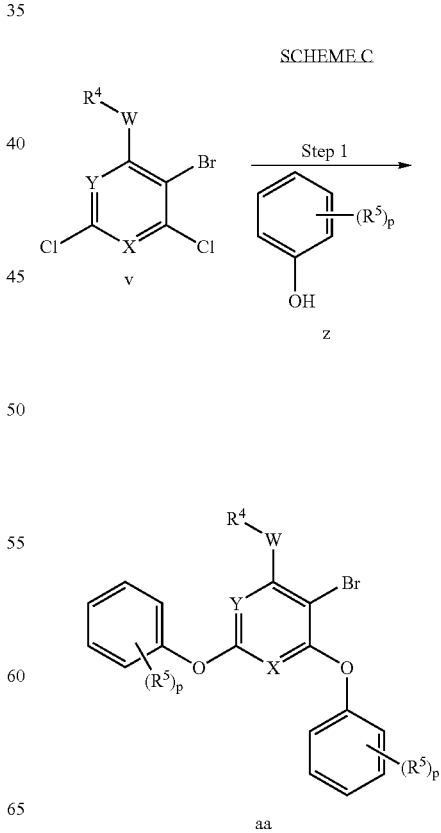

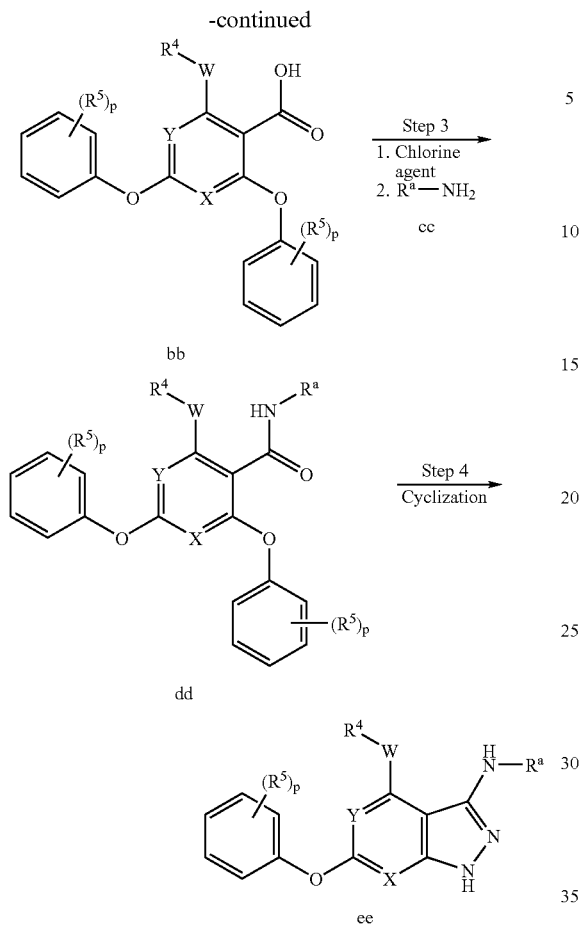

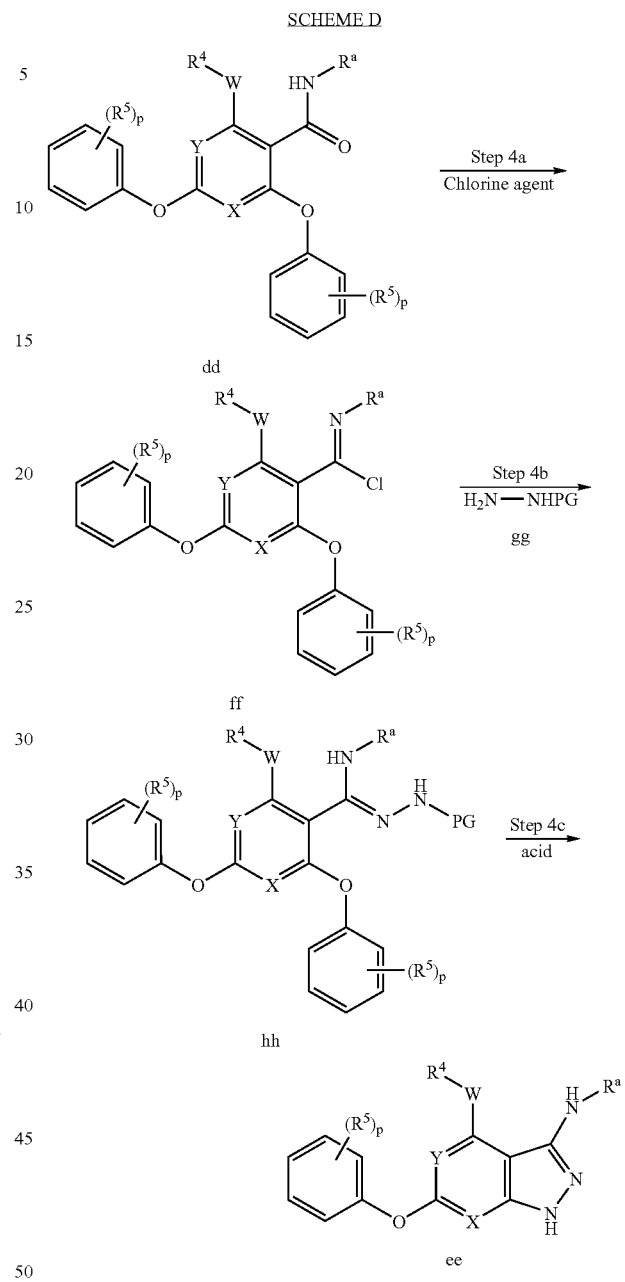

SCHEME D

In step 1 of Scheme C, dichloroaryl compound y is reacted with phenol compound z in the presence of base, such as NaOH or $K_2CO_3$ to afford diphenoxy bromoaryl compound aa. Phenol compound z may be replaced by other hydroxyaryl or hydroxyheteroaryl compounds in certain embodiments.

Diphenoxy bromoaryl compound aa is then treated in step 2 with Grignard reagent such as isopropylmagnesium chloride, followed by carbon dioxide, to yield diphenoxy carboxyaryl compound bb.

In step 3 compound bb is reacted with chlorinating agent such as oxalyl chloride or thionyl chloride to generate the corresponding acyl chloride (not shown), which is then reacted with amine cc to provide diphenoxy arylamide compound dd.

A cyclization is then carried out in step 4. This cyclization may be achieved by treatment of compound dd with a chlorine agent or an anhydride, followed by reaction with hydrazine to effect ring closure and form a pyrazolo group and give compound ee, which is a compound of formula I in accordance with the invention. In certain embodiments the hydrazine may be protected with BOC or other protecting group, and a deprotection event may be included within step 4.

Scheme D shows one preferred cyclization process for step 4 of Scheme C, wherein PG is a protecting group and p, W, X, Y, $R^a$, $R^4$ and R5 are as defined herein.

In step 4a of Scheme D, diphenoxy aramide compound dd is reacted with with a chlorine agent such as thionyl chloride or oxalyl chloride, to afford chioro ethyl idine compound ff. Treatment of compound ff in step 4b with a protected hydrazine gg, such as BOC-carbazate, provides hydrazine carboxamide compound hh. Compound hh is then treated with acid to remove protecting group PG and effect ring closure to provide the compound ee. In many embodiments ethylidine compound ff need not be isolated, but may be generated in situ and treated directly with protected hydrazine gg.

In a preferred embodiment of the invention wherein an alkylsulfonylalkyl group is desired for $R^a$, the procedure of Scheme D may be used, wherein PG, p, W, X, Y, $R^a$, $R^4$ and $R^5$ are as defined herein.

SCHEME E

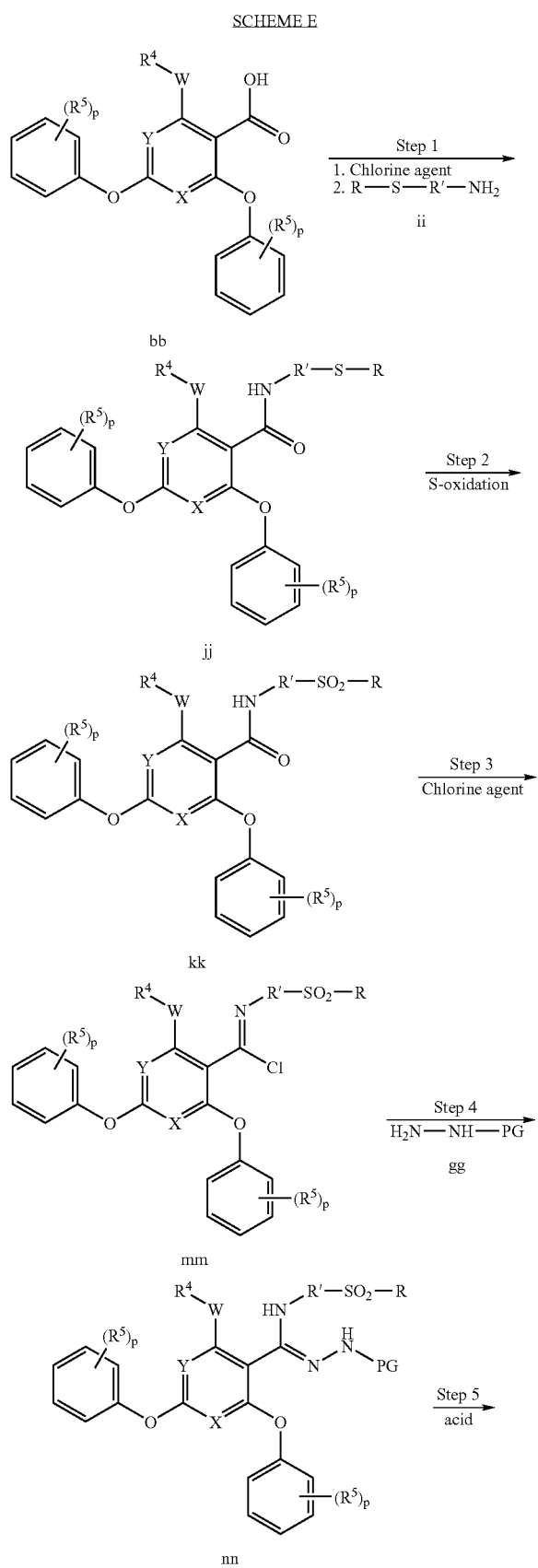

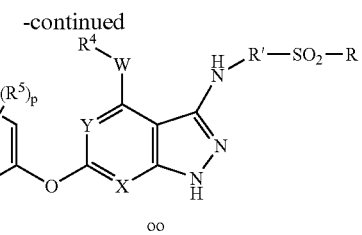

In step 1 of Scheme E, diphenoxy carboxyaryl compound bb is treated with a chlorine agent such as oxalyl chloride, thionyl chloride or the like, followed by alkylsulfanylamine compound ii, to afford alkylsulfanylalkyl amide compound jj.

Oxidation of the sulfanyl sulfur atom occurs in step 2, which may be achieved by treatment of compound gg with hydrogen peroxide or other peroxide agent such as MCPBA, OXONE™ or the like, to give alkylsulfonylalkyl amide compound kk.

In step 3, amide compound kk is treated with chlorine agent such as oxalyl chloride, thionyl chloride or the like, to generate chloro ethylidine compound mm.

Treatment of compound mm in step 4 with protected hydrazine gg, such as BOC-carbazate, provides hydrazine carboxamide compound nn.

Compound nn is then treated with acid in step 5 to remove protecting group PG and effect ring closure to provide the compound ee. In many embodiments ethylidine compound mm need not be isolated, but may be generated in situ and treated directly with protected hydrazine gg to afford compound nn.

More specific details for producing compounds of formula (I) are described in the Examples section below.

Pharmaceutical Compositions and Administration

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in the Examples below.

Compounds of the invention are useful for, but not limited to, the treatment of any disorder or disease state in a human, or other mammal, which is exacerbated or caused by excessive or unregulated TNF or p38 kinase production by such mammal. Accordingly, the present invention provides a method of treating a p38-mediated disease which comprises administering an effective amount of a compound of the invention, or a pharmaceutically acceptable salt, solvate or prodrug thereof, to a subject or patient in need thereof.

Compounds of the invention are useful for, but not limited to, the treatment of inflammation in a subject, and for use as antipyretics for the treatment of fever. Compounds of the invention would be useful to treat arthritis, including but not limited to, rheumatoid arthritis, spondyloarthropathies, gouty arthritis, osteoarthritis, systemic lupus erythematosus and juvenile arthritis, osteoarthritis, gouty arthritis and other arthritic conditions. Such compounds would be useful for the treatment of pulmonary disorders or lung inflammation, including adult respiratory distress syndrome, pulmonary sarcoidosis, asthma, silicosis, and chronic pulmonary inflammatory disease. The compounds are also useful for the treatment of viral and bacterial infections, including sepsis, septic shock, gram negative sepsis, malaria, meningitis, cachexia secondary to infection or malignancy, cachexia secondary to acquired immune deficiency syndrome (AIDS), AIDS, ARC (AIDS related complex), pneumonia, and herpes virus. The compounds are also useful for the treatment of bone resorption diseases, such as osteoporosis, endotoxic shock, toxic shock syndrome, reperfusion injury, autoimmune disease including graft vs. host reaction and allograft rejections, cardiovascular diseases including atherosclerosis, thrombosis, congestive heart failure, and cardiac reperfusion injury, renal reperfusion injury, liver disease and nephritis, and myalgias due to infection.

The compounds are also useful for the treatment of Alzheimer's disease, influenza, multiple sclerosis, cancer, diabetes, systemic lupus erthrematosis (SLE), skin-related conditions such as psoriasis, eczema, burns, dermatitis, keloid formation, and scar tissue formation. In addition, compounds of the invention are useful in treating gastrointestinal conditions such as inflammatory bowel disease, Crohn's disease, gastritis, irritable bowel syndrome and ulcerative colitis. The compounds are also useful in the treatment of ophthalmic diseases, such as retinitis, retinopathies, uveitis, ocular photophobia, and of acute injury to the eye tissue. The compounds can also be used in treating angiogenesis, including neoplasia; metastasis; ophthalmological conditions such as corneal graft rejection, ocular neovascularization, retinal neovascularization including neovascularization following injury or infection, diabetic retinopathy, retrolental fibroplasia and neovascular glaucoma; ulcerative diseases such as gastric ulcer; pathological, but non-malignant, conditions such as hemangiomas, including infantile hemangiomas, angiofibroma of the nasopharynx and avascular necrosis of bone; diabetic nephropathy and cardiomyopathy; and disorders of the female reproductive system such as endometriosis. The compounds can further be used for preventing the production of cyclooxygenase-2 and have analgesic properties. Therefore, Compounds of Formula I are useful for treatment of pain.

Other uses for Compounds of Formula I include treatment of HCV, severe asthma, psoriasis, chronic obstructive pulmonary disease (COPD), cancer, multiple myeloma, and other diseases that can be treated with an anti-TNF compound.

Besides being useful for human treatment, these compounds are also useful for veterinary treatment of companion animals, exotic animals and farm animals, including mammals, rodents, and the like. More preferred animals include horses, dogs, and cats.

The present compounds can also be used in co-therapies, partially or completely, in place of other conventional antiinflammatories, such as together with steroids, cyclooxygenase-2 inhibitors, NSAIDs, DMARDS, immunosuppressive agents, 5-lipoxygenase inhibitors, $LTB_4$ antagonists and $LTA_4$ hydrolase inhibitors.

As used herein, the term "TNF mediated disorder" refers to any and all disorders and disease states in which TNF plays a role, by control of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disorder mediated by TNF.

As used herein, the term "p38 mediated disorder" refers to any and all disorders and disease states in which p38 plays a role, by control of p38 itself, or by p38 causing another factor to be released, such as but not limited to IL-1, IL-6 or IL-8. A disease state in which, for instance, IL-1 is a major component, and whose production or action, is exacerbated or secreted in response to p38, would therefore be considered a disorder mediated by p38.

As TNF-β has close structural homology with TNF-α (also known as cachectin), and since each induces similar biologic responses and binds to the same cellular receptor, the synthesis of both TNF-α and TNF-β are inhibited by the compounds of the present invention and thus are herein referred to collectively as "TNF" unless specifically delineated otherwise.

EXAMPLES

The following preparations and examples are given to enable those skilled in the art to more clearly understand and to practice the present invention. They should not be considered as limiting the scope of the invention, but merely as being illustrative and representative thereof.

Unless otherwise stated, all temperatures including melting points (i.e., MP) are in degrees celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The following abbreviations may be used in the Examples.

| ABBREVIATIONS | |
|---|---|
| BOC | tert-butoxycarbonyl |
| DCM | dichloromethane |
| DMF | N,N-dimethylformamide |
| DMAP | 4-dimethylaminopyridine |
| gc | gas chromatography |
| HMPA | hexamethylphosphoramide |
| hplc | high performance liquid chromatography |
| mCPBA | m-chloroperbenzoic acid |
| MeCN | acetonitrile |
| TEA | triethylamine |
| THF | tetrahydrofuran |
| LDA | lithium diisopropylamine |
| TLC | thin layer chromatography |
| uL | microliter |

Preparation 1

[6-(2,4-Difluoro-phenoxy)-1H-pyrazolo[3,4-d]pyrimidin-3-yl]-isopropyl-amine

The synthetic procedure of Example 1 is shown in Scheme F.

SCHEME F

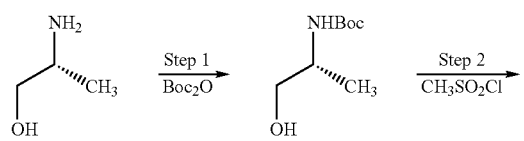

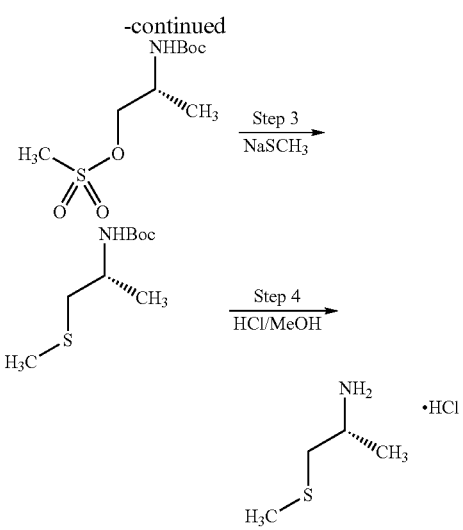

Step 1 (R)-2-Boc-amino-propan-1-ol (R)-2-Amino-propan-1-ol (30.o g, 0.3994 mol) was dissolved in 800 mL methanol and cooled in an ice bath for 30 minutes. Boc anhydride (87.17 g, 0.3994 mol) in 250 methanol was added in portions to the stirring reaction mixture. The ice bath was removed and stirring was continued for three hours. The reaction mixture was evaporated to dryness under reduced pressure to give (R)-2-boc-amino-propanolol, 1-ol, which was used directly in the next step in the same flask.

Step 2 (R)-2-Boc-amino-1-methanesulfonyl-propan-1-ol

Methylene chloride (400 mL) and triethylamine (83.9 mL, 0.60 mol) were added to the flask containing (R)-2-boc-amino-propan-1-ol (from step 1). The reaction mixture was cooled in an ice bath for 30 minutes, and then methanesulfonyl chloride (37.0 mL, 0.478 mol) was added dropwise over a five minute period. The reaction mixture was stirred for one hour, then the ice bath was removed and the reaction mixture was stirred for 18 hours at room temperature. The reaction mixture was washed with 10% aqueous NaOH solution, and the organic layer was dried over MgSO₄, filtered, and concentrated under reduced pressure to give 91.93 g of (R)-2-boc-amino-1-methanesulfonyl-propan-1-ol.

Step 3 (R)-2-Boc-amino-1-methanesulfanyl-propane

A mixture of (R)-2-boc-amino-1-methanesulfonyl-propan-1-ol (91.93 g, 363 mmol), THF (350 mL) and sodium thiomethoxide (30.0 g, 406 mmol) was stirred at room temperature for 18 hours. The reaction mixture was then concentrated under reduced pressure and the residue was partitioned between diethyl ether and water. The organic layer was washed withe brine, dried over MgSO₄, filtered, and concentrated under reduced pressure to give 70.8 g of (R)-2-boc-amino-1-methanesulfanyl-propane.

Step 4 (R)-1-Methyl-2-methylsulfanyl-ethylamine

Methanol (400 mL) was cooled in an ice bath for 30 minutes, and acetyl chloride (100 mL) was added dropwise over 45 minutes. The resulting solution was added to (R)-2-Boc-amino-1-methanesulfanyl-propane (70.47 g, 343 mmol), with stirring at ice bath temperature. The reaction mixture was stirred for 15 minutes after addition was completed, and then the ice bath was removed and stirring was continued for two hours. The reaction mixture was concentrated under reduced pressure to a solid, and THF (700 mL) was added. The mixture was heated to reflux until all solids had dissolved, then cooled to room temperature, and then cooled to 0 °C. for 30 minutes. The resulting precipitate was collected by filtration, washed with cold THF, and dried to give 23.57 g of (R)-1-methyl-2-methylsulfanyl-ethylamine, MS(M+H)=106.

Example 1

[6-(2,4-Difluoro-phenoxy-1H-pyrazolo[3,4-d]pyrimidin-3-yl]-isopropyl-amine

The synthetic procedure of Example 1 is shown in Scheme G.

SCHEME G

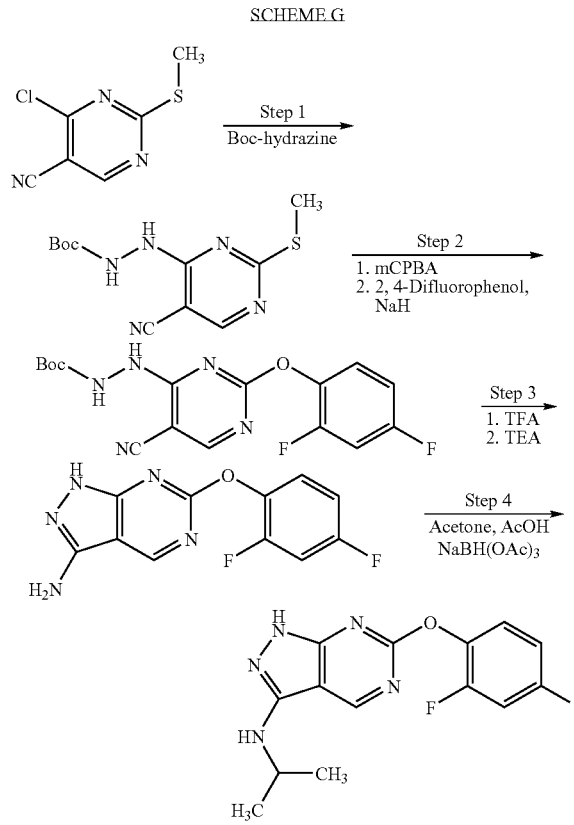

Step 1 N'-(5-Cyano-2-methylsulfanyl-pyrimidin-4-yl)-hydrazinecarboxvlic acid tert-butyl ester 4-Chloro-2-methylsulfanyl-pyrimidine-5-carbonitrile (prepared as described in US2003158218, 0.509 g, 2.74 mmol), tert-butyl carbazate (tert-butoxycarbonyl hydrazine, 0.403 g, 3.05 mmol) and triethylamine (0.57 mL, 4.1 mmol) were added to 25 mL THF. The reaction mixture was stirred 22 hours, and then 25 mL diethyl ether was added and the reaction mixture was filtered through Celite. The filtrate was concentrated under reduced pressure and the resulting oil was chromatographed through silica (0%-33% EtOAc in hexanes) to give 0.64 g of N'-(5-cyano-2-methylsulfanyl-pyrimidin-4-yl)-hydrazinecarboxylic acid tert-butyl ester.

Step 2 N'-[5-Cyano-2-(2,4-difluoro-phenoxy)-pyrimidin-4-yl]-hydrazinecarboxylic acid tert-butyl ester N'-(5-Cyano-2-methylsulfanyl-pyrimidin-4-yl)-hydrazinecarboxylic acid tert-butyl ester (0.602 g, 2.14 mmol) was added to 20 mL of stirring dichloromethane, and meta-chloroperbenzoic acid (0.574 g, 2.56 mmol of 77% pure solid) was added. The reaction mixture was stirred for one hour, then concentrated under reduced pressure to leave a white solid.

In a separate flask, 2,4-dinitrophenol (0.82 mL, 8.6 mmol) was added to 10 mL dry DMF under nitrogen and chilled for 15 minutes in an ice bath. Sodium hydride (0.341 g, 8.52 mmol, 60% in mineral oil) was added slowly, and the reaction mixture was stirred for 10 minutes at 0° C. This mixture was transferred via pipette to the white solid prepared in the previous paragraph. The resulting reaction mixture was stirred at room temperature under nitrogen for 18 hours, then partitioned between saturated aqueous $NH_4Cl$ and diethyl ether. The organic layer was separated, washed with water, dried over $MgSO_4$, filtered and concentrated under reduced pressure. The residue was chromatographed through silica (0%-33% EtOAc in hexanes) to yield 0.639 g of N'-[5-cyano-2-(2,4-difluoro-phenoxy)-pyrimidin-4-yl]-hydrazinecarboxylic acid tert-butyl ester as a solid foam.

Step 3 6-(2,4-Difluoro-phenoxy)-1H-pyrazolo[3,4-d]pyrimidin-3-ylamine

N'-[5-Cyano-2-(2,4-difluoro-phenoxy)-pyrimidin-4-yl]-hydrazinecarboxylic acid tert-butyl ester (3.35 g, 9.22 mmol) was dissolved in 60 mL of dichloromethane, and 30 mL of trifluoroacetic acid was added. The reaction mixture was stirred for two and a half hours at room temperature, then concentrated under reduced pressure. 1-Butanol (90 mL) and triethylamine (6.4 mL, 46 mmol) was added to the residue, and the reaction mixture was heated to reflux with stirring for 17 hours. The reaction mixture was cooled and concentrated under reduced pressure. The residue was taken up in 300 mL and insoluble yellow solid was isolated by filtration, washing with 100 mL of dichloromethane and in vacuo, to give 1.45 g of 6-(2,4-difluoro-phenoxy)-1H-pyrazolo[3,4-d]pyrimidin-3-ylamine, MS(M+H)=264.

Step 4 [6-(2,4-Difluoro-phenoxy)-1H-pyrazolo[3,4-d]pyrimidin-3-yl]-isopropyl-amine To a room temperature slurry of 6-(2,4-Difluoro-phenoxy)-1H-pyrazolo[3,4-d]pyrimidin-3-ylamine (170 mg, 0.646 mmol), acetone (0.95 mL, 12.9 mmol) acetic acid (0.037 mL) and THF (6.5 mL) was added $NaBH(OAc)_3$ (547 mg, 2.58 mmol). The reaction mixture was heated to reflux for 18 hours, then cooled to room temperature and diluted with ether. This mixture was washed with water and brine, then dried over $MgSO_4$, filtered, and concentrated under reduced pressure. The residue was chromatographed through silica (10%-50% EtOAc in hexanes) to give 105 mg of [6-(2,4-difluoro-phenoxy)-1H-pyrazolo[3,4-d]pyrimidin-3-yl]-isopropyl-amine, MP=211.3-214.4° C., MS(M+H)=306.

Additional compounds were prepared by the above procedure, and are shown in Table 1.

Example 2

Cyclopentanecarboxylic Acid [6-(2,4-difluoro-phenoxy)-1H-pyrazolo[3,4-d]pyrimidin-3-yl]-amide

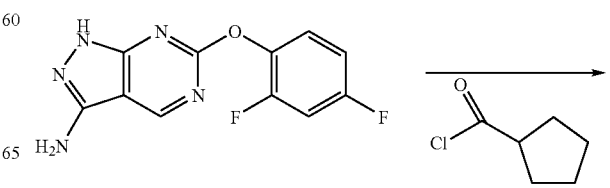

-continued

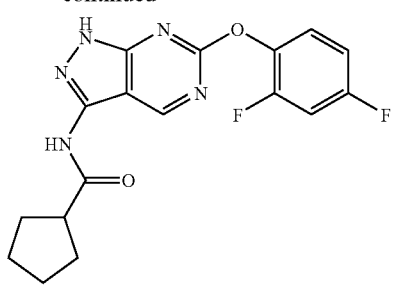

To a solution of 6-(2,4-difluoro-phenoxy)-1H-pyrazolo[3,4-d]pyrimidin-3-ylamine (45 mg, 0.17 mmol) in 1.7 mL of dioxane was added 14 uL pyridine and cyclopropane carbonyl chloride (21 uL, 0.17 mmol). The reaction mixture was heated to reflux for three hours, then cooled and chromatographed through silica (20%-50% EtOAc in hexanes) to afford 32 mg of cyclopentanecarboxylic acid [6-(2,4-difluoro-phenoxy)-1H-pyrazolo[3,4-d]pyrimidin-3-yl]-amide, MP=206.3-207.51° C., MS (M+H)=360.

Additional compounds were prepared by the above procedure, and are shown in Table 1.

Example 3

Ethanesulfonic acid [6-(2,4-difluoro-phenoxy)-1H-pyrazolo[3,4-d]pyrimidin-3-yl]-amide

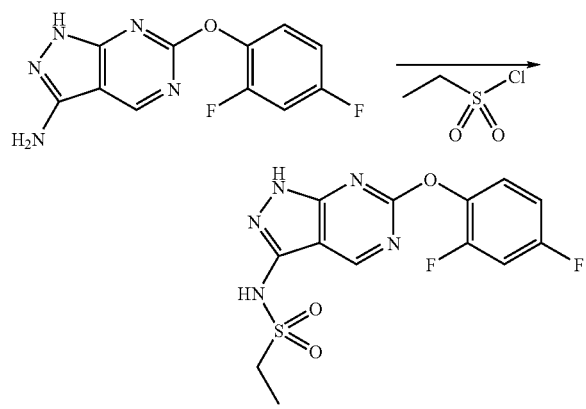

To 6-(2,4-difluoro-phenoxy)-1H-pyrazolo[3,4-d]pyrimidin-3-ylamine (60 mg, 0.228 mmol) in 2 mL dioxane was added ethanesulfonyl chloride (22.0 uL, 0.228 mmol) and pyridine (18.5 uL, 0.228 mmol). The reaction mixture was heated to reflux with stirring for two hours, then cooled and chromatographed through silica (0%-40% EtOAc in hexanes) to give 31 mg of ethanesulfonic acid [6-(2,4-difluoro-phenoxy)-1H-pyrazolo[3,4-d]pyrimidin-3-yl]-amide, MP=226.0-226.9° C., MS(M+H)=356.

Additional compounds were prepared by the above procedure, and are shown in Table 1.

Example 4

[6-(2,4-Difluoro-phenoxy)-1H-pyrazolo[3,4-d]pyrimidin-3-yl]-carbamic acid benzyl ester

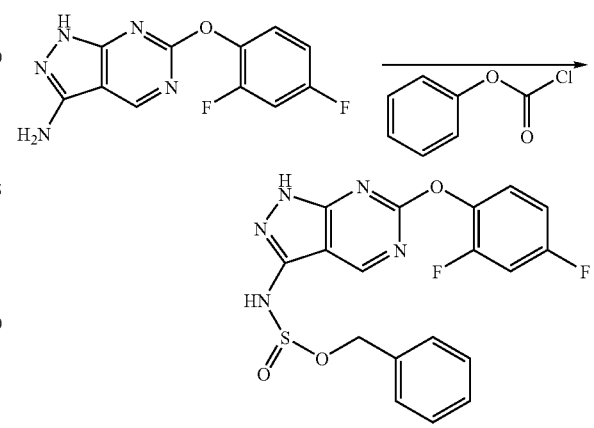

To 6-(2,4-difluoro-phenoxy)-1H-pyrazolo[3,4-d]pyrimidin-3-ylamine (40 mg, 0.152 mmol) in 6 mL THF was added carbonic acid chloride monobenzyl ester (24.0 uL, 0.167 mmol) and triethylamine (25.4 uL, 0.182 mmol). The reaction mixture was stirred at room temperature for 18 hours, then partitioned between water and EtOAc. The organic phase was separated, dried over MgSO4, filtered and concentrated under reduced pressure. The residue was chromatographed through silica (0%-50% EtOAc in hexanes) to give 59 mg of [6-(2,4-Difluoro-phenoxy)-1H-pyrazolo[3,4-d]pyrimidin-3-yl]-carbamic acid benzyl ester, MP 270.1-272.0° C.

Additional compounds were prepared by the above procedure, and are shown in Table 1.

Example 5

[6-(2,4-Difluoro-phenoxy)-1H-pyrazolo[3,4-d]pyrimidin-3-yl]-((R)-2-methanesulfonyl-1-methylethyl)-amine The synthetic procedure of Example 1 is shown in Scheme H.

SCHEME H

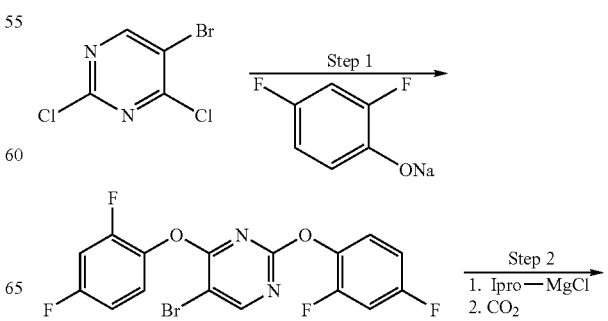

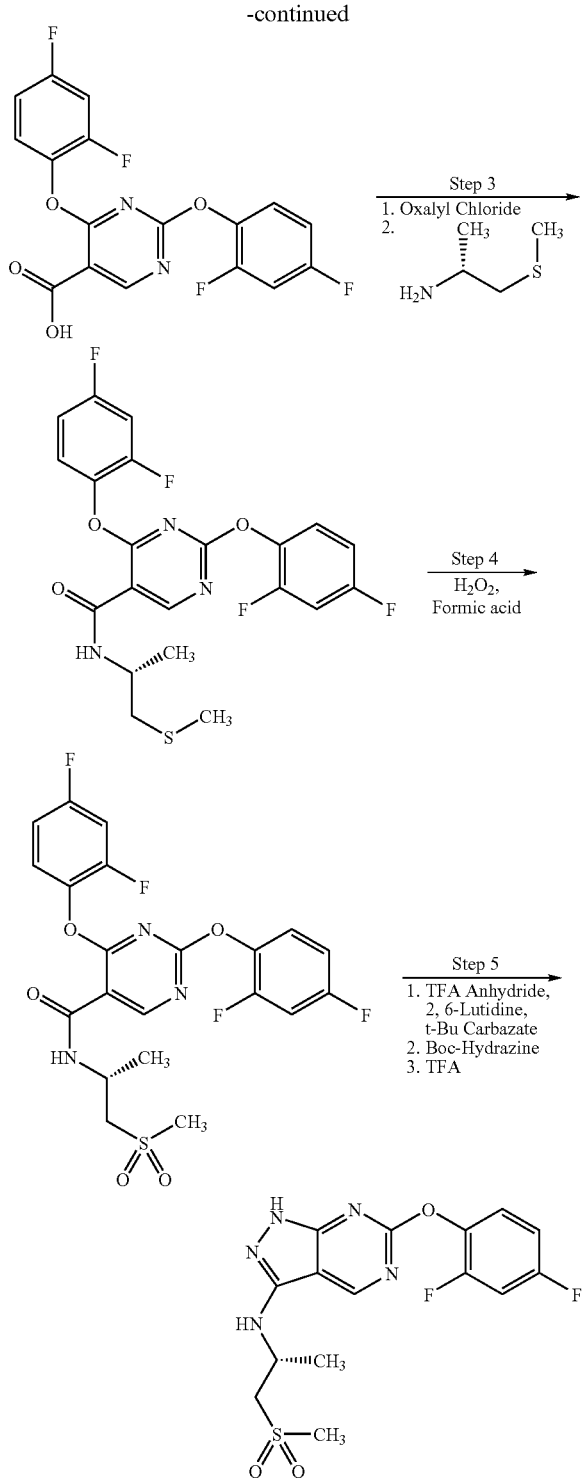

Step 1 5-Bromo-2,4-bis-(2,4-difluoro-phenoxu)-pyrimidine

Sodium Hydride (35.0 g, 875 mmol) was added to 400 mL dry THF, and the mixture was cooled in an ice bath for 30 minutes with stirring. 2,4-Difluorophenol (84.0 mL, 879 mmol) was added dropwise to the stirring mixture over a 75 minute period. The ice bath was removed, and 5-bromo-2,4-dichloropyrimidine (50.23 g, 220 mL was added. The reaction mixture was heated to 65° C. for 3.5 hours with stirring, then cooled to room temperature. The reaction mixture was partitioned between 750 mL of EtOAc and 400 mL water. The organic layer was dried over MgSO$_4$, filtered, and concentrated under reduced pressure. The residue was dissolved in 100 mL of hot EtOAc, and 300 mL hexanes was added. The mixture was cooled to room temperature and then refrigerated at 5° C. for 18 hours. The resulting crystalline precipitate was collected by filtration, washed with cold hexanes/EtOAc (3:1), and dried to give 63.66 g (70%) of 5-bromo-2,4-bis-(2, 4-difluoro-phenoxy)-pyrimidine. MS(M+H)=416.

Step 2 2,4-Bis-(2,4-difluoro-phenoxy)-pyrimidine-5-carboxylic acid

5-Bromo-2,4-bis-(2,4-difluoro-phenoxy)-pyrimidine (1.0 g, 2.41 mmol) was added to 30 mL of a 1:1 mixture of dry THF and diethyl ether. The mixture was cooled to 0° C. in an ice bath, and isopropyl magnesium chloride (1.45 mL of 2 M solution in diethyl ether, 2.41 mmol) was added dropwise to the stirring mixture. The reaction mixture was stirred at 0° C. for on hour, then dry CO$_2$ was bubbled through the stirring reaction mixture for 45 minutes. The reaction mixture was stirred under CO$_2$ atmosphere for another 30 minutes, then was concentrated under reduced pressure. The residue was taken up into a mixture of 30 mL water and 5 mL THF, and the mixture was acidified to pH=2 by dropwise addition of 10% aqueous HCl. The mixture was extracted wtih EtOAc and the organic layer was washed with water, dried (MgSO$_4$), filtered and concentrated under reduced pressure to give 950 mg of 2,4-bis-(2,4-difluoro-phenoxy)-pyrimidine-5-carboxylic acid. MS(M+H)=381.

Step 3 2,4-Bis-(2,4-difluoro-phenoxy)-pyrimidine-5-carboxylic acid ((R)-1-methyl-2-methylsulfanyl-ethyl)-amide 2,4-Bis-(2,4-difluoro-phenoxy)-pyrimidine-5-carboxylic acid (63.40 g, 166.7 mmol) was added to a mixture of dry dichloromethane (1 L) and dry DMF (0.5 mL), and the reaction mixture was cooled to 0° C. and stirred under nitrogen for 30 minutes. Oxalyl chloride (21.8 mL, 249.8 mmol) was added dropwise over three minutes, and the reaction mixture was stirred at 0° C. for 8 hours, then stirred at room temperature for 18 hours. The reaction mixture was concentrated under reduced pressure, and dichloromethane (500 mL) was added to the residue. The mixture was cooled to 0° C. with stirring in an ice bath for 30 minutes, and (R)-1-methyl-2-methylsulfanyl-ethylamine (26.3 g, 1.837 mmol) was added, followed by triethylamine (51.5 mL, 369 mmol) dropwise over 10 minutes. THe reaction mixtuer was stirred for one hour at 0° C., then stirred at room temperature for 20 hours. The reaction mixture was washed with water, and the organic layer was dried over MgSO$_4$, filtered and concentrated under reduced pressure to give 82.63 g of crude 2,4-bis-(2,4-difluoro-phenoxy)-pyrimidine-5-carboxylic acid ((R)-1-methyl-2-methylsulfanyl-ethyl)-amide as a viscous oil. MS(M+H)=468.

Step 4 2,4-Bis-(2,4-difluoro-phenoxy)-pyrimidine-5-carboxylic acid ((R)-2-methanesulfonyl-1-methyl-ethyl)-amide 2,4-Bis-(2,4-difluoro-phenoxy)-pyrimidine-5-carboxylic acid ((R)-1-methyl-2-methylsulfanyl-ethyl)-amide (82.63 g, 166.7 mmol) was dissolved in 700 mL dichloromethane. Formic acid (16.4 mL, 417 mmol) and hydrogen peroxide (47.6 mL of 30% weight aqueous solution, 833.5 mL) were added. The reaction mixture was stirred for 20 hours at room temperature, then was washed with water, 4% aqueous sodium bicarbonate, and brine. The organic layer was concentrated under reduced pressure, and the residue was dissolved in 280 mL of methyltert-butyl ether. Diethyl ether (600 mL) was added, and the resulting crystalline precipitate was collected by filtration, rinsed with diethyl ether, and dried to give 62.16 g of 2,4-bis-(2,4-difluoro-phenoxy)-pyrimidine-5-carboxylic acid ((R)-2-methanesulfonyl-1-methyl-ethyl)-amide. MS(M+H)=500.

Step 5 [6-(2,4-Difluoro-phenoxy)-1H-pyrazolo[3,4-d]pyrimidin-3-yl]-((R)-2-methanesulfonyl-1-methyl-ethyl)-amine 2,4-Bis-(2,4-difluoro-phenoxy)-pyrimidine-5-carboxylic acid ((R)-2-methanesulfonyl-1-methyl-ethyl)-amide (61.16 g, 122.5 mmol) was added to 600 mL dry dichloromethane, and the mixture was stirred under nitrogen. 2,6-lutidine (43.0 mL, 184 mmol) was added, and the mixture was cooled to 0° C. in an ice bath for 30 minutes with stirring. Trifluoroacetic anhydride (31.0 mL, 184 mmol) was added dropwise over five minutes, and the reaction mixture was stirred for 10 minutes at 0° C. The ice bath was removed and the reaction mixture was stirred for 3.5 hours. The reaction mixture was then cooled to 0° C. in an ice bath for 30 minutes, and tert-butyl carbazate (24.36 g, 184 mmol) was added in portions over five minutes. The ice bath was removed and the reaction mixture was stirred at room temperature for 12 hours. The reaction mixture was again cooled to 0° C. in an ice bath for 30 minutes, and trifluoroacetic acid (200 mL) was added in portions over 15 minutes. The reaction mixture was stirred for another 15 minutes, then the ice bath was removed and stirring was continued for two hours. The reaction mixture was concentrated under reduced pressure, and 500 mL dichloromethane was added to the residue. The mixture was cooled in an ice bath for 15 minutes, and 1.5 L of saturated aqueous sodium bicarbonate was slowly added in portions with stirring, resulting in an aqueous solution of pH=8 and the formation of a precipitate. The precipitate was collected by filtration and rinsed with water, followed by dichloromethane, and dried under vacuum at 80° C. to give 30.15 g (60%) of [6-(2,4-Difluoro-phenoxy)-1H-pyrazolo[3,4-d]pyrimidin-3-yl]-((R)-2-methanesulfonyl-1-methyl-ethyl)-amine. Mp=177.7-178.8° C., MS(M+H)=384.

Additional compounds prepared by the above procedure are shown in Table 1.

Example 6

[6-(2,4-Difluoro-phenoxy)-1H-pyrazolor3,4-d]pyrimidin-3-yl]-((R)-2-methanesulfonyl-1-methyl-ethyl)-amine The synthetic procedure of Example 1 is shown in Scheme 1.

SCHEME I

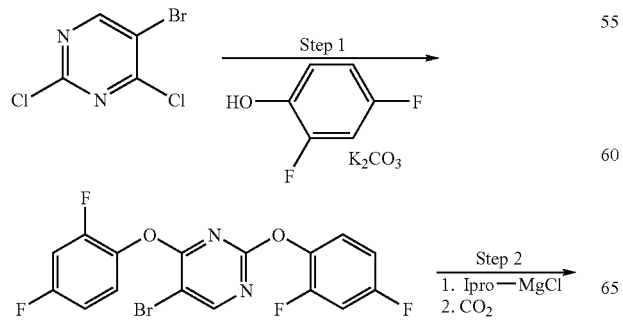

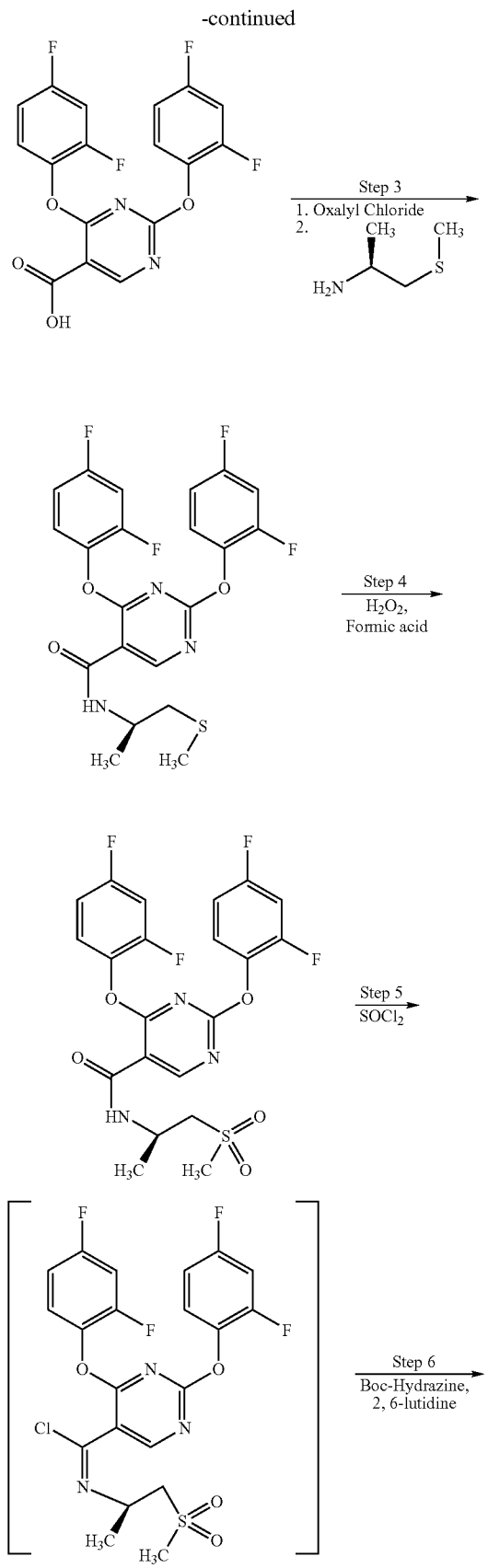

-continued

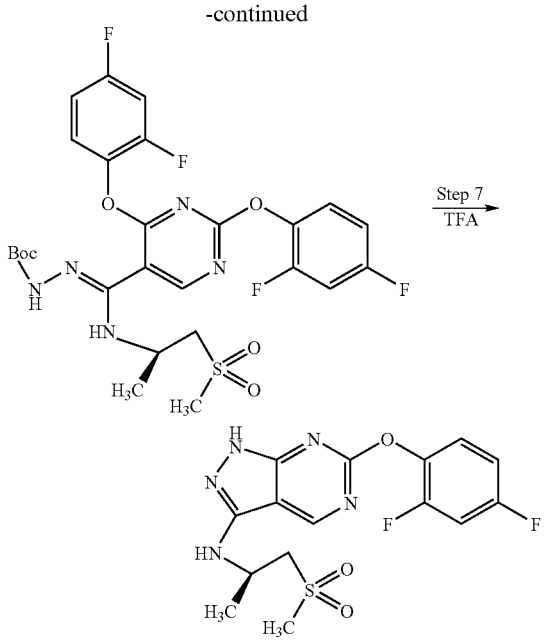

Step 1 5-Bromo-2,4-bis-(2,4-difluoro-phenoxy)-pyrimidine

To 1.45 kg of potassium carbonate in dry THF (2 l), under nitrogen and cooled in an ice bath was added 1.3 kg of 2,4-difluorophenol in THF (500 ml) over 30 minutes, followed by addition of 1.11 kg of 5-bromo-2,4-dichloropyrimidine in 1 l of THF. The reaction mixture was heated to 60° C. for 48 hours, then cooled to room temperature, and 4 L of heptane was added. The mixture was filtered, and the solid was washed with 5 L of 1/1 heptane/THF. The combined filtrates were concentrated under vacuum, the residue was suspended in 0.6 L of heptane and filtered. The solid was washed two times with 0.25 L of heptane and dried under vacuum at to give 1.975 kg of bromo-2,4-bis-(2,4-difluoro-phenoxy)-pyrimidine, MS(M+H)=416.

Step 2 2,4-Bis-(2,4-difluoro-phenoxy)-pyrimidine-5-carboxylic acid

In a 22 liter reactor, 5-bromo-2,4-bisdifluorophenoxy)pyrimidine (1.0 kg) was dissolved in 2-methyltetrahydrofuran (11 liters) and the resulting solution was cooled to −20° C. Isopropyl magnesium chloride.(1M in THF, 1.6 liters) was charged over 1 hour at −20° C. The reaction mixture was stirred for an additional 2.5 hours at −20° C. and then cooled to −25° C. (cooling jacket at −40° C.). Gaseous carbon dioxide was sparged into the reaction mixture for one hour. An initial exothermic reaction caused the internal reaction temperature to rise to −8° C. in the first quarter charge after, which the temperature dropped. The reaction mixture was stirred at −20° C. for an additional 30 minutes. The reaction was quenched by the slow addition of 10% aqueous ammonium chloride (2.5 liters), allowing the temperature rise to 0° C. The reaction mixture pH was adjusted to 2-3 by addition of 4N aqueous hydrochloric acid (1.05 liters). The layers were split and the organic layer washed with saturated brine solution (2.0 liters). The organic layer was concentrated under reduced pressure, and n-heptane (4.0 liters) was added to the residue. The mixture was allowed to reach room temperature over 12 hours. The resulting slurry was filtered ,washed with n-heptane, and dried in a vacuum oven at 40° C. to afford 2,4-bis-(2,4-difluoro-phenoxy)-pyrimidine-5-carboxylic acid as a white crystalline solid 870 grams (94.8% yield), MS(M+H)=381.

Step 3 2,4-Bis-(2,4-difluoro-phenoxy)-pyrimidine-5-carboxylic acid ((R)-1-methyl-2-methylsulfanyl-ethyl)-amide To 1.42 kg of 2,4-bis-(2,4-difluoro-phenoxy)-pyrimidine-5-carboxylic acid suspended in benzotrifluoride (5.2 l) was added 640 mL (2 equivalents) of oxalyl chloride and 3 mL of DMF. The mixture was stirred at room temperature overnight, and then was diluted with benzotrifluoride (2 L) and distilled under vacuum to about 3.5 L volume. The mixture was cooled below 5° C. and a solution of (R)-1-methyl-2-methylsulfanyl-ethylamine (480 g) and triethylamine (525 ml) in dichloromethane (1.5 l) was added, maintaining the temperature below 10° C. during the addition. The reaction mixture was stirred at room temperature for 30 minutes, and a mixture of dichloromethane (3 l) and aqueous citric acid was added. The organic phase was separated, the aqueous phase extracted with 2 L of dichloromethane, and the combined organic layers were washed with water, aqueous sodium bicarbonate solution, and again with water. The combined organic layers were then dried over sodium sulfate, filtered, and evaporated. The resulting crude 2,4-bis-(2,4-difluoro-phenoxy)-pyrimidine-5-carboxylic acid ((R)-1-methyl-2-methylsulfanyl-ethyl)-amide was used directly in the next step without further isolation.

Step 4 2,4-Bis-(2,4-difluoro-phenoxy)-pyrimidine-5-carboxylic acid ((R)-2-methanesulfonyl-1-methyl-ethyl)-amide In a 22 liter reactor, crude 2,4-bis-(2,4-difluoro-phenoxy)-pyrimidine-5-carboxylic acid ((R)-1-methyl-2-methylsulfanyl-ethyl)-amide (1.72 kg) was dissolved in dichloromethane (10 liters).and formic acid (423 grams). The reaction mixture was cooled on an ice bath to 17° C. and hydrogen peroxide (2.1 kg) was added. An initial exotherm to 37° C. was observed for the addition of the first 250 grams of hydrogen peroxide. The reaction mixture was then stirred for 12 hours at room temperature. The reaction phases were separated and the organic layer was successively washed with saturated sodium bicarbonate (2.0 liters), water (4.0 liters) and brine (2.0 liters). The reaction mixture was concentrated under reduced pressure at 50° C. to a foam. The foam was taken up in MTBE (1.5 liters), from which solid crystallized. The resulting slurry was allowed cooled to room temperature overnight. Diethyl ether (1.5 liters) was added, and the crystalline solid was filtered and washed with diethyl ether (2.0 liters) under nitrogen. The collected solid was dried in a vacuum oven at 35° C. for 48 hours to yield 1.46 kg (80%.) of 2,4-Bis-(2,4-difluoro-phenoxy)-pyrimidine-5-carboxylic acid ((R)-2-methanesulfonyl-1-methyl-ethyl)-amide, MS (M+H)=500.

Step 5 {[2,4-Bis-(2,4-difluoro-phenoxy)-pyrimidin-5-yl]-chloro-methyl}-((R)-2-methanesulfonyl-1-methyl-ethylidene)-amine 2,4-Bis(2,4-difluorophenoxy)pyrimidine-5-(2-methanesulfonyl-1-methylethyl)carboxamide (1.45 kg ) was charged into a 5 liter reactor and dissolved in thionyl chloride (1.9 liters). The reaction solution was heated to 73° C. (vigorous gas off at about 65° C.) for 12 hours to afford an orange-coloured solution. Excess thionyl chloride was distilled (1.2 liters) under low vacuum at 73° C., and the remaining thionyl chloride was driven off by the addition of toluene (1.5 liters) followed again by distillation. When the toluene distillation slowed down, tetrahydrofuran (2.0 liters) was charged and the thick residue was redissolved in THF before cooling down to 5-10° C. to afford a solution of {[2,4-bis-(2,4-difluoro-phenoxy)-pyrimidin-5-yl]-chloro-methyl}-((R)-2-methane-sulfonyl-1-methyl-ethylidene)-amine, MS(M+H)=518, which was not isolated but used directly in the next step in solution form.

Step 6 N'-[[2,4-Bis-(2,4-difluoro-phenoxy)-pyrimidin-5-yl]-((R)-2-methanesulfonyl-1-methyl-ethylamino)-methylenel-hydrazinecarboxylic acid tert-butyl ester The solution of {[2,4-bis-(2,4-difluoro-phenoxy)-pyrimidin-5-yl]-chloro-methyl}-(2-methanesulfonyl-1-methyl-ethylidene)-amine was added to a solution of BOC carbazate (766 g) and 2,6-lutidine (930 g) in tetrahydrofuran (2.0 liters) at 5° C. The reaction mixture was stirred at 25° C. for 24 hours. The reaction mixture was quenched with water (3.0 liters) diluted with methylene chloride (2.0 liters) and the reaction pH was adjusted to pH 3 by addition of 4N HCl (2.4 liters). The layers were separated and the organic layer was washed with saturated sodium bicarbonate (2.0 liters) and a 1:1 mixture of water and saturated brine. The organic layer was concentrated under reduced pressure for 12 hours to give N'-[[2,4-bis-(2,4-difluoro-phenoxy)-pyrimidin-5-yl]-((R)-2-methanesulfonyl-1-methyl-ethylamino)-methylene]-hydrazinecarboxylic acid tert-butyl ester (2.0 kg, quantitative) as a pale yellow powder.

Step 7 [6-(2,4-Difluoro-phenoxy)-1H-pyrazolo[3,4-d]pyrimidin-3-yl]-((R)-2-methanesulfonyl-1-methyl-ethyl)-amine A solution of 1.02 kg of N'-[[2,4-bis-(2,4-difluoro-phenoxy)-pyrimidin-5-yl]-((R)-2-methanesulfonyl-1-methyl-ethylamino)-methylene]-hydrazinecarboxylic acid tert-butyl ester in toluene (6-8 l) and conc HCl. (500 ml) was stirred at room temperature overnight. The reaction mixture was diluted with iso-propyl acetate (3.5 L) and a saturated aqueous sodium bicarbonate solution was added. The resulting solid precipitate was collected by filtration, washed with aqueous sodium bicarbonate, water, then with methyl t-butyl ether, and dried under vacuum. The material was recrystallized from isobutanol to give 455 g of [6-(2,4-difluoro-phenoxy)-1H-pyrazolo[3,4-d]pyrimidin-3-yl]-((R)-2-methanesulfonyl-1-methyl-ethyl)-amine. Mp=177.7-178.8° C., MS(M+H)=384.

Example 7

3-[3-(2-Chloro-phenyl)-6-(2,4-difluoro-phenoxy)-1H-indazol-4-yloxy]-propane-1,2-diol The synthetic procedure of Example 1 is shown in Scheme E.

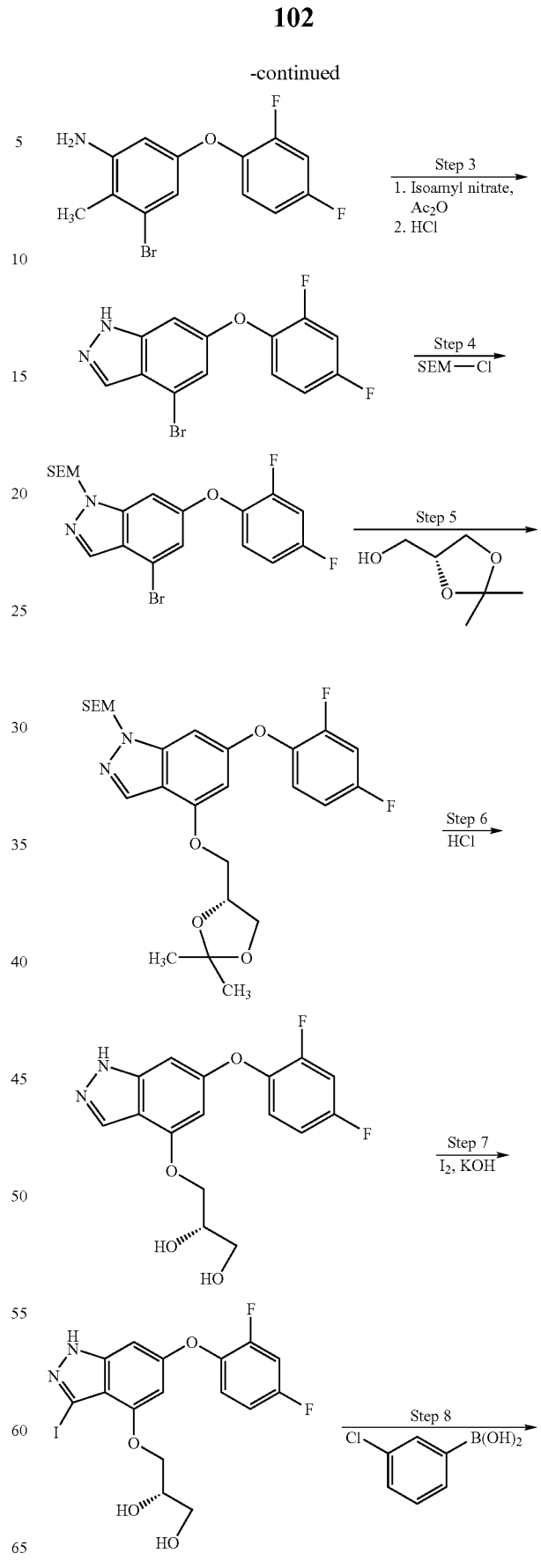

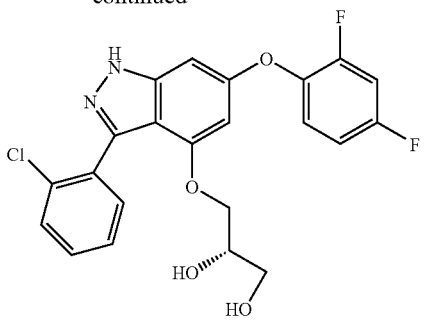

Step 1 1-Bromo-5-(2,4-difluoro-phenoxy)-2-methyl-3-nitro-benzene

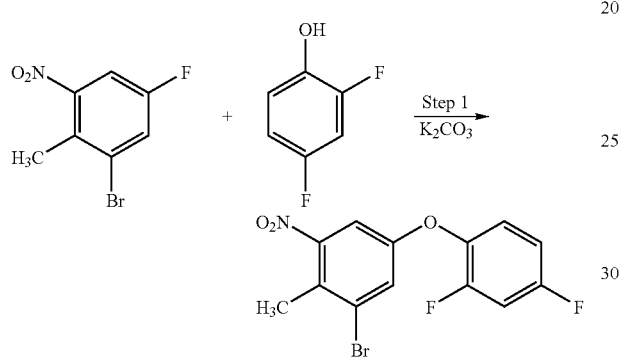

1-Bromo-5-fluoro-2-methyl-3-nitro-benzene (9.40 g, 41.45 mmol) was dissolved in 90 mL dry DMF, and 2,4-difluorophenol (5.93 g, 45.58 mmol) and potassium carbonate (6.70 g, 45.58 mmol) were added. The reaction mixture was placed under nitronge and heated to 120° C. with stirring for 18 hours. The reaction mixture was cooled and concentrated under reduced pressure, and the residue was partitioned between water and EtOAc. The organic phase was separated, washed with 1N aqueous NaOH and brine, dried (MgSO₄), filtered and concentrated under reduced pressure. The residue was chromatographed through silica (0%-6% EtOAc in hexanes) to give 8.484 g of 1-bromo-5-(2,4-difluoro-phenoxy)-2-methyl-3-nitro-benzene.

Step 2 3-Bromo-5-(2,4-difluoro-phenoxy)-2-methyl-phenylamine

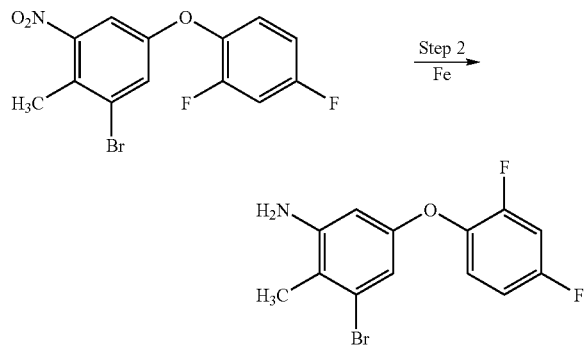

1-Bromo-5-(2,4-difluoro-phenoxy)-2-methyl-3-nitro-benzene (7.31 g, 21.2 mmol) was dissolved in 145 mL EtOH and 35 mL water was added, followed by addition of ammonium chloride (3.63 g, 67.9 mmol) and powdered iron (3.56 g, 63.8 mmol). The reaction mixture was placed under nitrogen atmosphere and heated to 85° C. for 2.5 hours. The reaction mixture was cooled, filtered through celite, and the filtrate was concentrated under reduced pressure. The residue was partitioned between water and EtOAc and the organic phase was separated, washed with brine, dried (MgSO₄), filtered and concentrated under reduced pressure. The residue was chromatographed through silica (0%-25% EtOAc in hexanes) to give 7.583 g of 3-bromo-5-(2,4-difluoro-phenoxy)-2-methyl-phenylamine, MS(M+H)=314.

Step 3 4-Bromo-6-(2,4-difluoro-phenoxy)-1H-indazole

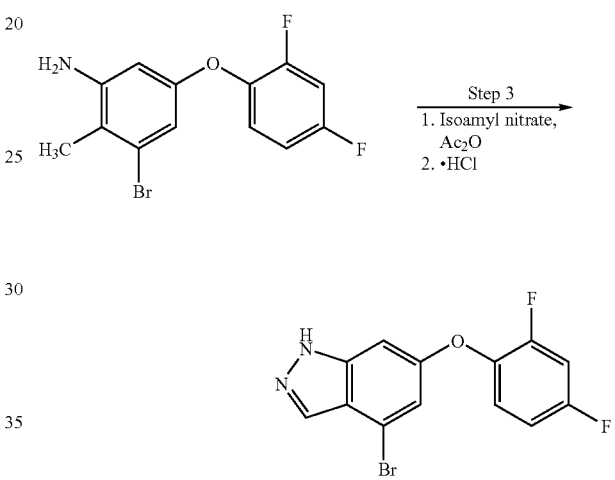

3-Bromo-5-(2,4-difluoro-phenoxy)-2-methyl-phenylamine (5.31 g, 16.9 mmol) was dissolved in 50 mL dry benzene, and acetic anhydride (5.17 g, 50.7 mmol) and potassium acetate (1.69 g, 17.2 mmol) were added. The reaction mixture was placed under nitrogen atmosphere and heated to 80° C. with stirring for 10 minutes. Isoamyl nitrate (3.39 mL, 25.4 mmol) was added dropwise over 30 minutes, after which the reaction mixture was stirred at 80° C. under nitrogen for 17 hours. The reaction mixture was cooled and filtered, and the filtrate was concentrated under reduced pressure. Water (8 mL) and concentrated HCl (16 mL of 6N aqueous solution) were added, and the mixture was heated to 55° C. Methanol (100 mL) was added, and the mixture was heated to 80° C. The mixture was cooled and concentrated under reduced pressure, and the residue was partitioned between water and ethyl acetate. The organic layer was separated and concentrated under reduced pressure. The residue was partitioned betwee methylene chloride and saturated sodium bicarbonate. The organic layer was separated, washed with brine, dried (MgSO₄), filtered and concentrated under reduced pressure. The residue was chromatographed through silica (0%-25% EtOAc in hexanes) to give 3.18 g of 4-bromo-6-(2,4-difluoro-phenoxy)-1H-indazole.

Step 4 4-Bromo-6-(2,4-difluoro-phenoxy)-1-(2-trimethylsilanyl-ethoxymethyl)-1H-indazole

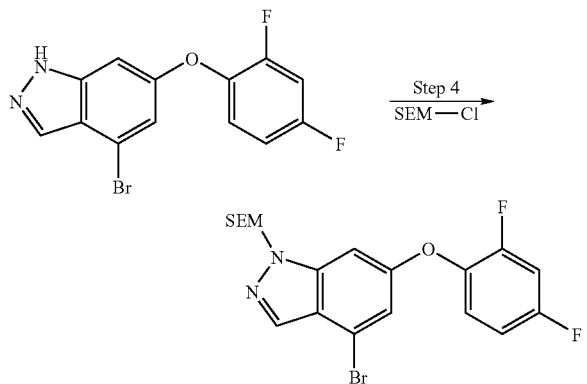

Sodium hydride (98 mg of 60% weight in mineral oil, 2.45 mmol) was washed with hexanes and added to 5 mL of dry DMF, and the mixture was placed under nitrogen atmosphere and cooled to 0° C. 4-Bromo-6-(2,4-difluoro-phenoxy)-1H-indazole (0.50 g, 1.54 mmol) dissolved in 5 mL dry DMF was added to the reaction mixture. The reaction mixture was stirred for 30 minutes at room temperature, then cooled to 0° C. again. (2-Chloromethoxy-ethyl)-trimethyl-silane (0.386 g, 2.32 mmol) was added, and the reaction mixture was stirreed for 21 hours at room temperature under nitrogen. The reaction mixture was partitioned between water and ethyl acetate, and the organic phase was separated, washed with brine and water, dried (MgSO$_4$), filtered and concentrated under reduced pressure. The residue was chromatographed through silica (0%-25% EtOAc in hexanes) to give 0.181 g of 4-bromo-6-(2,4-difluoro-phenoxy)-1-(2-trimethylsilanyl-ethoxymethyl)-1H-indazole, MS(M+H)=455.

Step 5 6-(2,4-Difluoro-phenoxy)-4-(2,2-dimethyl-[1,3]dioxolan-4-ylmethoxv)-1-(2-trimethylsilanyl-ethoxymethyl)-1H-indazole

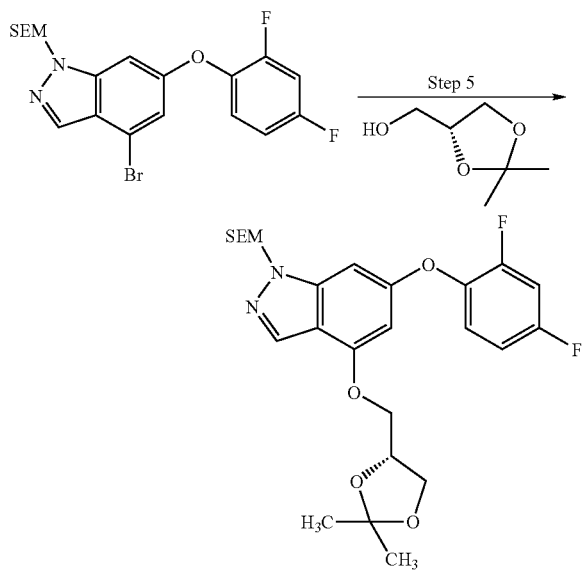

4-Bromo-6-(2,4-difluoro-phenoxy)-1-(2-trimethylsilanyl-ethoxymethyl)-1H-indazole (2.0 g, 4.39 mmol) was dissolved in 30 mL toluene, and (2,2-dimethyl-[1,3]dioxolan-4-yl)-methanol (0.871 g, 6.59 mmol) was added, followed by 2-di-(tert-butylphosphino)-2'-[N,N-dimethylamino]biphenyl (0.150 g, 0.439 mmol), palladium diacetate (0.099 g, 0.439 mmol) and cesium carbonate (3.577g, 10.98 mmol). The reaction mixture was placed under argon and heated to 70° C. with stirring for 18 hours. The reaction mixture was cooled, filtered through Celite, and the filtrate was evaporated under reduced pressure. The residue was chromatographed through silica (0%-1 5% EtOAc in hexanes) to give 0.923 g of 6-(2,4-dDifluoro-phenoxy)-4-(2,2-dimethyl-[1,3]dioxolan-4-ylmethoxy)-1-(2-trimethylsilanyl-ethoxymethyl)-1H-indazole.

Step 6 3-[6-(2,4-Difluoro-phenoxy)-1H-indazol-4-yloxyl-propane-1,2-diol

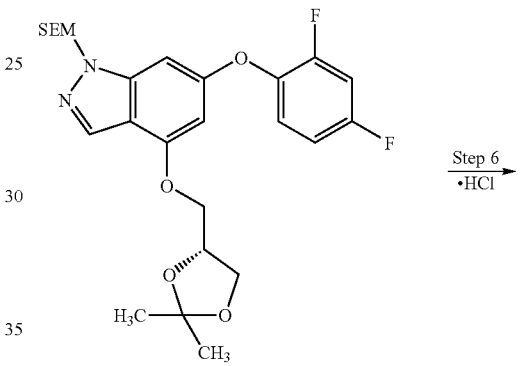

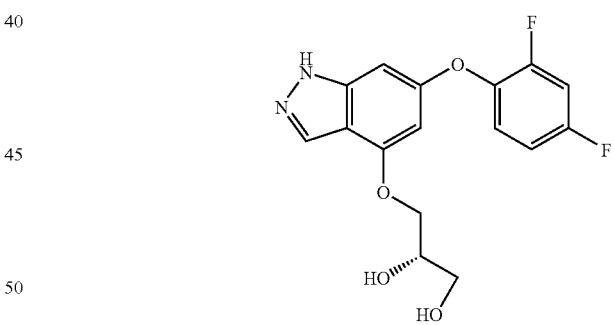

6-(2,4-Difluoro-phenoxy)-4-(2,2-dimethyl-[1,3]dioxolan-4-ylmethoxy)-1-(2-trimethylsilanyl-ethoxymethyl)-1H-indazole (0.905 g, 1.79 mmol) was dissolved in 20 mL of MeOH. Water (12 mL) and concentrated HCl (12 mL) were added, and the reaction mixture was sealed and heated to 90° C. for 30 minutes. The reaction mixture was cooled and concentrated under reduced pressure, and the residue was taken up in MeOH, made pH neutral by dropwise addition of aqueous NH$_4$OH solution, and concentrated to dryness under reduced pressure. The residue was chromatographed through silica (0%-1 0% EtOAc in hexanes) to give 0.522 g of 3-[6-(2,4-difluoro-phenoxy)-1H-indazol-4-yloxy]-propane-1,2-diol, MS(M+H)=337.

Step 7 3-[6-(2,4-Difluoro-phenoxy)-3-iodo-1H-indazol-4-yloxyl-propane-1,2-diol

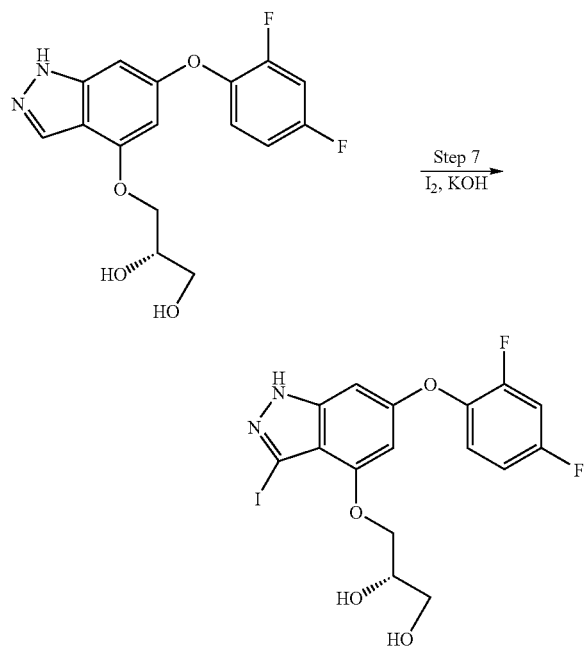

3-[6-(2,4-Difluoro-phenoxy)-1H-indazol-4-yloxy]-propane-1,2-diol (0.45 g, 1.34 mmol) was dissolved in 5 mL of dry DMF, and powdered KOH (0.288 g, 5.1 mmol) was added. The reaction mixture was stirred under nitrogen for 10 minutes at room temperature, and iodine (0.536 g, 2.11 mmol) was added in two portions. The reaction mixture was stirred for 90 minutes. The reaction mixture was partitioned between EtOAc and 5% aqueous sodium bisulfite solution, and the organic layer was separated, dried (MgSO$_4$), filtered and concentrated under reduced pressure. The residue was chromatographed through silica (0%-5% MeOH in dichloromethane) to give 0.408 g of 3-[6-(2,4-difluoro-phenoxy)-3-iodo-1H-indazol-4-yloxy]-propane-1,2-diol, MS(M+H)=436.

Step 8 3-[3-(2-Chloro-phenyl)-6-(2,4-difluoro-phenoxy)-1H-indazol-4-yloxyl]-propane-1,2-diol

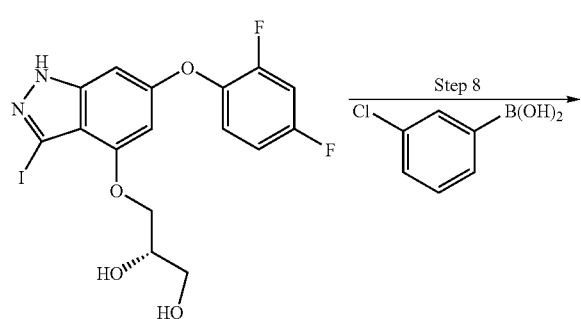

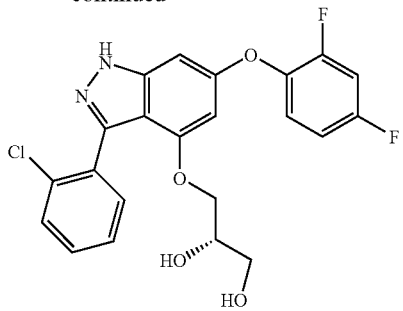

3-[6-(2,4-Difluoro-phenoxy)-3-iodo-1H-indazol-4-yloxy]-propane-1,2-diol (230 mg, 0.498 mmol) was dissolved in 18 mL of dioxane. 2-Chlorophenyl boronic acid (0.174 g, 1.11 mmol), sodium carbonate (0.174 g, 1.64 mmol), and tetrakis-(triphenylphosphino)-palladium (114 mg) were added. The reaction mixture was placed under argon atmosphere, and heated to 100° C. (reflux) with stirring for 26 hours. The reaction mixture was cooled to room temperature and partitioned between EtOAc and saturated aqueous sodium carbonate. The organic layer was separated, washed with saturated aqueous sodium carbonate and brine, dried (MgSO$_4$), filtered and concentrated under reduced pressure. The residue was chromatographed through silica (0%-5% MeOH in dichloromethane), then by preparative TLC (5% MeOH in dichloromethane) to give 93 mg of 3-[3-(2-chloro-phenyl)-6-(2,4-difluoro-phenoxy])-1H-indazol-4-yloxy]-propane-1,2-diol, MP=93.3-94.6° C., MS(M+H)=447.

Additional compounds were prepared by the above procedure, and are shown in Table 1.

Example 8

This example illustrates a p38 (MAP) kinase in vitro assay useful for evaluating the compounds of the invention.

The p38 MAP kinase inhibitory activity of compounds of this invention in vitro was determined by measuring the transfer of the γ-phosphate from γ-$^{33}$P-ATP by p-38 kinase to Myelin Basic Protein (MBP), using a minor modification of the method described in Ahn, et al., *J. Biol. Chem.* 266:4220-4227 (1991).

The phosphorylated form of the recombinant p38 MAP kinase was co-expressed with SEK-1 and MEKK in *E. Coli* (see, Khokhlatchev, et al., *J. Biol. Chem.* 272:11057-11062 (1997)) and then purified by affinity chromatography using a Nickel column.

The phosphorylated p38 MAP kinase was diluted in kinase buffer (20 mM 3-(N-morpholino)propanesulfonic acid, pH 7.2, 25 mM β-glycerol phosphate, 5 mM ethylene glycol-bis (beta-aminoethyl ether)-N,N,N',N'-tetraacetic acid, 1 mM sodium ortho-vanadate, 1 mM dithiothreitol, 40 mM magnesium chloride). Test compound dissolved in DMSO or only DMSO (control) was added and the samples were incubated for 10 min at 30° C. The kinase reaction was initiated by the addition of a substrate cocktail containing MBP and γ-$^{33}$P-ATP. After incubating for an additional 20 min at 30° C., the reaction was terminated by adding 0.75% phosphoric acid. The phosphorylated MBP was then separated from the residual γ-$^{33}$P-ATP using a phosphocellulose membrane (Millipore, Bedfrod, Mass.) and quantitated using a scintillation counter (Packard, Meriden, Conn.).

Using the above procedure, the compounds of the invention were found to be inhibitors of p38 MAP kinase. For example, 2-Bromo-N-[6-(2,4-difluoro-phenoxy)-1H-pyrazolo[3,4-d]pyrimidin-3-yl]-benzamide a p38 $IC_{50}$ (uM) of approximately 0.016, and 3-[3-(2-Chloro-phenyl)-6-(2,4-difluoro-phenoxy)-1H-indazol-4-ylamino]-propane-1,2-diol exhibited a p38 $IC_{50}$ (uM) of approximately 0.004.

Example 9

Formulations

Pharmaceutical preparations for delivery by various routes are formulated as shown in the following Tables. "Active ingredient" or "Active compound" as used in the Tables means one or more of the Compounds of Formula I.

Composition for Oral Administration

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
| --- | --- |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | grams |
| --- | --- |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 10

In Vitro Assay to Evaluate the Inhibition of LPS-Induced TNF-α Production in THP1 Cells This example illustrates an in vitro assay to evaluate the inhibition of LPS-induced TNF-α production in THP1 cells.

The ability of the compounds of this invention to inhibit the TNF-α release was determined using a minor modification of the methods described in Blifeld, et al. *Transplantation*, 51:498-503 (1991).

(a) Induction of TNF Biosynthesis:

THP-1 cells were suspended in culture medium [RPMI (Gibco-BRL, Gailthersburg, Md.) containing 15% fetal bovine serum, 0.02 mM 2-mercaptoethanol], at a concentration of $2.5 \times 10^6$ cells/mL and then plated in 96 well plate (0.2 mL aliquots in each well). Test compounds were dissolved in DMSO and then diluted with the culture medium such that the final DMSO concentration was 5%. Twenty five μL aliquots of test solution or only medium with DMSO (control) were added to each well. The cells were incubated for 30 min., at 37° C. LPS (Sigma, St. Louis, Mo.) was added to the wells at a final concentration of 0.5 μg/ml, and cells were incubated for an additional 2 h. At the end of the incubation period, culture supernatants were collected and the amount of TNF-α present was determined using an ELISA assay as described below.

(b) ELISA Assay:

The amount of human TNF-α present was determined by a specific trapping ELISA assay using two anti-TNF-α antibodies (2TNF-H12 and 2TNF-H34) described in Reimund, J. M., et al. *GUT.* Vol. 39(5), 684-689 (1996).

Polystyrene 96-well plates were coated with 50 μl per well of antibody 2TNF-H12 in PBS (10 μg/mL) and incubated in a humidified chamber at 4° C. overnight. The plates were washed with PBS and then blocked with 5% nonfat-dry milk in PBS for 1 hour at room temperature and washed with 0.1% BSA (bovine serum albumin) in PBS.

TNF standards were prepared from a stock solution of human recombinant TNF-α (R&D Systems, Minneapolis, Minn.). The concentration of the standards in the assay began at 10 ng/mL followed by 6 half log serial dilutions.

Twenty five pL aliquots of the above culture supernatants or TNF standards or only medium (control) were mixed with 25 μL aliquots of biotinylated monoclonal antibody 2TNF-H34 (2 μg/mL in PBS containing 0.1% BSA) and then added to each well. The samples were incubated for 2 hr at room temperature with gentle shaking and then washed 3 times with 0.1% BSA in PBS. 50 μl of peroxidase-streptavidin (Zymed, S. San Francisco, Calif.) solution containing 0.416 μg/mL of peroxidase-streptavidin and 0.1% BSA in PBS was added to each well. The samples were incubated for an additional 1 hr at room temperature and then washed 4 times with 0.1% BSA in PBS. Fifty μL of O-phenylenediamine solution (1 μg/mL O-phenylene-diamine and 0.03% hydrogen peroxide in 0.2M citrate buffer pH 4.5) was added to each well and the samples were incubated in the dark for 30 min., at room temperature. Optical density of the sample and the reference were read at 450 nm and 650 nm, respectively. TNF-α levels were determined from a graph relating the optical density at 450 nm to the concentration used.

Example 11

In Vitro Assay to Evaluate the Inhibition of LPS-Induced TNF-α Production in THP1 Cells This example illustrates an in vivo assay to evaluate the inhibition of LPS-induced TNF-α production in mice (or rats).

The ability of the compounds of this invention to inhibit the TNF-α release, in vivo, was determined using a minor modification of the methods described in described in Zanetti, et. al., *J. Immunol.*, 148:1890 (1992) and Sekut, et. al., *J. Lab. Clin. Med.*, 124:813 (1994).

Female BALB/c mice weighing 18-21 grams (Charles River, Hollister, Calif.) were acclimated for one week. Groups containing 8 mice each were dosed orally either with the test compounds suspended or dissolved in an aqueous vehicle containing 0.9% sodium chloride, 0.5% sodium carboxymethyl-cellulose, 0.4% polysorbate 80, 0.9% benzyl alcohol (CMC vehicle) or only vehicle (control group). After 30 min., the mice were injected intraperitoneally with 20 μg of LPS (Sigma, St. Louis, Mo.). After 1.5 h, the mice were sacrificed by $CO_2$ inhalation and blood was harvested by cardiocentesis. Blood was clarified by centrifugation at 15,600×g for 5 min., and sera were transferred to clean tubes and frozen at −20° C. until analyzed for TNF-α by ELISA assay (Biosource International, Camarillo, Calif,) following the manufacturer's protocol.

Example 12

Adjuvant-Induced Arthritis in Rats

AIA-induced arthritis is evaluated using the procedure of Badger et al., *Arthritis & Rheumatism*, 43(1) pp 175-183 (2000) AIA is induced by a single injection of 0.75 mg of parrafin-suspended Mycobacterium Butycricum) into male Lewis rats. Hindpaw volume is measued by water displacement on days 15, 20 and 30. A set of control animals is dosed with tragacanth. Test compounds in 0.5% tragacanth are administered orally at 3, 10, 30 and 60 mg/kg/day dosages. Indomethacin is used as a positive control. Percentage inhibition of hindpaw edema is calculated by 1-[AIA(treated)/AIA(control)]×100 where AIA (treated) and AIA (control) represent the mean paw volume.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the formula:

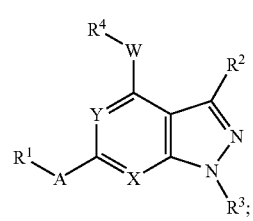

Ia or a pharmaceutically acceptable salt thereof, wherein:
R¹ is optionally substituted phenyl;
R² is —NHR$^a$, —NHSO$_2$R$^a$, —NHC(=O)R$^a$,
  wherein
    R$^a$ is hydrogen, C$_{1-6}$alkyl, C$_{3-7}$cycloalkyl, C$_{3-7}$cycloalkyl-C$_{1-4}$alkyl, C$_{3-7}$cycloalkenyl, C$_{3-7}$cycloalkenyl-C$_{1-4}$alkyl, halo-C$_{1-6}$alkyl, halo-C$_{3-7}$cycloalkyl, hydroxy-C$_{1-6}$alkyl, C$_{1-6}$alkylsulfonylC$_{1-6}$ alkyl, C$_{1-6}$alkylsulfanyl-C$_{1-6}$ alkyl, arylsulfonyl-C$_{1-6}$alkyl, aryl, aryl-C$_{1-6}$alkyl, heteroaryl, heteroaryl-C$_{1-6}$alkyl, C$_{1-6}$alkylsulfonamidylC$_{1-6}$alkyl, C$_{1-6}$alkoxycarbonylamino-C$_{1-6}$alkyl, C$_{1-6}$alkoxycarbonyl-C$_{1-6}$alkyl, C$_{1-6}$alkoxyaminocarbonyl-C$_{1-6}$ alkyl, aminocarbonyl-C$_{1-6}$alkyl, C$_{1-6}$alkylaminocarbonyl-C$_{1-6}$ alkyl, carboxy-C$_{1-6}$alkyl, heterocyclyl, heterocyclylalkyl, C$_{1-6}$alkylcarbonyl-C$_{1-6}$alkyl, heterocyclyl-C$_{1-6}$alkyl, aryl-C$_{1-6}$ alkyl, amino-C$_{1-6}$alkyl, N—C$_{1-6}$alkylamino-C$_{1-6}$ alkyl, N,N-di-C$_{1-6}$alkylamino-C$_{1-6}$alkyl, C$_{1-6}$alkoxy-C$_{1-6}$alkyl, or heteroaryl-C$_{1-6}$alkyl,
R³ is hydrogen;
R⁴ is hydrogen, C$_{1-6}$alkyl, or hetero-C$_{1-6}$alkyl
X and Y are nitrogen
W is a bond, or NR$^f$;
  wherein
    R$^f$ is hydrogen, and
A is O.

2. The compound of claim 1, wherein R¹ is 2-halophenyl or 2,4-dihalophenyl.

3. The compound of claim 2, wherein W is NR$^f$ and R⁴ is hetero-C$_{1-6}$alkyl.

4. The compound of claim 2, wherein W is a bond and R⁴ is hydrogen.

5. The compound of claim 2, wherein R² is —NHR$^a$.

6. The compound of claim 5, wherein R$^a$ is C$_{1-6}$alkyl, C$_{3-7}$cycloalkyl, C$_{3-7}$cycloalkyl-C$_{1-4}$alkyl, C$_{3-7}$cycloalkenyl, C$_{3-7}$cycloalkenyl-C$_{1-4}$alkyl, C$_{1-6}$alkylsulfonylC$_{1-6}$alkyl, aryl or heteroaryl.

7. The compound of claim 5, wherein R$^a$ is C$_{1-6}$alkyl or C$_{1-6}$alkylsulfonylC$_{1-6}$alkyl.

8. The compound of claim 1, wherein said compound is of the formula:

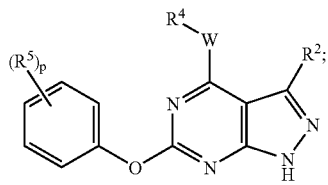

II wherein:
p is from 0 to 4;
each R⁵ is independently halo, alkyl, alkoxy, haloalkyl, haloalkoxy or cyano; and
W, R² and R⁴ are as recited in claim 1.

9. The compound of claim 8, wherein W is NR$^f$ and R⁴ is hetero-C$_{1-6}$alkyl.

10. The compound of claim 8, wherein W is a bond and R⁴ is hydrogen.

11. The compound of claim 10, wherein R² is —NHR$^a$.

12. The compound of claim 11, wherein R$^a$ is C$_{1-6}$alkyl, or C$_{1-6}$alkylsulfonylC$_{1-6}$alkyl.

13. The compound of claim 8, wherein said compound is of the formula:

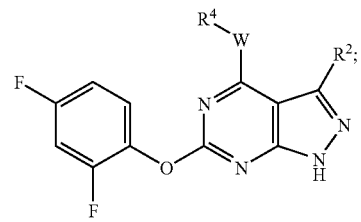

III wherein W, R² and R⁴ are as recited in claim 8.

14. The compound of claim 13, wherein R² is —NHR$^a$, and R$^a$ is C$_{1-6}$-alkyl or C$_{1-6}$alkylsulfonylC$_{1-6}$alkyl.

15. The compound of claim 14, wherein W is a bond and R⁴ is hydrogen.

16. A composition comprising:
(a) a pharmaceutically acceptable excipient; and
(b) a compound of claim 1.

17. A compound selected from the group consisting of:
[6-(2,4Difluoro-phenoxy)-1H-pyrazolo[3,4-d]pyrimidin-3-yl]-isopropyl-amine;
Thiophene-2-carboxylic acid [6-(2,4difluoro-phenoxy)-1H-pyrazolo[3,4-d]pyrimidin-3-yl]-amide;
Cyclopentanecarboxylic acid [6-(4-fluoro-phenoxy)-1H-pyrazolo[3,4-d]pyrimidin-3-yl]-amide;
Cyclohexanecarboxylic acid [6-(2,4-difluoro-phenoxy)-1H-pyrazolo [3,4-d]pyrimidin-3-yl]-amide;
Cyclobutanecarboxylic acid [6-(2,4-difluoro-phenoxy)-1H-pyrazolo [3,4-d]pyrimidin-3-yl]-amide;
2-Chloro-N-[6-(2,4-difluoro-phenoxy)-1H-pyrazolo[3,4-d]pyrimidin-3-yl]-benzamide;
Cyclopentanecarboxylic acid [6-(2-fluoro-phenoxy)-1H-pyrazolo[3,4-d]pyrimidin-3-yl]-amide;
N-[6-(2,4-Difluoro-phenoxy)-1H-pyrazolo[3,4-d]pyrimidin-3-yl]-3-methoxy-benzamide;
N-[6-(2,4-Difluoro-phenoxy)-1H-pyrazolo[3,4-d]pyrimidin-3-yl]-4-methoxy-benzamide;
4-[6-(2,4-Difluoro-phenoxy)-1H-pyrazolo[3,4-d]pyrimidin-3-ylcarbarnoyl]-piperidine-1-carboxylic acid benzyl ester;
N-[6-(2,4-Difluoro-phenoxy)-1H-pyrazolo[3,4-d]pyrimidin-3-yl]-benzenesulfonamide;
N-[6-(2,4-Difluoro-phenoxy)-1H-pyrazolo[3,4-d]pyrimidin-3-yl]-2-trifluoromethyl-benzamide;
2-Bromo-N-[6-(2,4-difluoro-phenoxy)-1H-pyrazolo[3,4-d]pyrimidin-3-yl]-benzamide;
Ethanesulfonic acid [6-(2,4-difluoro-phenoxy)-1H-pyrazolo[3,4-d]pyrirnidin-3-yl]-amide;
Cyclopentanecarboxylic acid [6-(2,4-difluoro-phenylsulfanyl)-1H-pyrazolo[3,4-d]pyrimidin3yl]-amide;
4-[6-(2,4-Difluoro-phenoxy)-1H-pyrazolo[3,4-d]pyrimidin-3 -ylcarbainoyl]-piperidine-1-carboxylic acid methyl ester;
Furan-2-carboxylic acid [6-(2,4-difluoro-phenoxy)-1H-pyrazolo[3,4-d]pyrimidin-3-yl]-amide;
1-Methanesulfonyl-piperidine-4-carboxylic acid [6-(2,4-difluoro-phenoxy)-1H-pyrazolo[3,4-d]pyrimidin-3-yl]-amide;
Piperidine-4-carboxylic acid [6-(2,4-difluoro-phenoxy)-1H-pyrazolo [3,4-d]pyrimidin-3-yl]-amide;
3-Benzyl-6-(2,4-difluoro-phenoxy)-1H-pyrazolo[3,4-d] pyrimidine;

3-Butyl-6-(2,4-difluoro-phenoxy)-1H-pyrazolo[3,4-d]pyrimidine;
3-[6-(2,4-Difluoro-phenoxy)-1H-pyrazolo[3,4-d]pyrimidin-3-yl]-propan-1-ol;
6-(2,4-Difluoro-phenoxy)-3-propyl-1H-pyrazolo [3,4-d] pyrimidine;
6-(2,4-Difluoro-phenoxy)-3-(1,1-dimethyl-but-3-enyl)-1H-pyrazolo[3,4-d]pyrimidine;
6-(2,4-Difluoro-phenoxy)-3-phenethyl-1H-pyrazolo [3,4-d]pyrimidine;
6-(2,4-Difluoro-phenoxy)-3-(4,4,4-trifluoro-butyl)-1H-pyrazolo [3,4-d]pyrimidine;
3-Cyclopent-2-enylmethyl-6-(2,4-difluoro-phenoxy)-1H-pyrazolo[3,4-d]pyrimidine;
6-(2,4-Difluoro-phenoxy)-3-(2,2-dimethyl-but-3-enyl)-1H-pyrazolo [3,4-d]pyrimidine;
3-Cyclohexylmethyl-6-(2,4-difluoro-phenoxy)-1H-pyrazolo[3,4-d]pyrimidine;
2-[6-(2,4-Difluoro-phenoxy)-1H-pyrazolo[3,4-d]pyrimidin-3-ylmethyl]-cyclopent-3-enol;
3-Cyclopent-3-enyl-6-(2,4-difluoro-phenoxy)-1H-pyrazolo[3,4-d]pyrimidine;
3-(4,4-Difluoro-cyclohexyl)-6-(2,4-difluoro-phenoxy)-1H-pyrazolo[3,4-d]pyrimidine;
6-(2,4-Difluoro-phenoxy)-3-(2-pyridin-3-yl-ethyl)-1H-pyrazolo[3,4-d]pyrimidine;
3-[6-(2,4-Difluoro-phenoxy)-1H-pyrazolo [3,4-d]pyrimidin-3-ylmethyl]-cyclopentanol;
N-[6-(2,4-Difluoro-phenoxy)-1H-pyrazolo[3,4-d]pyrimidin-3-yl]-isobutyramide;
N-[6-(2,4-Difluoro-phenoxy)-1H-pyrazolo[3,4-d]pyrimidin-3-yl]-benzamide;
Cyclopropanecarboxylic acid [6-(2,4-difluoro-phenoxy)-1H-pyrazolo[3,4-d]pyrimidin-3-yl]-amide;
Cyclopentanecarboxylic acid [6-(2,4-difluoro-phenoxy)-1H-pyrazolo[3,4-d]pyrimidin-3-yl]-amide;
N-[6-(2,4-Difluoro-phenoxy)-1H-pyrazolo[3,4-d]pyrimidin-3-yl]-acetamide;
N-[6-(2,4-Difluoro-phenoxy)-1H-pyrazolo[3,4-d]pyrimidin-3-yl]-2-fluoro-benzamide;
N-[6-(2,4-Difluoro-phenoxy)-1H-pyrazolo[3,4-d]pyrimidin-3-yl]-2-methoxy-benzamide;
[6-(2,4-Difluoro-phenoxy)-1H-pyrazolo[3,4-d]pyrimidin-3-yl]-carbamic acid benzyl ester;
1-Methanesulfonyl-3-methyl-piperidine-4-carboxylic acid [6-(2,4-difluoro-phenoxy)-1H-pyrazolo[3,4-d]pyrimidin-3-yl]-amide;
[6-(2,4-Difluoro-phenoxy)-1H-pyrazolo [3,4-d]pyrimidin-3-yl]-(tetrahydro-pyran-4-yl)-amine;
[6-(2,4-Difluoro-phenoxy)-1H-pyrazolo[3,4-d]pyrimidin-3-yl]-(1-methanesulfonyl-piperidin4-yl)amine;
[6-(2,4-Difluoro-phenoxy)-1H-pyrazolo[3,4-d]pyrimidin-3-yl]-(2-methanesulfonyl-1-methyl-ethyl)amine;
Cyclopropylmethyl-[6-(2,4-difluoro-phenoxy)-1H-pyrazolo[3,4-d]pyrimidin-3-yl]-amine;
6-(2,4-Difluoro-phenoxy)-3-(2-methylsulfanyl-ethyl)1H-pyrazolo[3,4-d]pyrimidine;
6-(2,4-Difluoro-phenoxy)-1H-pyrazolo[3,4-d]pyrimidin-3-ylamine;
[6-(2,4-Difluoro-phenoxy)-1H-pyrazolo[3,4-d]pyrimidin-3-yl]-((R)-2-methanesulfonyl-1-methylethyl)amine;
1-[6-(2,4-Difluoro-phenoxy)-3-isopropylamino-1H-pyrazolo[3,4-d]pyrimidin-4-ylamino]-2-methyl-propan-2-ol;
1-[6-(2,4-Difluoro-phenoxy)-3-(tetrahydro-pyran-4-ylamino)-1H-pyrazolo[3,4-d]pyrimidin-4-ylamino]-2-methyl-propan-2-ol;
sec-Butyl-[6-(2,4-difluoro-phenoxy)-1H-pyrazolo[3,4-d]pyrimidin-3-yl]-amine;
[6-(2,4-Difluoro-phenoxy)-1H-pyrazolo[3,4-d]pyrimidin-3-yl]-(2,2-dimethyl-propyl)-amine;
[6-(2,4-Difluoro-phenoxy)-1H-pyrazolo[3,4-d]pyrimidin-3-yl]-((S)-2-methanesulfonyl-1-methyl-ethyl)-amine;
[6(2,4-Difluoro-phenoxy)-1H-pyrazolo[3,4-d]pyrimidin-3-yl]-(2-methanesulfonyl-ethyl)-amine;
1-[3-Amino-6-(2,4-difluoro-phenoxy)-1H-pyrazolo[3,4-d]pyrimidin-4-ylamino]-2-methyl-propan-2-ol;
[6-(2,4-Difluoro-phenoxy)-1H-pyrazolo[3,4-d]pyrimidin-3-yl]-(3-methanesulfonylpropyl)amine;
[6-(2,4-Difluoro-phenoxy)-1H-pyrazolo[3,4-d]pyrimidin-3-yl]-(3-methanesulfonyl-1-methyl-propyl)-amine;
[6-(2,4-Difluoro-phenoxy)-1H-pyrazolo[3,4-d]pyrimidin-3-yl]-(tetrahydro-thiopyran-3-yl)-amine;
[6-(2,4-Difluoro-phenoxy)-1H-pyrazolo[3,4-d]pyrimidin-3-yl]-(1,1-dioxo-hexahydro-1lambda* 6*-thiopyran-3-yl)-amine;
[6-(2,4-Difluoro-phenoxy)-1H-pyrazolo[3,4-d]pyrimidin-3-yl]-(2-ethanesulfonyl-1methyl-ethyl)-amine;
(2-Benzenesulfonyl-1-methyl-ethyl)-[6-(2,4-difluoro-phenoxy)-1H-pyrazolo[3,4-d]pyrimidin-3-yl]-amine;
[6-(2,4-Difluoro-phenoxy)-1H-pyrazolo[3,4-d]pyrimidin-3-yl]-(2-methylsulfanyl-benzyl)amine;
[6-(2,4-Difluoro-phenoxy)-1H-pyrazolo[3,4-d]pyrimidin-3-yl]-(2-methanesulfonyl-benzyl)-amine;
[6-(2,4-Difluoro-phenoxy)-1H-pyrazolo[3,4-d]pyrimidin-3-yl]-((R)-1-methyl-2-tetrazol-2-yl-ethyl)-amine;
[6-(2,4-Difluoro-phenoxy)-1H-pyrazolo[3,4-d]pyrimidin-3-yl]-((R)-1-methanesulfonylmethyl-propyl)-amine;
N-{2-[6-(2,4-Difluoro-phenoxy)-1H-pyrazolo[3,4-d]pyrimidin-3-yl]-1-methyl-ethyl}-methanesulfonamide;
{2-[6-(2,4-Difluoro-phenoxy)-1H-pyrazolo[3,4-d]pyrimidin-3-yl]-1-methyl-ethyl}-carbamic acid methyl ester;
[6-(2,4-Difluoro-phenoxy)-1H-pyrazolo[3,4-d]pyrimidin-3-yl]-(tetrahydro-tiiophen-2ylmethyl)-amine;
[6-(2,4-Difluoro-phenoxy)-1H-pyrazolo[3,4-d]pyrimidin-3-yl]-((S)1-methyl-2-tetrazol-2-yl-ethyl)-amine;
[6-(2,4-Difluoro-phenoxy)-1H-pyrazolo[3,4-d]pyrimidin-3-yl]-((R)-1-methyl-2-[1,2,3]triazol-2-yl-ethyl)-amine;
[6-(2,4-Difluoro-phenoxy)-1H-pyrazolo[3,4-d]pyrimidin-3-yl]-((S)-1-methyl-2-[1,2,3]triazol-2-yl-ethyl)-amine;
[6-(2,4-Difluoro-phenoxy)-1H-pyrazolo[3,4-d]pyrimidin-3-yl]-(1,1-dioxo-tetrahydro-1lambda*6*-thiophen-2-ylmethyl)-amine;
3-[6-(2,4-Difluoro-phenoxy)-1H-pyrazolo[3,4-d]pyrimidin-3-ylamino]-butyric acid ethyl ester;
3-[6-(2,4-Difluoro-phenoxy)1H-pyrazolo[3,4-d]pyrimidin-3-ylamino]-N-methyl-butyramide;
2-{[6-(2,4-Difluoro-phenoxy)-1H-pyrazolo[3,4-d]pyrimidin-3-ylamino]-methyl}-pyrrolidine-1-carboxylic acid methyl ester;
[6-(2,4-Difluoro-phenoxy)-1H-pyrazolo[3,4-d]pyrimidin-3-yl]-(1-methanesulfonyl-pyrrolidin-2-ylmethyl) amine;
3-[6-(2,4-Difluoro-phenoxy)-1H-pyrazolo[3,4-d]pyrimidin-3-ylamino]-N,N-dimethyl-butyramide;

[6-(2,4-Difluoro-phenoxy)-1H-pyrazolo[3,4-d]pyrimidin-3-yl]-phenyl-amine;
1-{4-[6-(2,4-Difluoro-phenoxy)-1H-pyrazolo[3,4-d]pyrimidin-3-ylamino]-piperidin-1yl}-ethanone;
2-{(R)-2-[6-(2,4-Difluoro-phenoxy)- 1H-pyrazolo[3,4-d]pyrimidin-3-ylamino]-propyl}-isoindole-1,3-dione;
[6-(2,4-Difluoro-phenoxy)-1H-pyrazolo[3,4-d]pyrimidin-3-yl]-((1S,2S)-2-methylsulfanyl-cyclopentyl)-amine;
4-[6-(2,4-Difluoro-phenoxy)-1H-pyrazolo[3,4-d]pyrimidin-3-ylamino]-piperidine-1-carboxylic acid benzyl ester;
[6-(2,4-Difluoro-phenoxy)-1H-pyrazolo[3,4-d]pyrimidin-3-yl]-((1S,2S)-2-methanesulfonyl-cyclopentyl)-amine;
N-{(R)-2-[6-(2,4-Difluoro-phenoxy)-1H-pyrazolo[3,4-d]pyrimidin-3-ylamino]-propyl}-methanesulfonamide;
{(R)-2-[6-(2,4-Difluoro-phenoxy)-1H-pyrazolo[3,4-d]pyrimidin-3-ylamino]-propyl}-carbamic acid methyl ester;
3-[6-(2,4-Difluoro-phenoxy)-1H-pyrazolo[3,4-d]pyrimidin-3-ylamino]-butyric acid;
4-[6-(2,4-Difluoro-phenoxy)-1H-pyrazolo[3,4-d]pyrimidin-3-ylamino]-piperidine-1-carboxylic acid tert-butyl ester;
N-[6-(2,4-Difluoro-phenoxy)-1H-pyrazolo[3,4-d]pyrimidin-3-yl]-N-((R)-2-methanesulfonyl1-methylethyl)-hydroxylamine;
(2-Chioro-berizyl)-[6-(2,4-difluoro-phenoxy)-1H-pyrazolo[3,4-d]pyrimidin-3-yl]-amine;
[6-(2,4-Difluoro-phenoxy)-1H-pyrazolo[3,4-d]pyrimidin-3-yl]-piperidin-4-yl-amine;
[6-(2,4-Difluoro-phenoxy)-1H-pyrazolo[3,4-d]pyrimidin-3-yl]-(1,1-dioxo-tetrahydro-1,1lambda*6*thiophen-3-yl)-amine;
[6-(2,4-Difluoro-phenoxy)-1H-pyrazolo[3,4-d]pyrimidin-3-yl]-isobutyl-amine;
[6-(2,4-Difluoro-phenoxy)-1H-pyrazolo[3,4-d]pyrimidin-3-yl]-pyrrolidin-2-ylmethyl-amine;
3-[6-(2,4-Difluoro-phenoxy)-1H-pyrazolo[3,4-d]pyrimidin-3-ylamino]-N-methoxy-N-methyl-butyramide;
4-[6-(2,4-Difluoro-phenoxy)-1H-pyrazolo[3,4-d]pyrimidin-3-ylamino]-pentan-2-one;
[6-(2,4-Difluoro-phenoxy)-1H-pyrazolo[3,4-d]pyrimidin-3-yl]-(1,1-dioxo-hexahydro-1lambda*6*-thiopyran-4-yl)-amine; and
3-[6-(2,4-Difluoro-phenoxy)-1H-pyrazolo[3,4-d]pyrimidin-3-ylamino]-butyramide.

* * * * *